(12) United States Patent
Goto et al.

(10) Patent No.: US 7,468,268 B2
(45) Date of Patent: Dec. 23, 2008

(54) NUCLEIC ACID MOLECULES ENCODING OSTEOCLASTOGENESIS INHIBITORY FACTOR PROTEINS

(75) Inventors: Masaaki Goto, Tochigi (JP); Eisuke Tsuda, Tochigi (JP); Shin'ichi Mochizuki, Tochigi (JP); Kazuki Yano, Tochigi (JP); Fumie Kobayashi, Tochigi (JP); Nobuyuki Shima, Tochigi (JP); Hisataka Yasuda, Tochigi (JP); Nobuaki Nakagawa, Tochigi (JP); Tomonori Morinaga, Tochigi (JP); Masatsugu Ueda, Kawagoe (JP); Kanji Higashio, Kawagoe (JP)

(73) Assignee: Daiichi Sankyo Co., Ltd., Tokyo (JP)

( * ) Notice: Subject to any disclaimer, the term of this patent is extended or adjusted under 35 U.S.C. 154(b) by 444 days.

(21) Appl. No.: 10/929,748

(22) Filed: Aug. 31, 2004

(65) Prior Publication Data

US 2005/0026837 A1 Feb. 3, 2005

Related U.S. Application Data

(63) Continuation of application No. 10/232,858, filed on Sep. 3, 2002, now Pat. No. 6,855,808, which is a continuation of application No. 08/915,004, filed on Aug. 20, 1997, now Pat. No. 7,125,686, which is a continuation-in-part of application No. PCT/JP96/00374, filed on Feb. 20, 1996.

(30) Foreign Application Priority Data

Feb. 20, 1995 (JP) ............................... 1995-54977
Jul. 21, 1995 (JP) ............................. 1995-207508

(51) Int. Cl.
| | |
|---|---|
| C12N 1/15 | (2006.01) |
| C12N 1/21 | (2006.01) |
| C12N 5/10 | (2006.01) |
| C12N 15/66 | (2006.01) |
| C12N 15/70 | (2006.01) |
| C12N 15/74 | (2006.01) |
| C12N 15/79 | (2006.01) |
| C12N 15/80 | (2006.01) |
| C12N 15/85 | (2006.01) |
| C12N 15/12 | (2006.01) |

(52) U.S. Cl. ............... 435/252.3; 435/325; 435/254.11; 435/320.1; 536/23.1; 536/23.5

(58) Field of Classification Search ........................ None
See application file for complete search history.

(56) References Cited

U.S. PATENT DOCUMENTS

| | | | |
|---|---|---|---|
| 4,179,337 A | 12/1979 | Davis et al. | |
| 4,710,473 A | 12/1987 | Morris | |
| 4,959,314 A | 9/1990 | Mark et al. | |
| 5,118,667 A | 6/1992 | Adams et al. | |
| 5,266,683 A * | 11/1993 | Oppermann et al. | ........ 530/326 |
| 5,366,859 A | 11/1994 | Miyoshi et al. | |
| 5,374,529 A | 12/1994 | Caterson et al. | |
| 5,393,739 A | 2/1995 | Bentz et al. | |
| 5,427,954 A | 6/1995 | Sandy et al. | |
| 5,447,851 A | 9/1995 | Beutler et al. | |
| 5,457,035 A | 10/1995 | Baum et al. | |
| 5,545,722 A | 8/1996 | Naka | |
| 5,578,569 A | 11/1996 | Tam | |
| 5,585,479 A | 12/1996 | Hoke et al. | |
| 5,599,708 A | 2/1997 | Mundy et al. | |
| 5,658,756 A | 8/1997 | Rodan et al. | |
| 5,736,506 A | 4/1998 | Naka | |
| 5,830,850 A | 11/1998 | Gelb et al. | |
| 5,843,678 A | 12/1998 | Boyle | |
| 5,843,901 A | 12/1998 | Roeske | |
| 5,985,832 A | 11/1999 | Roodman et al. | |
| 6,015,938 A | 1/2000 | Boyle et al. | |
| 6,017,729 A | 1/2000 | Anderson et al. | |
| 6,046,033 A | 4/2000 | Goto et al. | |
| 6,087,555 A | 7/2000 | Dunstan et al. | |
| 6,242,213 B1 | 6/2001 | Anderson | |
| 6,242,586 B1 | 6/2001 | Gorman et al. | |
| 6,271,349 B1 | 8/2001 | Dougall et al. | |
| 6,284,485 B1 | 9/2001 | Boyle et al. | |

(Continued)

FOREIGN PATENT DOCUMENTS

EP 0514130 A2 11/1992

(Continued)

OTHER PUBLICATIONS

Langdahl et al., J Bone Miner Res. Jul. 2002;17(7):1245-55.*
Daroszewska et al., J Bone Miner Res. Sep. 2004; 19:1506-11.*
Zubler RH; Swiss Med Wkly. Dec. 23, 2006;136(49-50):795-9.*
Phillips, A., J Pharm Pharmacology 53: 1169-1174, 2001.*
Lewis et al. Proc Natl Acad Sci. USA. 1991;88: 2830-2834.*
Principles of nucleic acid hybridization, downloaded on Dec. 15, 2007 from ncbi.nlm.nih.gov/books/bv.fcgi?rid=hmg.section.484; 4 pages.*
Jean-Jacques Body, "Current and Future Directions in Medical Therapy: Hypercalcemia," *Cancer Supplement*, 88(12):3054-3058 (2000).

(Continued)

*Primary Examiner*—Elizabeth C. Kemmerer
(74) *Attorney, Agent, or Firm*—Arnold & Porter LLP

(57) ABSTRACT

A protein which inhibits osteoclast differentiation and/or maturation and a method for producing the protein. The protein is produced by human embryonic lung fibroblasts and has a molecular weight of about 60 kD and about 120 kD under non-reducing conditions and about 60 kD under reducing conditions on SDS-polyacrylamide gel electrophoresis. The protein can be isolated and purified from the culture medium of fibroblasts. Furthermore, the protein can be produced by gene engineering. The present invention includes cDNA for producing the protein by gene engineering, antibodies having specific affinity for the protein or a method for determining protein concentration using these antibodies.

12 Claims, 12 Drawing Sheets

U.S. PATENT DOCUMENTS

| | | | |
|---|---|---|---|
| 6,284,728 B1 | 9/2001 | Boyle et al. |
| 6,284,740 B1 | 9/2001 | Boyle et al. |
| 6,288,032 B1 | 9/2001 | Boyle et al. |
| 6,297,022 B1 | 10/2001 | McDonnell et al. |
| 6,316,408 B1 | 11/2001 | Boyle |
| 6,369,027 B1 | 4/2002 | Boyle et al. |
| 6,419,929 B1 | 7/2002 | Anderson |
| 6,479,635 B1 | 11/2002 | Anderson et al. |
| 6,525,180 B1 | 2/2003 | Gorman et al. |
| 6,528,482 B1 | 3/2003 | Anderson et al. |
| 6,537,763 B2 | 3/2003 | Dougall et al. |
| 6,562,948 B2 | 5/2003 | Anderson |
| 6,613,544 B1 | 9/2003 | Boyle et al. |
| 6,649,164 B2 | 11/2003 | Maraskovsky |
| 6,693,175 B2 | 2/2004 | Yano et al. |
| 6,740,522 B2 | 5/2004 | Anderson |
| 2002/0081720 A1 | 6/2002 | Dougall et al. |
| 2002/0086826 A1 | 7/2002 | Anderson et al. |
| 2002/0086827 A1 | 7/2002 | Anderson et al. |
| 2002/0127637 A1 | 9/2002 | Ni et al. |
| 2002/0150989 A1 | 10/2002 | Greene et al. |
| 2002/0169117 A1 | 11/2002 | Maraskovsky |
| 2003/0045456 A1 | 3/2003 | Yamamoto et al. |
| 2003/0100069 A1 | 5/2003 | Ni et al. |
| 2003/0100488 A1 | 5/2003 | Boyle |
| 2003/0103978 A1 | 6/2003 | Deshpande et al. |
| 2003/0104485 A1 | 6/2003 | Boyle |
| 2003/0139325 A1 | 7/2003 | Yamamoto et al. |
| 2003/0144480 A1 | 7/2003 | Gorman et al. |
| 2003/0166097 A1 | 9/2003 | Greene et al. |
| 2003/0175840 A1 | 9/2003 | Anderson et al. |
| 2003/0176647 A1 | 9/2003 | Yamaguchi et al. |
| 2003/0181418 A1 | 9/2003 | Kumakura et al. |
| 2003/0207827 A1 | 11/2003 | Boyle et al. |
| 2003/0208045 A1 | 11/2003 | Yamaguchi et al. |
| 2003/0216297 A1 | 11/2003 | Kumakura et al. |
| 2004/0033535 A1 | 2/2004 | Boyle et al. |

FOREIGN PATENT DOCUMENTS

| | | | |
|---|---|---|---|
| EP | 0514130 A3 | 11/1992 |
| EP | 0526905 A2 | 2/1993 |
| EP | 0526905 A3 | 2/1993 |
| EP | 0727211 A1 | 8/1996 |
| EP | 0 784 093 A1 | 7/1997 |
| EP | 0874045 A1 | 10/1998 |
| EP | 0911342 A1 | 4/1999 |
| EP | 0 974 671 A1 | 1/2000 |
| EP | 1 127 578 A1 | 8/2001 |
| EP | 1 270 015 A2 | 1/2003 |
| EP | 1 270 015 A3 | 2/2004 |
| JP | 62-201825 | 9/1987 |
| NZ | 330400 | 5/1999 |
| WO | 86/00922 A1 | 2/1986 |
| WO | 90/14363 A1 | 11/1990 |
| WO | 93/12227 A1 | 6/1993 |
| WO | 93/21946 A1 | 11/1993 |
| WO | 95/11308 A1 | 4/1995 |
| WO | 96/28546 A1 | 9/1996 |
| WO | 97/00317 A1 | 1/1997 |
| WO | 97/00318 A1 | 1/1997 |
| WO | 97/23614 A1 | 7/1997 |
| WO | 98/07840 A1 | 2/1998 |
| WO | 98/25958 A2 | 6/1998 |
| WO | 98/28424 A2 | 7/1998 |
| WO | 98/28426 A2 | 7/1998 |
| WO | 98/46211 A1 | 10/1998 |
| WO | 98/46644 A1 | 10/1998 |
| WO | 98/46751 A1 | 10/1998 |
| WO | 98/49305 A1 | 11/1998 |
| WO | 99/15691 A1 | 4/1999 |
| WO | 99/19468 A1 | 4/1999 |
| WO | 99/53942 A1 | 10/1999 |
| WO | 99/58674 A2 | 11/1999 |
| WO | 99/58674 A3 | 11/1999 |
| WO | 01/03719 A2 | 1/2001 |
| WO | 01/03719 A3 | 1/2001 |
| WO | 01/17543 A2 | 3/2001 |
| WO | 01/17543 A3 | 3/2001 |
| WO | 01/18203 A1 | 3/2001 |
| WO | 01/44472 A1 | 6/2001 |
| WO | 03/002713 A2 | 1/2003 |
| WO | 03/074084 A1 | 9/2003 |

OTHER PUBLICATIONS

*Chemical Abstracts*, vol. 123, No. 18, Abstract No. 237583p (1995).

Chowdhury et al., "Effects of Heparin on Osteoclast Activity," *Journal of Bone and Mineral Research*, 7(7):771-777 (1992).

Cochran and Abernathy, "Modulation of Bone Resorption by Glycosaminoglycans: Effects of Parathyroid Hormone and Interleukin-1," *Bone*, 9(5):331-335 (1988).

Fautrel and Guillemin, "Cost of illness studies in rheumatic diseases," *Current Opinion in Rheumatology*, 14:121-126 (2002).

Green et al., "Renal Tolerability Profile of Novel, Potent Bisphosphonates in Two Short-Term Rat Models," *Pharmacology & Toxicology*, 80:225-230 (1997).

Iqbal and Sobhan, "Osteoporosis: A Review," *Missouri Medicine*, 99(1):19-24 (2002).

Porcel et al., "Anaphylaxis to calcitonin," *Allergologia et immunopathologia*, 28(4):243-245 (2000).

Romas et al., "Involvement of Receptor Activator of NFκB Ligand and Tumor Necrosis Factor-α in Bone Destruction in Rheumatoid Arthritis," *Bone*, 30(2):340-346 (2002).

Tomoyasu et al., "Characterization of Monomeric and Homodimeric Forms of Osteoclastogenesis Inhibitory Factor," *Biochemical and Biophysical Research Communications*, 245(2):382-387 (1998).

White and Schilling, "Postmenopausal Hormone Replacement: Historical Perspectives and Current Concerns," *Clinical Excellence for Nurse Practitioners*, 4(5):277-285 (2000).

Yamamoto et al., "Hypocalcemic Effect of Osteoclastogenesis Inhibitory Factor/Osteoprotegerin in the Thyroparathyroidectomized Rat," *Endocrinology*, 139(9):4012-4015 (1998).

Adams et al., "Complementary DNA Sequencing: Expressed Sequence Tags and Human Genome Project", *Science*, 252:1651-1656 (1991).

Anderson et al., "A homologue of the TNF receptor and its ligand enhance T-cell growth and dendritic-cell function", *Nature*, 390:175-179 (1997).

Banks et al., "Effect of degenerative spinal and aortic calcification on bone density measurements in post-menopausal women: links between osteoporosis and cardiovascular disease?", *European Journal of Clinical Investigation*, 24(12):813-817 (1994).

Banner et al., "Crystal Structure of the Soluble Human 55 kd TNF Receptor-Human TNFβ Complex: Implications of TNF Receptor Activation", *Cell*, 73(3):431-445 (1993).

Bennett, C. F., "Antisense Research", *Science*, 271:434 (1996).

Beutler and Cerami, "Tumor Necrosis, Cachexia, Shock, and Inflammation: a Common Mediator", *Annual Review of Biochemistry*, 57:505-518 (1988).

Beutler and van Huffel, "Unraveling Function in the TNF Ligand and Receptor Families", *Science*, 264:667-668 (1994).

Boyce et al., "Effects of Interleukin-1 on Bone Turnover in Normal Mice", *Endocrinology*, 125(3):1142-1150 (1989).

Bradley and Robertson, "Embryo-Derived Stem Cells: a Tool for Elucidating the Developmental Genetics of the Mouse", *Current Topics in Developmental Biology*, 20:357-371 (1986).

Brinster et al., "Factors affecting the efficiency of introducing foreign DNA into mice by microinjecting eggs", *Proceedings of the National Academy of Sciences of USA*, 82:4438-4442 (1985).

Bucay et al., "*osteoprotegerin*-deficient mice develop early onset osteoporosis and arterial calcification", *Genes and Development*, 12(9):1260-1268 (1998).

Capon et al., "Designing CD4 immunoadhesins for AIDS therapy", *Nature*, 337(6207):525-531 (1989).

Cappecchi, M. R., "Altering the Genome by Homologous Recombination", *Science*, 244:1288-1292 (1989).

Chambers et al., "Generation of osteoclast-inductive and osteoclastogenic cell lines from the $H$-$2K^b tsA58$ transgenic mouse", *Proceedings of the National Academy of Sciences of USA*, 90:5578-5582 (1993).

Charreau et al., "Transgenesis in rats: technical aspects and models", *Transgenic Research*, 5(4):223-234 (1996).

Chen et al., "Mapping the Domain(s) Critical for the Binding of Human Tumor Necrosis Factor-α to Its Two Receptors", *Journal of Biological Chemistry*, 270(6):2874-2878 (1995).

Chenu et al., "Transforming growth factor β inhibits formation of osteoclast-like cells in long-term human marrow cells", *Proceedings of the National Academy of Sciences of USA*, 85(15):5683-5687 (1988).

Chomczynski and Sacchi, "Single-Step Method of RNA Isolation by Acid Guanidinium Thiocyanate-Phenol-Chloroform Extraction", *Analytical Biochemistry*, 162(1):156-159 (1987).

Culver and Blaese, "Gene therapy for cancer", *Trends in Genetics*, 10(5):174-178 (1994).

Database EMEST16, EMBL Database Accession No. AA170348.

Database GenEMBL, EMBL Accession No. AF019048.

Database EMROD, EMBL Database Accession No. M59378.

DeClerck et al., "Inhibition of Autoproteolytic Activation of Interstitial Procollagenase by Recombinant Metalloproteinase Inhibitor M1/TIMP-2", *Journal of Biological Chemistry*, 266(6):3893-3899 (1991).

Demer, L. L., "A Skeleton in the Atherosclerosis Closet", *Circulation*, 92(8):2029-2032 (1995).

Ebi et al., "Mechanism of Mast Cell Deficiency in Mutant Mice of *mi/mi* Genotype: An Analysis by Co-Culture of Mast Cells and Fibroblasts", *Blood*, 75(6):1247-1251 (1990).

Efrat, S., "Prospects for gene therapy of insulin-dependent diabetes mellitus", *Diabetologia*, 41(12):1401-1409 (1998).

Ellison et al., "The nucleotide sequence of a human immunoglobulin $C_{\gamma 1}$ gene", *Nucleic Acids Research*, 10(13):4071-4079 (1982).

Engels and Uhlmann, "Gene Synthesis", *Angew. Chem. Int. Ed. Engl.*, 28:716-734 (1989).

Fawthrop et al., "The Effect of Transforming Growth Factor β on the Plasminogen Activator Activity of Normal Human Osteoblast-like Cells and a Human Osteosarcoma Cell Line MG-63", *Journal of Bone and Mineral Research*, 7(12):1363-1371 (1992).

Fenton et al., "Long-Term Culture of Disaggregated Rat Osteoclasts: Inhibition of Bone Resorption and Reduction of Osteoclast-Like Cell Number by Calcitonin and PTHrP[107-139]", *Journal of Cellular Physiology*, 155:1-7 (1993).

Fisher et al., "Dominant Interfering Fas Gene Mutations Impair Apoptosis in a Human Autoimmune Lymphoproliferative Syndrome", *Cell*, 81(6):935-946 (1995).

Galli-Taliadoros et al., "Gene knock-out technology: a methodological overview for the interested novice", *Journal of Immunological Methods*, 181(1):1-15 (1995).

George et al., "Current Methods in Sequence Comparison and Analysis", *Macromolecular Sequencing and Synthesis Selected Methods and Applications*, pp. 127-149 (1988).

Goeddel, D. V., "Systems for Heterologous Gene Expression", *Methods in Enzymology*, 185:3-7 (1990).

Goeddel et al., "Tumor Necrosis Factors: Gene Structure and Biological Activities", *Cold Spring Harbor Symposia on Quantitative Biology*, vol. LI., pp. 597-609 (1986).

Goodwin et al., "Molecular Cloning and Expression of the Type 1 and Type 2 Murine Receptors for Tumor Necrosis Factor", *Molecular and Cellular Biology*, 11(6):3020-3026 (1991).

Gowen et al., "Preferential Inhibition of Cytokine-Stimulated Bone Resorption by Recombinant Interferon Gamma", *Journal of Bone and Mineral Research*, 1(5):469-474 (1986).

Graves and Jilka, "Comparison of Bone and Parathyroid Hormone as Stimulators of Osteoclast Development and Activity in Calvarial Cell Cultures From Normal and Osteopetrotic (mi/mi) Mice", *Journal of Cellular Physiology*, 145(1):102-109 (1990).

Gribskov et al., "Profile analysis: Detection of distantly related proteins", *Proceedings of the National Academy of Sciences of USA*, 84(13):4355-4358 (1987).

Grigoriadis et al., "c-Fos: A Key Regulator of Osteoclast-Macrophage Lineage Determination and Bone Remodeling", *Science*, 266:443-448 (1994).

Hattersley et al., "Human Macrophage Colony-Stimulating Factor Inhibits Bone Resorption by Osteoclasts Disaggregated From Rat Bone", *Journal of Cellular Physiology*, 137(1):199-203 (1988).

Hodgson et al., "Advances in vector systems for gene therapy", *Exp. Opin. Ther. Patents*, 5(5):459-468 (1995).

International Search Report, International Application No. PCT/JP96/00374 (1996).

International Search Report, International Application No. PCT/JP98/01728 (1998).

Isozaki et al., "Cell Type-Specific Deficiency of c-*kit* Gene Expression in Mutant Mice of *mi/mi* Genotype", *American Journal of Pathology*, 145(4):827-836 (1994).

Jimi et al., "Osteoclast function is activated by osteoblastic cells through a mechanism involving cell-to-cell contact", *Endocrinology*, 137(5):2187-2190 (1996).

Johnson et al., "Pleiotropic Effects of a Null Mutation in the c-*fos* Proto-Oncogene", *Cell*, 71(4):577-586 (1992).

Kaji et al., "Insulin-Like Growth Factor-I Mediates Osteoclast-Like Cell Formation Stimulated by Parathyroid Hormone", *Journal of Cellular Physiology*, 172(1):55-62 (1997).

Karaplis, A. C., "Gene Targeting", *Principles of Bone Biology*, pp. 1189-1201, Academic Press (1996).

Kasono et al., Inhibitory effect of interleukin-4 on osteoclast-like cell formation in mouse bone marrow culture, *Bone and Mineral*, 21(3):179-188 (1993).

Kohno et al., "A second tumor necrosis factor receptor gene product can shed a naturally occurring tumor necrosis factor inhibitor", *Proceedings of the National Academy of Sciences of USA*, 87(21):8331-8335 (1990).

Kraulis, P. J., "*MOLSCRIPT*: a program to produce both detailed and schematic plots of protein structures", *Journal of Applied Crystallography*, 24(5):946-950 (1991).

Kukita et al., "Osteoinductive factor inhibits formation of human osteoclast-like cells", *Proceedings of the National Academy of Sciences of USA*, 87:3023-3026 (1990).

Lacey et al., "Interleukin 4, Interferon-γ, and Prostaglandin E Impact the Osteoclastic Cell-Forming Potential of Murine Bone Marrow Macrophages", *Endocrinology*, 136(6):2367-2376 (1995).

Levine and Williams, "Automated measurements of mouse apolipoprotein B: convenient screening tool for mouse models of atherosclerosis", *Clinical Chemistry*, 43(4):669-674 (1997).

Lewis et al., "Cloning and expression of cDNAS for two distinct murine tumor necrosis factor receptors demonstrate one receptor is species specific", *Proceedings of the National Academy of Sciences of USA*, 88:2830-2834 (1991).

Loetscher et al., "Tumor Necrosis Factor: Receptors and Inhibitors", *Cancer Cells*, 3(6):221-226 (1991).

Lowe et al., "Osteopetrosis in Src-deficient mice is due to an autonomous defect of osteoclasts" *Proceedings of the National Academy of Sciences of USA*, 90(10):4485-4489 (1993).

Lüthy et al., "Improving the sensitivity of the sequence profile method", *Protein Science*, 3(1):139-146 (1994).

MacDonald et al., "Isolation of RNA Using Guanidinium Salts", *Methods in Enzymology*, 152:219-227 (1987).

Maitland and McDougal, "Biochemical Transformation of Mouse Cells by Fragments of Herpes Simplex Virus DNA", *Cell*, 11(1):233-241 (1977).

Marks, Jr., and Lane, "Osteopetrosis, a New Recessive Skeletal Mutation on Chromosome 12 of the Mouse", *Journal of Heredity*, 67(1):11-18 (1976).

Marshall, E., "Gene Therapy's Growing Pains", *Science*, 269:1050-1055 (1995).

Martin et al., "Interleukins in the Control of Oosteoclast Differentiation", *Critical Reviews™ in Eukaryotic Gene Expression*, 8(2):107-23 (1998).

Matsudaira, P., "Sequence from Picomole Quantities of Proteins Electroblotted onto Polyvinylidene Difluoride Membranes", *Journal of Biological Chemistry*, 262(21):10035-10038 (1987).

Miller and Vile, "Targeted vectors for gene therapy", *FASEB Journal*, 9(2):190-199 (1995).

Miller and Vile, "Gene Transfer and Antisense Nucleic Acid Techniques", *Parasitology Today*, 10(3):92-97 (1994).

Milligan et al., "Current Concepts in Antisense Drug Design", *Journal of Medicinal Chemistry*, 36(14):1923-1937 (1993).

Mizuno et al., "Severe Osteoporosis in Mice Lacking Osteoclastogenesis Inhibitory Factor/Osteoprotegerin", *Biochemical and Biophysical Research Communications*, 247(3):610-615 (1998).

Montgomery et al., "Herpes Simplex Virus-1 Entry into Cells Mediated by a Novel Member of the TNF/NGF Receptor Family", *Cell*, 87(3):427-436 (1996).

Morony et al., "A Chimeric Form of Osteoprotegerin Inhibits Hypercalcemia and Bone Resorption Induced by IL-1β, TNF-α, PTH, PTHrP, and 1,25(OH)$_2$D$_3$", *Journal of Bone and Mineral Research*, 14(9):1478-1485 (1999).

Mundy et al., "The Effects of Cytokines and Growth Factors on Osteoblastic Cells", *Bone*, 17(2 Suppl):71S-75S (1995).

Nagata and Goldstein, "The Fas Death Factor", *Science*, 267:1449-1456 (1995).

Ogden and Adams, "Electrophoresis in Agarose and Acrylamide Gels", *Methods in Enzymology*, 152:61-87 (1987).

Parhami and Demer, "Arterial calcification in face of osteoporosis in ageing: can we blame oxidized lipids", *Current Opinion in Lipidology*, 8(5):312-314 (1997).

Pearson, W. R., "Rapid and Sensitive Sequence Comparison with FASTP and FASTA", *Methods in Enzymology*, 183:63-98 (1990).

Perigaud et al., "Nucleoside analogues as chemotherapeutic agents: a review", *Nucleosides & Nucleotides*, 11(2-4):903-945 (1992).

Reddi, A. H., "Bone Morphogenesis and Modeling: Soluble Signals Sculpt Osteosomes in the Solid State", *Cell*, 89:159-161 (1997).

Rieger et al., *Glossary of Genetics and Cytogenetics*, p. 17, Springer-Verlag, Berlin Heidlberg, New York (1976).

Rojanasakul, Y., "Antisense oligonucleotide therapeutics: drug delivery and targeting", *Advanced Drug Delivery Reviews*, 18:115-131 (1996).

Roodman, G. D., "Role of Cytokines in the Regulation of Bone Resorption", *Calcified Tissue International*, 53(Suppl. 1):S94-S98 (1993).

Rosati et al., "Normal long bone growth and development in type X collagen-null mice", *Nature Genetics*, 8(2):129-135 (1994).

Schinke et al., "Molecular determinants of arterial calcification", *Annals of Medicine*, 30(6):538-541 (1998).

Shahinian et al., "Differential T Cell Costimulatory Requirements in CD28-Deficient Mice", *Science*, 261:609-612 (1993).

Siddhanti et al., "Molecular to Pharmacologic Control of Osteoblast Proliferation and Differentiation", *Journal of Cellular Biochemistry*, 55(3):310-320 (1994).

Simonet et al., "Long-term Impaired Neutrophil Migration in Mice Overexpressing Human Interleukin-8", *Journal of Clinical Investigation*, 94(3):1310-1319 (1994).

Simonet et al., "Osteoprotegerin: A Novel Secreted Protein Involved in the Regulation of Bone Density", *Cell*, 89:309-319 (1997).

Smith et al., "The TNF Receptor Superfamily of Cellular and Viral Proteins: Activation, Costimulation, and Death", *Cell*, 76:959-962 (1994).

Soriano et al., "Targeted Disruption of the c-*src* Proto-Oncogene Leads to Osteopetrosis in Mice", *Cell*, 64(4):693-702 (1991).

Stein and Cheng, "Antisense Oligonucleotides as Therapeutic Agents—Is the Bullet Really Magical?", *Science*, 261:1004-1012 (1993).

Stull and Szoka, Jr., "Antigene, Ribozyme and Aptamer Nucleic Acid Drugs: Progress and Prospects", *Pharmaceutical Research*, 12(4):465-483 (1995).

Suda et al., "Modulation of Osteoclast Differentiation by Local Factors", *Bone*, 17(2 Suppl):87S-91S (1995).

Suda et al., "Molecular Cloning and Expression of the Fas Ligand, a Novel Member of the Tumor Necrosis Factor Family", *Cell*, 75(6):1169-1178 (1993).

Takada et al., "A simple method to assess osteoclast-mediated bone resorption using unfractionated bone cells", *Bone and Mineral*, 17:347-359 (1992).

Tsuda et al., "Isolation of a Novel Cytokine from Human Fibroblasts That Specifically Inhibits Osteoclastogenesis", *Biochemical and Biophysical Research Commununications*, 234(1):137-142 (1997).

Udagawa et al., "The Bone Marrow-Derived Stromal Cell Lines MC3T3-G2/PA6 and ST2 Support Osteoclast-Like Cell Differentiation in Cocultures with Mouse Spleen Cells", *Endocrinology*, 125(3):1805-1813 (1989).

Udagawa et al., "Origin of osteoclasts: Mature monocytes and macrophages are capable of differentiating into osteoclasts under a suitable microenvironment prepared by bone marrow-derived stromal cells", *Proceedings of the National Academy of Sciences of USA*, 87(18):7260-7264 (1990).

Wagner, R. W., "Gene inhibition using antisense oligodeoxynucleotides", *Nature*, 372(6504):333-335 (1994).

Wang, "Bone and haematopoietic defects in mice lacking c-*fos*", *Nature*, 360(6406):741-745 (1992).

Watanabe et al., "Interleukin-4 as a Potent Inhibitor of Bone Resorption", *Biochemical and Biophysical Research Communications*, 172(3):1035-1041 (1990).

Westermann et al., "Inhibition of expression of SV40 virus large T-antigen by antisense oligodeoxyribonucleotides" *Biomedica Biochimica Acta*, 48(1):85-93 (1989).

Wiktor-Jedrzejczak et al., "Hematological Characterization of Congenital Osteopetrosis in *op/op* Mouse (Possible Mechanism for Abnormal Macrophage Differentiation)", *Journal of Experimental Medicine*, 156(5):1516-1527 (1982).

Wiktor-Jedrzejczak et al., "Total absence of colony-stimulating factor 1 in the macrophage-deficient osteopetrotic (*op/op*) mouse", *Proceedings of the National Academy of Sciences of USA*, 87(12):4828-4832 (1990).

Wiley et al., "Identification and Characterization of a New Member of the TNF Family that Induces Apoptosis", *Immunity*, 3(6):673-682 (1995).

Wong et al., "Trance Is a Novel Ligand of the Tumor Necrosis Factor Receptor Family That Activates c-Jun N-terminal Kinase in T Cells", *Journal of Biological Chemistry*, 272(40):25190-25194 (1997).

Wu-Pong, S., "Oligonucleotides: Opportunities for Drug Therapy and Research", *Pharmaceutical Technology*, 118:102-114 (1994).

Yamaguchi et al., "Characterization of Structural Domains of Human Osteoclastogenesis Inhibitory Factor", *Journal of Biological Chemistry*, 273(9):5117-5123 (1998).

Yan and Chao, "Disruption of Cysteine-rich Repeats of the p75 Nerve Growth Factor Receptor Leads to Loss of Ligand Binding", *Journal of Biological Chemistry*, 266(18):12099-12104 (1991).

Yang et al., "Eradication of Established Tumors by a Fully Human Monoclonal Antibody to the Epidermal Growth Factor Receptor without Concomitant Chemotherapy", *Cancer Research*, 59(6):1236-1243 (1999).

Yasuda et al., "Osteoclast differentiation factor is a ligand for osteoprotegerin/ osteoclastogenesis-inhibitory factor and is identical to Trance/Rankl", *Proceedings of the National Academy of Sciences of USA*, 95(7):3597-3602 (1998).

Yoneda et al., "Sumarin Suppresses Hypercalcemia and Osteoclastic Bone Resorption in Nude Mice Bearing a Human Squamous Cancer", *Cancer Research*, 55:1989-1993 (1995).

Yoshida et al., "The murine mutation osteopetrosis is in the coding region of the macrophage colony stimulating factor gene", *Nature*, 345(6274):442-444 (1990).

\* cited by examiner

OCIF ACTIVITY

| DILUTION | FRACTIONS | | | |
|---|---|---|---|---|
| | 1-10 | 11-20 | 21-30 | 31-40 |
| 1/100 | - | ++ | ++ | - |
| 1/500 | - | ++ | ++ | - |

*FIG. 1B*

1
MNNLLCCALVFLDISIKWTTQETFPPKYLHYDEETSHQLLCDKCPPGTYLKQHCTAKWKT (OCIF1,SEQ ID NO:5)
************************************************************
MNNLLCCALVFLDISIKWTTQETFPPKYLHYDEETSHQLLCDKCPPGTYLKQHCTAKWKT (OCIF2,SEQ ID NO:9)
1

61
VCAPCPDHYYTDSWHTSDECLYCSPVCKELQYVKQECNRTHNRVCECKEGRYLEIEFCLK (OCIF1,SEQ ID NO:5)
*************************        ***********************
VCAPCPDHYYTDSWHTSDECLYCSPVCKE-------CNRTHNRVCECKEGRYLEIEFCLK (OCIF2,SEQ ID NO:9)
61

121
HRSCPPGFGVVQAGTPERNTVCKRCPDGFFSNETSSKAPCRKHTNCSVFGLLLTQKGNAT (OCIF1,SEQ ID NO:5)
************************************************************
HRSCPPGFGVVQAGTPERNTVCKRCPDGFFSNETSSKAPCRKHTNCSVFGLLLTQKGNAT (OCIF2,SEQ ID NO:9)
114

181
HDNICSGNSESTQKCGIDVTLCEEAFFRFAVPTKFTPNWLSVLVDNLPGTKVNAESVERI (OCIF1,SEQ ID NO:5)
************************************************************
HDNICSGNSESTQKCGIDVTLCEEAFFRFAVPTKFTPNWLSVLVDNLPGTKVNAESVERI (OCIF2,SEQ ID NO:9)
174

241
KRQHSSQEQTFQLLKLWKHQNKDQDIVKKIIQDIDLCENSVQRHIGHANLTFEQLRSLME (OCIF1,SEQ ID NO:5)
************************************************************
KRQHSSQEQTFQLLKLWKHQNKDQDIVKKIIQDIDLCENSVQRHIGHANLTFEQLRSLME (OCIF2,SEQ ID NO:9)
234

301
SLPGKKVGAEDIEKTIKACKPSDQILKLLSLWRIKNGDQDTLKGLMHALKHSKTYHFPKT (OCIF1,SEQ ID NO:5)
************************************************************
SLPGKKVGAEDIEKTIKACKPSDQILKLLSLWRIKNGDQDTLKGLMHALKHSKTYHFPKT (OCIF2,SEQ ID NO:9)
294

361
VTQSLKKTIRFLHSFTMYKLYQKLFLEMIGNQVQSVKISCL (OCIF1,SEQ ID NO:5)
****************************************
VTQSLKKTIRFLHSFTMYKLYQKLFLEMIGNQVQSVKISCL (OCIF2,SEQ ID NO:9)
354

FIG. 9

```
1
MNNLLCCALVFLDISIKWTTQETFPPKYLHYDEETSHQLLCDKCPPGTYLKQHCTAKWKT  (OCIF1,SEQ ID NO:5)
** *********************************************************
MNKLLCCALVFLDISIKWTTQETFPPKYLHYDEETSHQLLCDKCPPGTYLKQHCTAKWKT  (OCIF3,SEQ ID NO:11)
1

61
VCAPCPDHYYTDSWHTSDECLYCSPVCKELQYVKQECNRTHNRVCECKEGRYLEIEFCLK  (OCIF1,SEQ ID NO:5)
************************************************************
VCAPCPDHYYTDSWHTSDECLYCSPVCKELQYVKQECNRTHNRVCECKEGRYLEIEFCLK  (OCIF3,SEQ ID NO:11)
61

121
HRSCPPGFGVVQAGTPERNTVCKRCPDGFFSNETSSKAPCRKHTNCSVFGLLLTQKGNAT  (OCIF1,SEQ ID NO:5)
************************************************************
HRSCPPGFGVVQAGTPERNTVCKRCPDGFFSNETSSKAPCRKHTNCSVFGLLLTQKGNAT  (OCIF3,SEQ ID NO:11)
121

181
HDNICSGNSESTQKCGIDVTLCEEAFFRFAVPTKFTPNWLSVLVDNLPGTKVNAESVERI  (OCIF1,SEQ ID NO:5)
************************************************************
HDNICSGNSESTQKCGIDVTLCEEAFFRFAVPTKFTPNWLSVLVDNLPGTKVNAESVERI  (OCIF3,SEQ ID NO:11)
181

241
KRQHSSQEQTFQLLKLWKHQNKDQDIVKKIIQDIDLCENSVQRHIGHANLTFEQLRSLME  (OCIF1,SEQ ID NO:5)
***************************************************
KRQHSSQEQTFQLLKLWKHQNKDQDIVKKIIQDIDLCENSVQRHIGHANLS---------  (OCIF3,SEQ ID NO:11)
241

301
SLPGKKVGAEDIEKTIKACKPSDQILKLLSLWRIKNGDQDTLKGLMHALKHSKTYHFPKT  (OCIF1,SEQ ID NO:5)
                              ******************************
-------------------------------LWRIKNGDQDTLKGLMHALKHSKTYHFPKT  (OCIF3,SEQ ID NO:11)
                              292

361
VTQSLKKTIRFLHSFTMYKLYQKLFLEMIGNQVQSVKISCL  (OCIF1,SEQ ID NO:5)
****************************************
VTQSLKKTIRFLHSFTMYKLYQKLFLEMIGNQVQSVKISCL  (OCIF3,SEQ ID NO:11)
322
```

FIG. 10

```
1
MNNLLCCALVFLDISIKWTTQETFPPKYLHYDEETSHQLLCDKCPPGTYLKQHCTAKWKT  (OCIF1,SEQ ID NO:5)
** **** *****************************************************
MNKLLCCSLVFLDISIKWTTQETFPPKYLHYDEETSHQLLCDKCPPGTYLKQHCTAKWKT  (OCIF4,SEQ ID NO:13)
1

61
VCAPCPDHYYTDSWHTSDECLYCSPVCKELQYVKQECNRTHNRVCECKEGRYLEIEFCLK  (OCIF1,SEQ ID NO:5)
************************************************************
VCAPCPDHYYTDSWHTSDECLYCSPVCKELQYVKQECNRTHNRVCECKEGRYLEIEFCLK  (OCIF4,SEQ ID NO:13)
61

121
HRSCPPGFGVVQAGTPERNTVCKRCPDGFFSNETSSKAPCRKHTNCSVFGLLLTQKGNAT  (OCIF1,SEQ ID NO:5)
**************
HRSCPPGFGVVQAGTCQCAAKLIRIMQSQIVVTV                            (OCIF4,SEQ ID NO:13)
121
```

FIG. 11

```
1
MNNLLCCALVFLDISIKWTTQETFPPKYLHYDEETSHQLLCDKCPPGTYLKQHCTAKWKT  (OCIF1,SEQ ID NO:5)
** *********************************************************
MNKLLCCALVFLDISIKWTTQETFPPKYLHYDEETSHQLLCDKCPPGTYLKQHCTAKWKT  (OCIF5,SEQ ID NO:15)
1

61
VCAPCPDHYYTDSWHTSDECLYCSPVCKELQYVKQECNRTHNRVCECKEGRYLEIEFCLK  (OCIF1,SEQ ID NO:5)
************************************************************
VCAPCPDHYYTDSWHTSDECLYCSPVCKELQYVKQECNRTHNRVCECKEGRYLEIEFCLK  (OCIF5,SEQ ID NO:15)
61

121
HRSCPPGFGVVQAGTPERNTVCKRCPDGFFSNETSSKAPCRKHTNCSVFGLLLTQKGNAT  (OCIF1,SEQ ID NO:5)
************* *
HRSCPPGFGVVQAGCRRRPKPQICI                                     (OCIF5,SEQ ID NO:15)
121
```

FIG. 12

A: NORMAL RAT
B: DENERVED RAT + VEHICLE
C: DENERVED RAT + OCIF 10 μg/kg/day
D: DENERVED RAT + OCIF 100 μg/kg/day

```
                        SEQUENCE LISTING

<160> NUMBER OF SEQ ID NOS: 108

<210> SEQ ID NO 1
<211> LENGTH: 6
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: X = unknown

<400> SEQUENCE: 1

Xaa Tyr His Phe Pro Lys
1               5

<210> SEQ ID NO 2
<211> LENGTH: 14
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: X = unknown
<220> FEATURE:
<221> NAME/KEY: MISC_FEATURE
<222> LOCATION: (5)..(5)
<223> OTHER INFORMATION: X = unknown
<220> FEATURE:
<221> NAME/KEY: MISC_FEATURE
<222> LOCATION: (13)..(13)
<223> OTHER INFORMATION: X = unknown

<400> SEQUENCE: 2

Xaa Gln His Ser Xaa Gln Glu Gln Thr Phe Gln Leu Xaa Lys
1               5                   10

<210> SEQ ID NO 3
<211> LENGTH: 12
<212> TYPE: PRT
<213> ORGANISM: Homo sapiens
<220> FEATURE:
```

-continued

```
<221> NAME/KEY: MISC_FEATURE
<222> LOCATION: (1)..(1)
<223> OTHER INFORMATION: X = unknown

<400> SEQUENCE: 3

Xaa Ile Arg Phe Leu His Ser Phe Thr Met Tyr Lys
1               5                   10

<210> SEQ ID NO 4
<211> LENGTH: 380
<212> TYPE: PRT
<213> ORGANISM: Homo sapiens

<400> SEQUENCE: 4

Glu Thr Phe Pro Pro Lys Tyr Leu His Tyr Asp Glu Glu Thr Ser His
1               5                   10                  15

Gln Leu Leu Cys Asp Lys Cys Pro Gly Thr Tyr Leu Lys Gln His
            20                  25                  30

Cys Thr Ala Lys Trp Lys Thr Val Cys Ala Pro Cys Pro Asp His Tyr
        35                  40                  45

Tyr Thr Asp Ser Trp His Thr Ser Asp Glu Cys Leu Tyr Cys Ser Pro
    50                  55                  60

Val Cys Lys Glu Leu Gln Tyr Val Lys Gln Glu Cys Asn Arg Thr His
65                  70                  75                  80

Asn Arg Val Cys Glu Cys Lys Glu Gly Arg Tyr Leu Glu Ile Glu Phe
                85                  90                  95

Cys Leu Lys His Arg Ser Cys Pro Pro Gly Phe Gly Val Val Gln Ala
            100                 105                 110

Gly Thr Pro Glu Arg Asn Thr Val Cys Lys Arg Cys Pro Asp Gly Phe
        115                 120                 125

Phe Ser Asn Glu Thr Ser Ser Lys Ala Pro Cys Arg Lys His Thr Asn
    130                 135                 140

Cys Ser Val Phe Gly Leu Leu Leu Thr Gln Lys Gly Asn Ala Thr His
145                 150                 155                 160

Asp Asn Ile Cys Ser Gly Asn Ser Glu Ser Thr Gln Lys Cys Gly Ile
                165                 170                 175

Asp Val Thr Leu Cys Glu Glu Ala Phe Phe Arg Phe Ala Val Pro Thr
            180                 185                 190

Lys Phe Thr Pro Asn Trp Leu Ser Val Leu Val Asp Asn Leu Pro Gly
        195                 200                 205

Thr Lys Val Asn Ala Glu Ser Val Glu Arg Ile Lys Arg Gln His Ser
    210                 215                 220

Ser Gln Glu Gln Thr Phe Gln Leu Leu Lys Leu Trp Lys His Gln Asn
225                 230                 235                 240

Lys Asp Gln Asp Ile Val Lys Lys Ile Ile Gln Asp Ile Asp Leu Cys
                245                 250                 255

Glu Asn Ser Val Gln Arg His Ile Gly His Ala Asn Leu Thr Phe Glu
            260                 265                 270

Gln Leu Arg Ser Leu Met Glu Ser Leu Pro Gly Lys Lys Val Gly Ala
        275                 280                 285

Glu Asp Ile Glu Lys Thr Ile Lys Ala Cys Lys Pro Ser Asp Gln Ile
    290                 295                 300

Leu Lys Leu Leu Ser Leu Trp Arg Ile Lys Asn Gly Asp Gln Asp Thr
305                 310                 315                 320

Leu Lys Gly Leu Met His Ala Leu Lys His Ser Lys Thr Tyr His Phe
                325                 330                 335
```

-continued

```
Pro Lys Thr Val Thr Gln Ser Leu Lys Lys Thr Ile Arg Phe Leu His
            340                 345                 350

Ser Phe Thr Met Tyr Lys Leu Tyr Gln Lys Leu Phe Leu Glu Met Ile
            355                 360                 365

Gly Asn Gln Val Gln Ser Val Lys Ile Ser Cys Leu
            370                 375                 380

<210> SEQ ID NO 5
<211> LENGTH: 401
<212> TYPE: PRT
<213> ORGANISM: Homo sapiens

<400> SEQUENCE: 5

Met Asn Asn Leu Leu Cys Cys Ala Leu Val Phe Leu Asp Ile Ser Ile
1               5                   10                  15

Lys Trp Thr Thr Gln Glu Thr Phe Pro Pro Lys Tyr Leu His Tyr Asp
            20                  25                  30

Glu Glu Thr Ser His Gln Leu Leu Cys Asp Lys Cys Pro Pro Gly Thr
        35                  40                  45

Tyr Leu Lys Gln His Cys Thr Ala Lys Trp Lys Thr Val Cys Ala Pro
    50                  55                  60

Cys Pro Asp His Tyr Tyr Thr Asp Ser Trp His Thr Ser Asp Glu Cys
65                  70                  75                  80

Leu Tyr Cys Ser Pro Val Cys Lys Glu Leu Gln Tyr Val Lys Gln Glu
                85                  90                  95

Cys Asn Arg Thr His Asn Arg Val Cys Glu Cys Lys Glu Gly Arg Tyr
            100                 105                 110

Leu Glu Ile Glu Phe Cys Leu Lys His Arg Ser Cys Pro Pro Gly Phe
        115                 120                 125

Gly Val Val Gln Ala Gly Thr Pro Glu Arg Asn Thr Val Cys Lys Arg
    130                 135                 140

Cys Pro Asp Gly Phe Phe Ser Asn Glu Thr Ser Ser Lys Ala Pro Cys
145                 150                 155                 160

Arg Lys His Thr Asn Cys Ser Val Phe Gly Leu Leu Leu Thr Gln Lys
                165                 170                 175

Gly Asn Ala Thr His Asp Asn Ile Cys Ser Gly Asn Ser Glu Ser Thr
            180                 185                 190

Gln Lys Cys Gly Ile Asp Val Thr Leu Cys Glu Glu Ala Phe Phe Arg
        195                 200                 205

Phe Ala Val Pro Thr Lys Phe Thr Pro Asn Trp Leu Ser Val Leu Val
    210                 215                 220

Asp Asn Leu Pro Gly Thr Lys Val Asn Ala Glu Ser Val Glu Arg Ile
225                 230                 235                 240

Lys Arg Gln His Ser Ser Gln Glu Gln Thr Phe Gln Leu Leu Lys Leu
                245                 250                 255

Trp Lys His Gln Asn Lys Asp Gln Asp Ile Val Lys Lys Ile Ile Gln
            260                 265                 270

Asp Ile Asp Leu Cys Glu Asn Ser Val Gln Arg His Ile Gly His Ala
        275                 280                 285

Asn Leu Thr Phe Glu Gln Leu Arg Ser Leu Met Glu Ser Leu Pro Gly
    290                 295                 300

Lys Lys Val Gly Ala Glu Asp Ile Glu Lys Thr Ile Lys Ala Cys Lys
305                 310                 315                 320

Pro Ser Asp Gln Ile Leu Lys Leu Leu Ser Leu Trp Arg Ile Lys Asn
```

```
                   325                 330                 335
Gly Asp Gln Asp Thr Leu Lys Gly Leu Met His Ala Leu Lys His Ser
            340                 345                 350

Lys Thr Tyr His Phe Pro Lys Thr Val Thr Gln Ser Leu Lys Lys Thr
        355                 360                 365

Ile Arg Phe Leu His Ser Phe Thr Met Tyr Lys Leu Tyr Gln Lys Leu
    370                 375                 380

Phe Leu Glu Met Ile Gly Asn Gln Val Gln Ser Val Lys Ile Ser Cys
385                 390                 395                 400

Leu

<210> SEQ ID NO 6
<211> LENGTH: 1206
<212> TYPE: DNA
<213> ORGANISM: Homo sapiens

<400> SEQUENCE: 6
atgaacaact tgctgtgctg cgcgctcgtg tttctggaca tctccattaa gtggaccacc      60
caggaaacgt tcctccaaa gtaccttcat tatgacgaag aaacctctca tcagctgttg     120
tgtgacaaat gtcctcctgg tacctaccta aacaacact gtacagcaaa gtggaagacc     180
gtgtgcgccc cttgccctga ccactactac agacagcagc ggcacaccag tgacgagtgt     240
ctatactgca gccccgtgtg caaggagctg cagtacgtca gcaggagtg caatcgcacc     300 cacaaccgcg tgtgcgaatg caaggaaggg cgctaccttg agatagagtt ctgcttgaaa     360
cataggagct gccctcctgg atttggagtg gtgcaagctg aaccccaga gcgaaataca     420 gtttgcaaaa gatgtccaga tgggttcttc tcaaatgaga cgtcatctaa agcaccctgt     480
agaaaacaca caaattgcag tgtctttggt ctcctgctaa ctcagaaagg aaatgcaaca     540
cacgacaaca tatgttccgg aaacagtgaa tcaactcaaa atgtggaat agatgttacc     600 ctgtgtgagg aggcattct caggtttgct gttcctacaa agtttacgcc taactggctt     660
agtgtcttgg tagacaattt gcctggcacc aaagtaaacg cagagagtgt agagaggata     720
aaacggcaac acagctcaca agaacagact ttccagctgc tgaagttatg gaaacatcaa     780
aacaaagacc aagatatagt caagaagatc atccaagata ttgacctctg tgaaaacagc     840
gtgcagcggc acattggaca tgctaacctc accttcgagc agcttcgtag cttgatggaa     900
agcttaccgg gaaagaaagt gggagcagaa gacattgaaa aaacaataaa ggcatgcaaa     960
cccagtgacc agatcctgaa gctgctcagt ttgtggcgaa taaaaaatgg cgaccaagac    1020
accttgaagg gcctaatgca cgcactaaag cactcaaaga cgtaccactt tcccaaaact    1080
gtcactcaga gtcaaagaa gaccatcagg ttccttcaca gcttcacaat gtacaaattg    1140
tatcagaagt tatttttaga aatgataggt aaccaggtcc aatcagtaaa aataagctgc    1200
ttataa                                                              1206

<210> SEQ ID NO 7
<211> LENGTH: 15
<212> TYPE: PRT
<213> ORGANISM: Homo sapiens

<400> SEQUENCE: 7

Glu Thr Phe Pro Pro Lys Tyr Leu His Tyr Asp Glu Glu Thr Ser
1               5                  10                  15

<210> SEQ ID NO 8
```

<211> LENGTH: 1185
<212> TYPE: DNA
<213> ORGANISM: Homo sapiens

<400> SEQUENCE: 8

| | | | | | |
|---|---|---|---|---|---|
| atgaacaact | tgctgtgctg | cgcgctcgtg | tttctggaca | tctccattaa | gtggaccacc | 60 |
| caggaaacgt | tcctccaaa | gtaccttcat | tatgacgaag | aaacctctca | tcagctgttg | 120 |
| tgtgacaaat | gtcctcctgg | tacctaccta | aaacaacact | gtacagcaaa | gtggaagacc | 180 |
| gtgtgcgccc | cttgccctga | ccactactac | acagacagct | ggcacaccag | tgacgagtgt | 240 |
| ctatactgca | gccccgtgtg | caaggagtgc | aatcgcaccc | acaaccgcgt | gtgcgaatgc | 300 |
| aaggaagggc | gctaccttga | gatagagttc | tgcttgaaac | ataggagctg | ccctcctgga | 360 |
| tttggagtgg | tgcaagctgg | aaccccagag | cgaaatacag | tttgcaaaag | atgtccagat | 420 |
| gggttcttct | caaatgagac | gtcatctaaa | gcaccctgta | gaaaacacac | aaattgcagt | 480 |
| gtctttggtc | tcctgctaac | tcagaaagga | atgcaacac | acgacaacat | atgttccgga | 540 |
| aacagtgaat | caactcaaaa | atgtggaata | gatgttaccc | tgtgtgagga | ggcattcttc | 600 |
| aggtttgctg | ttcctacaaa | gtttacgcct | aactggctta | gtgtcttggt | agacaatttg | 660 |
| cctggcacca | agtaaacgc | agagagtgta | gagaggataa | acggcaaca | cagctcacaa | 720 |
| gaacagactt | tccagctgct | gaagttatgg | aaacatcaaa | acaaagacca | agatatagtc | 780 |
| aagaagatca | tccaagatat | tgacctctgt | gaaaacagcg | tgcagcggca | cattggacat | 840 |
| gctaacctca | ccttcgagca | gcttcgtagc | ttgatggaaa | gcttaccggg | aagaaagtg | 900 |
| ggagcagaag | acattgaaaa | aacaataaag | gcatgcaaac | ccagtgacca | gatcctgaag | 960 |
| ctgctcagtt | tgtggcgaat | aaaaaatggc | gaccaagaca | ccttgaaggg | cctaatgcac | 1020 |
| gcactaaagc | actcaaagac | gtaccacttt | cccaaaactg | tcactcagag | tctaaagaag | 1080 |
| accatcaggt | tccttcacag | cttcacaatg | tacaaattgt | atcagaagtt | atttttagaa | 1140 |
| atgataggta | accaggtcca | atcagtaaaa | ataagctgct | tataa | | 1185 |

<210> SEQ ID NO 9
<211> LENGTH: 394
<212> TYPE: PRT
<213> ORGANISM: Homo sapiens

<400> SEQUENCE: 9

Met Asn Asn Leu Leu Cys Cys Ala Leu Val Phe Leu Asp Ile Ser Ile
1               5                   10                  15

Lys Trp Thr Thr Gln Glu Thr Phe Pro Pro Lys Tyr Leu His Tyr Asp
            20                  25                  30

Glu Glu Thr Ser His Gln Leu Leu Cys Asp Lys Cys Pro Pro Gly Thr
        35                  40                  45

Tyr Leu Lys Gln His Cys Thr Ala Lys Trp Lys Thr Val Cys Ala Pro
    50                  55                  60

Cys Pro Asp His Tyr Tyr Thr Asp Ser Trp His Thr Ser Asp Glu Cys
65                  70                  75                  80

Leu Tyr Cys Ser Pro Val Cys Lys Glu Cys Asn Arg Thr His Asn Arg
                85                  90                  95

Val Cys Glu Cys Lys Glu Gly Arg Tyr Leu Glu Ile Glu Phe Cys Leu
            100                 105                 110

Lys His Arg Ser Cys Pro Pro Gly Phe Gly Val Val Gln Ala Gly Thr
        115                 120                 125

Pro Glu Arg Asn Thr Val Cys Lys Arg Cys Pro Asp Gly Phe Phe Ser

```
                130                 135                 140
Asn Glu Thr Ser Ser Lys Ala Pro Cys Arg Lys His Thr Asn Cys Ser
145                 150                 155                 160

Val Phe Gly Leu Leu Leu Thr Gln Lys Gly Asn Ala Thr His Asp Asn
                165                 170                 175

Ile Cys Ser Gly Asn Ser Glu Ser Thr Gln Lys Cys Gly Ile Asp Val
                180                 185                 190

Thr Leu Cys Glu Glu Ala Phe Phe Arg Phe Ala Val Pro Thr Lys Phe
                195                 200                 205

Thr Pro Asn Trp Leu Ser Val Leu Val Asp Asn Leu Pro Gly Thr Lys
                210                 215                 220

Val Asn Ala Glu Ser Val Glu Arg Ile Lys Arg Gln His Ser Ser Gln
225                 230                 235                 240

Glu Gln Thr Phe Gln Leu Leu Lys Leu Trp Lys His Gln Asn Lys Asp
                245                 250                 255

Gln Asp Ile Val Lys Lys Ile Ile Gln Asp Ile Asp Leu Cys Glu Asn
                260                 265                 270

Ser Val Gln Arg His Ile Gly His Ala Asn Leu Thr Phe Glu Gln Leu
                275                 280                 285

Arg Ser Leu Met Glu Ser Leu Pro Gly Lys Lys Val Gly Ala Glu Asp
                290                 295                 300

Ile Glu Lys Thr Ile Lys Ala Cys Lys Pro Ser Asp Gln Ile Leu Lys
305                 310                 315                 320

Leu Leu Ser Leu Trp Arg Ile Lys Asn Gly Asp Gln Asp Thr Leu Lys
                325                 330                 335

Gly Leu Met His Ala Leu Lys His Ser Lys Thr Tyr His Phe Pro Lys
                340                 345                 350

Thr Val Thr Gln Ser Leu Lys Lys Thr Ile Arg Phe Leu His Ser Phe
                355                 360                 365

Thr Met Tyr Lys Leu Tyr Gln Lys Leu Phe Leu Glu Met Ile Gly Asn
                370                 375                 380

Gln Val Gln Ser Val Lys Ile Ser Cys Leu
385                 390

<210> SEQ ID NO 10
<211> LENGTH: 1089
<212> TYPE: DNA
<213> ORGANISM: Homo sapiens

<400> SEQUENCE: 10
atgaacaagt tgctgtgctg cgcgctcgtg tttctggaca tctccattaa gtggaccacc      60
caggaaacgt ttcctccaaa gtaccttcat tatgacgaag aaacctctca tcagctgttg     120
tgtgacaaat gtcctcctgg tacctaccta aacaacact gtacagcaaa gtggaagacc      180
gtgtgcgccc cttgccctga ccactactac acagacagct ggcacaccag tgacgagtgt     240
ctatactgca gccccgtgtg caaggagctg cagtacgtca gcaggagtg caatcgcacc      300 cacaaccgcg tgtgcgaatg caaggaaggg cgctaccttg agatagagtt ctgcttgaaa     360
cataggagct gccctcctgg atttggagtg gtgcaagctg aaccccaga gcgaaataca      420 gtttgcaaaa gatgtccaga tgggttcttc tcaaatgaga cgtcatctaa gcaccctgt      480 agaaaacaca caaattgcag tgtctttggt ctcctgctaa ctcagaaagg aaatgcaaca     540
cacgacaaca tatgttccgg aaacagtgaa tcaactcaaa aatgtggaat agatgttacc     600
ctgtgtgagg aggcattctt caggtttgct gttcctacaa agtttacgcc taactggctt     660
```

```
agtgtcttgg tagacaattt gcctggcacc aaagtaaacg cagagagtgt agagaggata      720
aaacggcaac acagctcaca agaacagact ttccagctgc tgaagttatg aaacatcaa       780 aacaaagacc aagatatagt caagaagatc atccaagata ttgacctctg tgaaaacagc      840
gtgcagcggc acattggaca tgctaacctc agtttgtggc gaataaaaaa tggcgaccaa      900
gacaccttga agggcctaat gcacgcacta aagcactcaa agacgtacca ctttcccaaa      960
actgtcactc agagtctaaa gaagaccatc aggttccttc acagcttcac aatgtacaaa     1020
ttgtatcaga agttattttt agaaatgata ggtaaccagg tccaatcagt aaaaataagc     1080
tgcttataa                                                             1089
```

<210> SEQ ID NO 11
<211> LENGTH: 362
<212> TYPE: PRT
<213> ORGANISM: Homo sapiens

<400> SEQUENCE: 11

```
Met Asn Lys Leu Leu Cys Cys Ala Leu Val Phe Leu Asp Ile Ser Ile
1               5                   10                  15

Lys Trp Thr Thr Gln Glu Thr Phe Pro Pro Lys Tyr Leu His Tyr Asp
            20                  25                  30

Glu Glu Thr Ser His Gln Leu Leu Cys Asp Lys Cys Pro Pro Gly Thr
        35                  40                  45

Tyr Leu Lys Gln His Cys Thr Ala Lys Trp Lys Thr Val Cys Ala Pro
    50                  55                  60

Cys Pro Asp His Tyr Tyr Thr Asp Ser Trp His Thr Ser Asp Glu Cys
65                  70                  75                  80

Leu Tyr Cys Ser Pro Val Cys Lys Glu Leu Gln Tyr Val Lys Gln Glu
                85                  90                  95

Cys Asn Arg Thr His Asn Arg Val Cys Glu Cys Lys Glu Gly Arg Tyr
            100                 105                 110

Leu Glu Ile Glu Phe Cys Leu Lys His Arg Ser Cys Pro Pro Gly Phe
        115                 120                 125

Gly Val Val Gln Ala Gly Thr Pro Glu Arg Asn Thr Val Cys Lys Arg
    130                 135                 140

Cys Pro Asp Gly Phe Phe Ser Asn Glu Thr Ser Ser Lys Ala Pro Cys
145                 150                 155                 160

Arg Lys His Thr Asn Cys Ser Val Phe Gly Leu Leu Leu Thr Gln Lys
                165                 170                 175

Gly Asn Ala Thr His Asp Asn Ile Cys Ser Gly Asn Ser Glu Ser Thr
            180                 185                 190

Gln Lys Cys Gly Ile Asp Val Thr Leu Cys Glu Glu Ala Phe Phe Arg
        195                 200                 205

Phe Ala Val Pro Thr Lys Phe Thr Pro Asn Trp Leu Ser Val Leu Val
    210                 215                 220

Asp Asn Leu Pro Gly Thr Lys Val Asn Ala Glu Ser Val Glu Arg Ile
225                 230                 235                 240

Lys Arg Gln His Ser Ser Gln Glu Gln Thr Phe Gln Leu Leu Lys Leu
                245                 250                 255

Trp Lys His Gln Asn Lys Asp Gln Asp Ile Val Lys Lys Ile Ile Gln
            260                 265                 270

Asp Ile Asp Leu Cys Glu Asn Ser Val Gln Arg His Ile Gly His Ala
        275                 280                 285
```

```
Asn Leu Ser Leu Trp Arg Ile Lys Asn Gly Asp Gln Asp Thr Leu Lys
    290                 295                 300

Gly Leu Met His Ala Leu Lys His Ser Lys Thr Tyr His Phe Pro Lys
305                 310                 315                 320

Thr Val Thr Gln Ser Leu Lys Lys Thr Ile Arg Phe Leu His Ser Phe
                325                 330                 335

Thr Met Tyr Lys Leu Tyr Gln Lys Leu Phe Leu Glu Met Ile Gly Asn
            340                 345                 350

Gln Val Gln Ser Val Lys Ile Ser Cys Leu
        355                 360
```

<210> SEQ ID NO 12
<211> LENGTH: 465
<212> TYPE: DNA
<213> ORGANISM: Homo sapiens

<400> SEQUENCE: 12

```
atgaacaagt tgctgtgctg ctcgctcgtg tttctggaca tctccattaa gtggaccacc      60
caggaaacgt tcctccaaa gtaccttcat tatgacgaag aaacctctca tcagctgttg     120
tgtgacaaat gtcctcctgg tacctaccta aacaacact gtacagcaaa gtggaagacc     180
gtgtgcgccc cttgccctga ccactactac acagacagct ggcacaccag tgacgagtgt     240
ctatactgca gccccgtgtg caaggagctg cagtacgtca gcaggagtg caatcgcacc     300
cacaaccgcg tgtgcgaatg caaggaaggg cgctaccttg agatagagtt ctgcttgaaa     360
cataggagct gccctcctgg atttggagtg gtgcaagctg gtacgtgtca atgtgcagca     420
aaattaatta ggatcatgca agtcagata gttgtgacag tttag                     465
```

<210> SEQ ID NO 13
<211> LENGTH: 154
<212> TYPE: PRT
<213> ORGANISM: Homo sapiens

<400> SEQUENCE: 13

```
Met Asn Lys Leu Leu Cys Cys Ser Leu Val Phe Leu Asp Ile Ser Ile
1               5                   10                  15

Lys Trp Thr Thr Gln Glu Thr Phe Pro Pro Lys Tyr Leu His Tyr Asp
            20                  25                  30

Glu Glu Thr Ser His Gln Leu Leu Cys Asp Lys Cys Pro Pro Gly Thr
        35                  40                  45

Tyr Leu Lys Gln His Cys Thr Ala Lys Trp Lys Thr Val Cys Ala Pro
    50                  55                  60

Cys Pro Asp His Tyr Tyr Thr Asp Ser Trp His Thr Ser Asp Glu Cys
65                  70                  75                  80

Leu Tyr Cys Ser Pro Val Cys Lys Glu Leu Gln Tyr Val Lys Gln Glu
                85                  90                  95

Cys Asn Arg Thr His Asn Arg Val Cys Glu Cys Lys Glu Gly Arg Tyr
            100                 105                 110

Leu Glu Ile Glu Phe Cys Leu Lys His Arg Ser Cys Pro Pro Gly Phe
        115                 120                 125

Gly Val Val Gln Ala Gly Thr Cys Gln Cys Ala Ala Lys Leu Ile Arg
    130                 135                 140

Ile Met Gln Ser Gln Ile Val Val Thr Val
145                 150
```

<210> SEQ ID NO 14

```
<211> LENGTH: 438
<212> TYPE: DNA
<213> ORGANISM: Homo sapiens

<400> SEQUENCE: 14
atgaacaagt tgctgtgctg cgcgctcgtg tttctggaca tctccattaa gtggaccacc      60
caggaaacgt tcctccaaa gtaccttcat tatgacgaag aaacctctca tcagctgttg      120
tgtgacaaat gtcctcctgg tacctaccta aaacaacact gtacagcaaa gtggaagacc      180
gtgtgcgccc cttgccctga ccactactac acagacagct ggcacaccag tgacgagtgt      240
ctatactgca gccccgtgtg caaggagctg cagtacgtca agcaggagtg caatcgcacc      300
cacaaccgcg tgtgcgaatg caaggaaggg cgctaccttg agatagagtt ctgcttgaaa      360
cataggagct gccctcctgg atttggagtg gtgcaagctg gatgcaggag aagacccaag      420
ccacagatat gtatctga                                                    438

<210> SEQ ID NO 15
<211> LENGTH: 145
<212> TYPE: PRT
<213> ORGANISM: Homo sapiens

<400> SEQUENCE: 15

Met Asn Lys Leu Leu Cys Cys Ala Leu Val Phe Leu Asp Ile Ser Ile
1               5                   10                  15

Lys Trp Thr Thr Gln Glu Thr Phe Pro Pro Lys Tyr Leu His Tyr Asp
            20                  25                  30

Glu Glu Thr Ser His Gln Leu Leu Cys Asp Lys Cys Pro Pro Gly Thr
        35                  40                  45

Tyr Leu Lys Gln His Cys Thr Ala Lys Trp Lys Thr Val Cys Ala Pro
    50                  55                  60

Cys Pro Asp His Tyr Tyr Thr Asp Ser Trp His Thr Ser Asp Glu Cys
65                  70                  75                  80

Leu Tyr Cys Ser Pro Val Cys Lys Glu Leu Gln Tyr Val Lys Gln Glu
                85                  90                  95

Cys Asn Arg Thr His Asn Arg Val Cys Glu Cys Lys Glu Gly Arg Tyr
            100                 105                 110

Leu Glu Ile Glu Phe Cys Leu Lys His Arg Ser Cys Pro Pro Gly Phe
        115                 120                 125

Gly Val Val Gln Ala Gly Cys Arg Arg Arg Pro Lys Pro Gln Ile Cys
    130                 135                 140

Ile
145

<210> SEQ ID NO 16
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 16
aattaaccct cactaaaggg                                                   20

<210> SEQ ID NO 17
<211> LENGTH: 22
<212> TYPE: DNA
<213> ORGANISM: Artificial Sequence
<220> FEATURE:
<223> OTHER INFORMATION: Synthetic Sequence
```

```
<400> SEQUENCE: 17
gtaatacgac tcactatagg gc                                    22

<210> SEQ ID NO 18
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 18
acatcaaaac aaagaccaag                                       20

<210> SEQ ID NO 19
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 19
tcttggtctt tgttttgatg                                       20

<210> SEQ ID NO 20
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 20
ttattcgcca caaactgagc                                       20

<210> SEQ ID NO 21
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 21
ttgtgaagct gtgaaggaac                                       20

<210> SEQ ID NO 22
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 22
gctcagtttg tggcgaataa                                       20

<210> SEQ ID NO 23
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 23
gtgggagcag aagacattga                                       20

<210> SEQ ID NO 24
```

```
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 24
aatgaacaac ttgctgtgct                                              20

<210> SEQ ID NO 25
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 25
tgacaaatgt cctcctggta                                              20

<210> SEQ ID NO 26
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 26
aggtaggtac caggaggaca                                              20

<210> SEQ ID NO 27
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 27
gagctgccct cctggatttg                                              20

<210> SEQ ID NO 28
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 28
caaactgtat ttcgctctgg                                              20

<210> SEQ ID NO 29
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 29
gtgtgaggag gcattcttca                                              20

<210> SEQ ID NO 30
<211> LENGTH: 32
<212> TYPE: DNA
<213> ORGANISM: Artificial Sequence
<220> FEATURE:
<223> OTHER INFORMATION: Synthetic Sequence

<400> SEQUENCE: 30
```

-continued gaatcaactc aaaaaagtgg aatagatgtt ac                32

<210> SEQ ID NO 31
<211> LENGTH: 32
<212> TYPE: DNA
<213> ORGANISM: Artificial Sequence
<220> FEATURE:
<223> OTHER INFORMATION: Synthetic Sequence

<400> SEQUENCE: 31
gtaacatcta ttccactttt ttgagttgat tc                32

<210> SEQ ID NO 32
<211> LENGTH: 30
<212> TYPE: DNA
<213> ORGANISM: Artificial Sequence
<220> FEATURE:
<223> OTHER INFORMATION: Synthetic Sequence

<400> SEQUENCE: 32
atagatgtta ccctgagtga ggaggcattc                   30

<210> SEQ ID NO 33
<211> LENGTH: 30
<212> TYPE: DNA
<213> ORGANISM: Artificial Sequence
<220> FEATURE:
<223> OTHER INFORMATION: Synthetic Sequence

<400> SEQUENCE: 33
gaatgcctcc tcactcaggg taacatctat                   30

<210> SEQ ID NO 34
<211> LENGTH: 31
<212> TYPE: DNA
<213> ORGANISM: Artificial Sequence
<220> FEATURE:
<223> OTHER INFORMATION: Synthetic Sequence

<400> SEQUENCE: 34
caagatattg acctcagtga aaacagcgtg c                 31

<210> SEQ ID NO 35
<211> LENGTH: 31
<212> TYPE: DNA
<213> ORGANISM: Artificial Sequence
<220> FEATURE:
<223> OTHER INFORMATION: Synthetic Sequence

<400> SEQUENCE: 35
gcacgctgtt ttcactgagg gcaatatctt g                 31

<210> SEQ ID NO 36
<211> LENGTH: 31
<212> TYPE: DNA
<213> ORGANISM: Artificial Sequence
<220> FEATURE:
<223> OTHER INFORMATION: Synthetic Sequence

<400> SEQUENCE: 36
aaaacaataa aggcaagcaa acccagtgac c                 31

<210> SEQ ID NO 37
<211> LENGTH: 31
<212> TYPE: DNA

```
<213> ORGANISM: Artificial Sequence
<220> FEATURE:
<223> OTHER INFORMATION: Synthetic Sequence

<400> SEQUENCE: 37
ggtcactggg tttgcttgcc tttattgttt t                                   31

<210> SEQ ID NO 38
<211> LENGTH: 31
<212> TYPE: DNA
<213> ORGANISM: Artificial Sequence
<220> FEATURE:
<223> OTHER INFORMATION: Synthetic Sequence

<400> SEQUENCE: 38
tcagtaaaaa taagcagctt ataactggcc a                                   31

<210> SEQ ID NO 39
<211> LENGTH: 31
<212> TYPE: DNA
<213> ORGANISM: Artificial Sequence
<220> FEATURE:
<223> OTHER INFORMATION: Synthetic Sequence

<400> SEQUENCE: 39
tggccagtta taagctgctt atttttactg a                                   31

<210> SEQ ID NO 40
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 40
ttggggttta ttggaggaga tg                                             22

<210> SEQ ID NO 41
<211> LENGTH: 36
<212> TYPE: DNA
<213> ORGANISM: Artificial Sequence
<220> FEATURE:
<223> OTHER INFORMATION: Synthetic Sequence

<400> SEQUENCE: 41
accacccagg aaccttgccc tgaccactac tacaca                              36

<210> SEQ ID NO 42
<211> LENGTH: 36
<212> TYPE: DNA
<213> ORGANISM: Artificial Sequence
<220> FEATURE:
<223> OTHER INFORMATION: Synthetic Sequence

<400> SEQUENCE: 42
gtcagggcaa ggttcctggg tggtccactt aatgga                              36

<210> SEQ ID NO 43
<211> LENGTH: 36
<212> TYPE: DNA
<213> ORGANISM: Artificial Sequence
<220> FEATURE:
<223> OTHER INFORMATION: Synthetic Sequence

<400> SEQUENCE: 43
accgtgtgcg ccgaatgcaa ggaagggcgc tacctt                              36
```

<210> SEQ ID NO 44
<211> LENGTH: 36
<212> TYPE: DNA
<213> ORGANISM: Artificial Sequence
<220> FEATURE:
<223> OTHER INFORMATION: Synthetic Sequence

<400> SEQUENCE: 44
ttccttgcat tcggcgcaca cggtcttcca ctttgc                    36

<210> SEQ ID NO 45
<211> LENGTH: 36
<212> TYPE: DNA
<213> ORGANISM: Artificial Sequence
<220> FEATURE:
<223> OTHER INFORMATION: Synthetic Sequence

<400> SEQUENCE: 45
aaccgcgtgt gcagatgtcc agatgggttc ttctca                    36

<210> SEQ ID NO 46
<211> LENGTH: 36
<212> TYPE: DNA
<213> ORGANISM: Artificial Sequence
<220> FEATURE:
<223> OTHER INFORMATION: Synthetic Sequence

<400> SEQUENCE: 46
atctggacat ctgcacacgc ggttgtgggt gcgatt                    36

<210> SEQ ID NO 47
<211> LENGTH: 36
<212> TYPE: DNA
<213> ORGANISM: Artificial Sequence
<220> FEATURE:
<223> OTHER INFORMATION: Synthetic Sequence

<400> SEQUENCE: 47
acagtttgca aatccggaaa cagtgaatca actcaa                    36

<210> SEQ ID NO 48
<211> LENGTH: 36
<212> TYPE: DNA
<213> ORGANISM: Artificial Sequence
<220> FEATURE:
<223> OTHER INFORMATION: Synthetic Sequence

<400> SEQUENCE: 48
actgtttccg gatttgcaaa ctgtatttcg ctctgg                    36

<210> SEQ ID NO 49
<211> LENGTH: 36
<212> TYPE: DNA
<213> ORGANISM: Artificial Sequence
<220> FEATURE:
<223> OTHER INFORMATION: Synthetic Sequence

<400> SEQUENCE: 49
aatgtggaat agatattgac ctctgtgaaa acagcg                    36

<210> SEQ ID NO 50
<211> LENGTH: 36
<212> TYPE: DNA
<213> ORGANISM: Artificial Sequence
<220> FEATURE:

<223> OTHER INFORMATION: Synthetic Sequence

<400> SEQUENCE: 50
agaggtcaat atctattcca cattttgag ttgatt                36

<210> SEQ ID NO 51
<211> LENGTH: 36
<212> TYPE: DNA
<213> ORGANISM: Artificial Sequence
<220> FEATURE:
<223> OTHER INFORMATION: Synthetic Sequence

<400> SEQUENCE: 51
agatcatcca agacgcacta aagcactcaa agacgt                36

<210> SEQ ID NO 52
<211> LENGTH: 36
<212> TYPE: DNA
<213> ORGANISM: Artificial Sequence
<220> FEATURE:
<223> OTHER INFORMATION: Synthetic Sequence

<400> SEQUENCE: 52
gctttagtgc gtcttggatg atcttcttga ctatat                36

<210> SEQ ID NO 53
<211> LENGTH: 29
<212> TYPE: DNA
<213> ORGANISM: Artificial Sequence
<220> FEATURE:
<223> OTHER INFORMATION: Synthetic Sequence

<400> SEQUENCE: 53
ggctcgagcg cccagccgcc gcctccaag                29

<210> SEQ ID NO 54
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 54
tttgagtgct ttagtgcgtg                20

<210> SEQ ID NO 55
<211> LENGTH: 30
<212> TYPE: DNA
<213> ORGANISM: Artificial Sequence
<220> FEATURE:
<223> OTHER INFORMATION: Synthetic Sequence

<400> SEQUENCE: 55
tcagtaaaaa taagctaact ggaaatggcc                30

<210> SEQ ID NO 56
<211> LENGTH: 30
<212> TYPE: DNA
<213> ORGANISM: Artificial Sequence
<220> FEATURE:
<223> OTHER INFORMATION: Synthetic Sequence

<400> SEQUENCE: 56
ggccatttcc agttagctta ttttactga                30

```
<210> SEQ ID NO 57
<211> LENGTH: 29
<212> TYPE: DNA
<213> ORGANISM: Artificial Sequence
<220> FEATURE:
<223> OTHER INFORMATION: Synthetic Sequence

<400> SEQUENCE: 57
ccggatcctc agtgctttag tgcgtgcat                              29

<210> SEQ ID NO 58
<211> LENGTH: 29
<212> TYPE: DNA
<213> ORGANISM: Artificial Sequence
<220> FEATURE:
<223> OTHER INFORMATION: Synthetic Sequence

<400> SEQUENCE: 58
ccggatcctc attggatgat cttcttgac                              29

<210> SEQ ID NO 59
<211> LENGTH: 29
<212> TYPE: DNA
<213> ORGANISM: Artificial Sequence
<220> FEATURE:
<223> OTHER INFORMATION: Synthetic Sequence

<400> SEQUENCE: 59
ccggatcctc atattccaca ttttgagt                               29

<210> SEQ ID NO 60
<211> LENGTH: 29
<212> TYPE: DNA
<213> ORGANISM: Artificial Sequence
<220> FEATURE:
<223> OTHER INFORMATION: Synthetic Sequence

<400> SEQUENCE: 60
ccggatcctc atttgcaaac tgtatttcg                              29

<210> SEQ ID NO 61
<211> LENGTH: 29
<212> TYPE: DNA
<213> ORGANISM: Artificial Sequence
<220> FEATURE:
<223> OTHER INFORMATION: Synthetic Sequence

<400> SEQUENCE: 61
ccggatcctc attcgcacac gcggttgtg                              29

<210> SEQ ID NO 62
<211> LENGTH: 401
<212> TYPE: PRT
<213> ORGANISM: Homo sapiens

<400> SEQUENCE: 62

Met Asn Asn Leu Leu Cys Cys Ala Leu Val Phe Leu Asp Ile Ser Ile
1               5                   10                  15

Lys Trp Thr Thr Gln Glu Thr Phe Pro Pro Lys Tyr Leu His Tyr Asp
            20                  25                  30

Glu Glu Thr Ser His Gln Leu Leu Cys Asp Lys Cys Pro Pro Gly Thr
        35                  40                  45

Tyr Leu Lys Gln His Cys Thr Ala Lys Trp Lys Thr Val Cys Ala Pro
    50                  55                  60
```

Cys Pro Asp His Tyr Tyr Thr Asp Ser Trp His Thr Ser Asp Glu Cys
 65                  70                  75                  80

Leu Tyr Cys Ser Pro Val Cys Lys Glu Leu Gln Tyr Val Lys Gln Glu
                 85                  90                  95

Cys Asn Arg Thr His Asn Arg Val Cys Glu Cys Lys Glu Gly Arg Tyr
            100                 105                 110

Leu Glu Ile Glu Phe Cys Leu Lys His Arg Ser Cys Pro Pro Gly Phe
        115                 120                 125

Gly Val Val Gln Ala Gly Thr Pro Glu Arg Asn Thr Val Cys Lys Arg
    130                 135                 140

Cys Pro Asp Gly Phe Phe Ser Asn Glu Thr Ser Ser Lys Ala Pro Cys
145                 150                 155                 160

Arg Lys His Thr Asn Cys Ser Val Phe Gly Leu Leu Leu Thr Gln Lys
                165                 170                 175

Gly Asn Ala Thr His Asp Asn Ile Cys Ser Gly Asn Ser Glu Ser Thr
            180                 185                 190

Gln Lys Ser Gly Ile Asp Val Thr Leu Cys Glu Glu Ala Phe Phe Arg
        195                 200                 205

Phe Ala Val Pro Thr Lys Phe Thr Pro Asn Trp Leu Ser Val Leu Val
    210                 215                 220

Asp Asn Leu Pro Gly Thr Lys Val Asn Ala Glu Ser Val Glu Arg Ile
225                 230                 235                 240

Lys Arg Gln His Ser Ser Gln Glu Gln Thr Phe Gln Leu Leu Lys Leu
                245                 250                 255

Trp Lys His Gln Asn Lys Asp Gln Asp Ile Val Lys Lys Ile Ile Gln
            260                 265                 270

Asp Ile Asp Leu Cys Glu Asn Ser Val Gln Arg His Ile Gly His Ala
        275                 280                 285

Asn Leu Thr Phe Glu Gln Leu Arg Ser Leu Met Glu Ser Leu Pro Gly
    290                 295                 300

Lys Lys Val Gly Ala Glu Asp Ile Glu Lys Thr Ile Lys Ala Cys Lys
305                 310                 315                 320

Pro Ser Asp Gln Ile Leu Lys Leu Leu Ser Leu Trp Arg Ile Lys Asn
                325                 330                 335

Gly Asp Gln Asp Thr Leu Lys Gly Leu Met His Ala Leu Lys His Ser
            340                 345                 350

Lys Thr Tyr His Phe Pro Lys Thr Val Thr Gln Ser Leu Lys Lys Thr
        355                 360                 365

Ile Arg Phe Leu His Ser Phe Thr Met Tyr Lys Leu Tyr Gln Lys Leu
    370                 375                 380

Phe Leu Glu Met Ile Gly Asn Gln Val Gln Ser Val Lys Ile Ser Cys
385                 390                 395                 400

Leu

<210> SEQ ID NO 63
<211> LENGTH: 401
<212> TYPE: PRT
<213> ORGANISM: Homo sapiens

<400> SEQUENCE: 63

Met Asn Asn Leu Leu Cys Cys Ala Leu Val Phe Leu Asp Ile Ser Ile
1               5                   10                  15

Lys Trp Thr Thr Gln Glu Thr Phe Pro Pro Lys Tyr Leu His Tyr Asp
            20                  25                  30

```
Glu Glu Thr Ser His Gln Leu Leu Cys Asp Lys Cys Pro Pro Gly Thr
             35                  40                  45

Tyr Leu Lys Gln His Cys Thr Ala Lys Trp Lys Thr Val Cys Ala Pro
         50                  55                  60

Cys Pro Asp His Tyr Tyr Thr Asp Ser Trp His Thr Ser Asp Glu Cys
 65                  70                  75                  80

Leu Tyr Cys Ser Pro Val Cys Lys Glu Leu Gln Tyr Val Lys Gln Glu
                 85                  90                  95

Cys Asn Arg Thr His Asn Arg Val Cys Glu Cys Lys Glu Gly Arg Tyr
             100                 105                 110

Leu Glu Ile Glu Phe Cys Leu Lys His Arg Ser Cys Pro Pro Gly Phe
         115                 120                 125

Gly Val Val Gln Ala Gly Thr Pro Glu Arg Asn Thr Val Cys Lys Arg
130                 135                 140

Cys Pro Asp Gly Phe Phe Ser Asn Glu Thr Ser Ser Lys Ala Pro Cys
145                 150                 155                 160

Arg Lys His Thr Asn Cys Ser Val Phe Gly Leu Leu Leu Thr Gln Lys
                 165                 170                 175

Gly Asn Ala Thr His Asp Asn Ile Cys Ser Gly Asn Ser Glu Ser Thr
             180                 185                 190

Gln Lys Cys Gly Ile Asp Val Thr Leu Ser Glu Glu Ala Phe Phe Arg
         195                 200                 205

Phe Ala Val Pro Thr Lys Phe Thr Pro Asn Trp Leu Ser Val Leu Val
         210                 215                 220

Asp Asn Leu Pro Gly Thr Lys Val Asn Ala Glu Ser Val Glu Arg Ile
225                 230                 235                 240

Lys Arg Gln His Ser Ser Gln Glu Gln Thr Phe Gln Leu Leu Lys Leu
                 245                 250                 255

Trp Lys His Gln Asn Lys Asp Gln Asp Ile Val Lys Lys Ile Ile Gln
             260                 265                 270

Asp Ile Asp Leu Cys Glu Asn Ser Val Gln Arg His Ile Gly His Ala
         275                 280                 285

Asn Leu Thr Phe Glu Gln Leu Arg Ser Leu Met Glu Ser Leu Pro Gly
         290                 295                 300

Lys Lys Val Gly Ala Glu Asp Ile Glu Lys Thr Ile Lys Ala Cys Lys
305                 310                 315                 320

Pro Ser Asp Gln Ile Leu Lys Leu Leu Ser Leu Trp Arg Ile Lys Asn
                 325                 330                 335

Gly Asp Gln Asp Thr Leu Lys Gly Leu Met His Ala Leu Lys His Ser
             340                 345                 350

Lys Thr Tyr His Phe Pro Lys Thr Val Thr Gln Ser Leu Lys Lys Thr
         355                 360                 365

Ile Arg Phe Leu His Ser Phe Thr Met Tyr Lys Leu Tyr Gln Lys Leu
370                 375                 380

Phe Leu Glu Met Ile Gly Asn Gln Val Gln Ser Val Lys Ile Ser Cys
385                 390                 395                 400

Leu

<210> SEQ ID NO 64
<211> LENGTH: 401
<212> TYPE: PRT
<213> ORGANISM: Homo sapiens

<400> SEQUENCE: 64
```

```
Met Asn Asn Leu Leu Cys Cys Ala Leu Val Phe Leu Asp Ile Ser Ile
1               5                   10                  15

Lys Trp Thr Thr Gln Glu Thr Phe Pro Pro Lys Tyr Leu His Tyr Asp
            20                  25                  30

Glu Glu Thr Ser His Gln Leu Leu Cys Asp Lys Cys Pro Pro Gly Thr
        35                  40                  45

Tyr Leu Lys Gln His Cys Thr Ala Lys Trp Lys Thr Val Cys Ala Pro
    50                  55                  60

Cys Pro Asp His Tyr Tyr Thr Asp Ser Trp His Thr Ser Asp Glu Cys
65              70                  75                  80

Leu Tyr Cys Ser Pro Val Cys Lys Glu Leu Gln Tyr Val Lys Gln Glu
                85                  90                  95

Cys Asn Arg Thr His Asn Arg Val Cys Glu Cys Lys Glu Gly Arg Tyr
            100                 105                 110

Leu Glu Ile Glu Phe Cys Leu Lys His Arg Ser Cys Pro Pro Gly Phe
        115                 120                 125

Gly Val Val Gln Ala Gly Thr Pro Glu Arg Asn Thr Val Cys Lys Arg
    130                 135                 140

Cys Pro Asp Gly Phe Phe Ser Asn Glu Thr Ser Ser Lys Ala Pro Cys
145                 150                 155                 160

Arg Lys His Thr Asn Cys Ser Val Phe Gly Leu Leu Leu Thr Gln Lys
            165                 170                 175

Gly Asn Ala Thr His Asp Asn Ile Cys Ser Gly Asn Ser Glu Ser Thr
        180                 185                 190

Gln Lys Cys Gly Ile Asp Val Thr Leu Cys Glu Glu Ala Phe Phe Arg
    195                 200                 205

Phe Ala Val Pro Thr Lys Phe Thr Pro Asn Trp Leu Ser Val Leu Val
210                 215                 220

Asp Asn Leu Pro Gly Thr Lys Val Asn Ala Glu Ser Val Glu Arg Ile
225                 230                 235                 240

Lys Arg Gln His Ser Ser Gln Glu Gln Thr Phe Gln Leu Leu Lys Leu
            245                 250                 255

Trp Lys His Gln Asn Lys Asp Gln Asp Ile Val Lys Lys Ile Ile Gln
        260                 265                 270

Asp Ile Asp Leu Ser Glu Asn Ser Val Gln Arg His Ile Gly His Ala
    275                 280                 285

Asn Leu Thr Phe Glu Gln Leu Arg Ser Leu Met Glu Ser Leu Pro Gly
290                 295                 300

Lys Lys Val Gly Ala Glu Asp Ile Glu Lys Thr Ile Lys Ala Cys Lys
305                 310                 315                 320

Pro Ser Asp Gln Ile Leu Lys Leu Leu Ser Leu Trp Arg Ile Lys Asn
            325                 330                 335

Gly Asp Gln Asp Thr Leu Lys Gly Leu Met His Ala Leu Lys His Ser
        340                 345                 350

Lys Thr Tyr His Phe Pro Lys Thr Val Thr Gln Ser Leu Lys Lys Thr
    355                 360                 365

Ile Arg Phe Leu His Ser Phe Thr Met Tyr Lys Leu Tyr Gln Lys Leu
370                 375                 380

Phe Leu Glu Met Ile Gly Asn Gln Val Gln Ser Val Lys Ile Ser Cys
385                 390                 395                 400

Leu
```

<210> SEQ ID NO 65

<211> LENGTH: 401
<212> TYPE: PRT
<213> ORGANISM: Homo sapiens

<400> SEQUENCE: 65

```
Met Asn Asn Leu Leu Cys Cys Ala Leu Val Phe Leu Asp Ile Ser Ile
1               5                   10                  15
Lys Trp Thr Thr Gln Glu Thr Phe Pro Pro Lys Tyr Leu His Tyr Asp
            20                  25                  30
Glu Glu Thr Ser His Gln Leu Leu Cys Asp Lys Cys Pro Pro Gly Thr
        35                  40                  45
Tyr Leu Lys Gln His Cys Thr Ala Lys Trp Lys Thr Val Cys Ala Pro
    50                  55                  60
Cys Pro Asp His Tyr Tyr Thr Asp Ser Trp His Thr Ser Asp Glu Cys
65                  70                  75                  80
Leu Tyr Cys Ser Pro Val Cys Lys Glu Leu Gln Tyr Val Lys Gln Glu
                85                  90                  95
Cys Asn Arg Thr His Asn Arg Val Cys Glu Cys Lys Glu Gly Arg Tyr
            100                 105                 110
Leu Glu Ile Glu Phe Cys Leu Lys His Arg Ser Cys Pro Pro Gly Phe
        115                 120                 125
Gly Val Val Gln Ala Gly Thr Pro Glu Arg Asn Thr Val Cys Lys Arg
    130                 135                 140
Cys Pro Asp Gly Phe Phe Ser Asn Glu Thr Ser Ser Lys Ala Pro Cys
145                 150                 155                 160
Arg Lys His Thr Asn Cys Ser Val Phe Gly Leu Leu Leu Thr Gln Lys
                165                 170                 175
Gly Asn Ala Thr His Asp Asn Ile Cys Ser Gly Asn Ser Glu Ser Thr
            180                 185                 190
Gln Lys Cys Gly Ile Asp Val Thr Leu Cys Glu Glu Ala Phe Phe Arg
        195                 200                 205
Phe Ala Val Pro Thr Lys Phe Thr Pro Asn Trp Leu Ser Val Leu Val
    210                 215                 220
Asp Asn Leu Pro Gly Thr Lys Val Asn Ala Glu Ser Val Glu Arg Ile
225                 230                 235                 240
Lys Arg Gln His Ser Ser Gln Glu Gln Thr Phe Gln Leu Leu Lys Leu
                245                 250                 255
Trp Lys His Gln Asn Lys Asp Gln Asp Ile Val Lys Lys Ile Ile Gln
            260                 265                 270
Asp Ile Asp Leu Cys Glu Asn Ser Val Gln Arg His Ile Gly His Ala
        275                 280                 285
Asn Leu Thr Phe Glu Gln Leu Arg Ser Leu Met Glu Ser Leu Pro Gly
    290                 295                 300
Lys Lys Val Gly Ala Glu Asp Ile Glu Lys Thr Ile Lys Ala Ser Lys
305                 310                 315                 320
Pro Ser Asp Gln Ile Leu Lys Leu Leu Ser Leu Trp Arg Ile Lys Asn
                325                 330                 335
Gly Asp Gln Asp Thr Leu Lys Gly Leu Met His Ala Leu Lys His Ser
            340                 345                 350
Lys Thr Tyr His Phe Pro Lys Thr Val Thr Gln Ser Leu Lys Lys Thr
        355                 360                 365
Ile Arg Phe Leu His Ser Phe Thr Met Tyr Lys Leu Tyr Gln Lys Leu
    370                 375                 380
Phe Leu Glu Met Ile Gly Asn Gln Val Gln Ser Val Lys Ile Ser Cys
```

```
385                 390                 395                 400

Leu

<210> SEQ ID NO 66
<211> LENGTH: 401
<212> TYPE: PRT
<213> ORGANISM: Homo sapiens

<400> SEQUENCE: 66

Met Asn Asn Leu Leu Cys Cys Ala Leu Val Phe Leu Asp Ile Ser Ile
1               5                   10                  15

Lys Trp Thr Thr Gln Glu Thr Phe Pro Pro Lys Tyr Leu His Tyr Asp
            20                  25                  30

Glu Glu Thr Ser His Gln Leu Leu Cys Asp Lys Cys Pro Pro Gly Thr
        35                  40                  45

Tyr Leu Lys Gln His Cys Thr Ala Lys Trp Lys Thr Val Cys Ala Pro
    50                  55                  60

Cys Pro Asp His Tyr Tyr Thr Asp Ser Trp His Thr Ser Asp Glu Cys
65                  70                  75                  80

Leu Tyr Cys Ser Pro Val Cys Lys Glu Leu Gln Tyr Val Lys Gln Glu
                85                  90                  95

Cys Asn Arg Thr His Asn Arg Val Cys Glu Cys Lys Glu Gly Arg Tyr
            100                 105                 110

Leu Glu Ile Glu Phe Cys Leu Lys His Arg Ser Cys Pro Pro Gly Phe
        115                 120                 125

Gly Val Val Gln Ala Gly Thr Pro Glu Arg Asn Thr Val Cys Lys Arg
    130                 135                 140

Cys Pro Asp Gly Phe Phe Ser Asn Glu Thr Ser Ser Lys Ala Pro Cys
145                 150                 155                 160

Arg Lys His Thr Asn Cys Ser Val Phe Gly Leu Leu Leu Thr Gln Lys
                165                 170                 175

Gly Asn Ala Thr His Asp Asn Ile Cys Ser Gly Asn Ser Glu Ser Thr
            180                 185                 190

Gln Lys Cys Gly Ile Asp Val Thr Leu Cys Glu Glu Ala Phe Phe Arg
        195                 200                 205

Phe Ala Val Pro Thr Lys Phe Thr Pro Asn Trp Leu Ser Val Leu Val
    210                 215                 220

Asp Asn Leu Pro Gly Thr Lys Val Asn Ala Glu Ser Val Glu Arg Ile
225                 230                 235                 240

Lys Arg Gln His Ser Ser Gln Glu Gln Thr Phe Gln Leu Leu Lys Leu
                245                 250                 255

Trp Lys His Gln Asn Lys Asp Gln Asp Ile Val Lys Lys Ile Ile Gln
            260                 265                 270

Asp Ile Asp Leu Cys Glu Asn Ser Val Gln Arg His Ile Gly His Ala
        275                 280                 285

Asn Leu Thr Phe Glu Gln Leu Arg Ser Leu Met Glu Ser Leu Pro Gly
    290                 295                 300

Lys Lys Val Gly Ala Glu Asp Ile Glu Lys Thr Ile Lys Ala Cys Lys
305                 310                 315                 320

Pro Ser Asp Gln Ile Leu Lys Leu Leu Ser Leu Trp Arg Ile Lys Asn
                325                 330                 335

Gly Asp Gln Asp Thr Leu Lys Gly Leu Met His Ala Leu Lys His Ser
            340                 345                 350

Lys Thr Tyr His Phe Pro Lys Thr Val Thr Gln Ser Leu Lys Lys Thr
```

```
                  355                 360                 365
Ile Arg Phe Leu His Ser Phe Thr Met Tyr Lys Leu Tyr Gln Lys Leu
370                 375                 380

Phe Leu Glu Met Ile Gly Asn Gln Val Gln Ser Val Lys Ile Ser Ser
385                 390                 395                 400

Leu

<210> SEQ ID NO 67
<211> LENGTH: 360
<212> TYPE: PRT
<213> ORGANISM: Homo sapiens

<400> SEQUENCE: 67

Met Asn Leu Leu Cys Cys Ala Leu Val Phe Leu Asp Ile Ser Ile
1               5                   10                  15

Lys Trp Thr Thr Gln Glu Pro Cys Pro Asp His Tyr Tyr Thr Asp Ser
                20                  25                  30

Trp His Thr Ser Asp Glu Cys Leu Tyr Cys Ser Pro Val Cys Lys Glu
            35                  40                  45

Leu Gln Tyr Val Lys Gln Glu Cys Asn Arg Thr His Asn Arg Val Cys
50                  55                  60

Glu Cys Lys Glu Gly Arg Tyr Leu Glu Ile Glu Phe Cys Leu Lys His
65                  70                  75                  80

Arg Ser Cys Pro Pro Gly Phe Gly Val Val Gln Ala Gly Thr Pro Glu
                85                  90                  95

Arg Asn Thr Val Cys Lys Arg Cys Pro Asp Gly Phe Phe Ser Asn Glu
            100                 105                 110

Thr Ser Ser Lys Ala Pro Cys Arg Lys His Thr Asn Cys Ser Val Phe
        115                 120                 125

Gly Leu Leu Leu Thr Gln Lys Gly Asn Ala Thr His Asp Asn Ile Cys
    130                 135                 140

Ser Gly Asn Ser Glu Ser Thr Gln Lys Cys Gly Ile Asp Val Thr Leu
145                 150                 155                 160

Cys Glu Glu Ala Phe Phe Arg Phe Ala Val Pro Thr Lys Phe Thr Pro
                165                 170                 175

Asn Trp Leu Ser Val Leu Val Asp Asn Leu Pro Gly Thr Lys Val Asn
            180                 185                 190

Ala Glu Ser Val Glu Arg Ile Lys Arg Gln His Ser Ser Gln Glu Gln
        195                 200                 205

Thr Phe Gln Leu Leu Lys Leu Trp Lys His Gln Asn Lys Asp Gln Asp
    210                 215                 220

Ile Val Lys Lys Ile Ile Gln Asp Ile Asp Leu Cys Glu Asn Ser Val
225                 230                 235                 240

Gln Arg His Ile Gly His Ala Asn Leu Thr Phe Glu Gln Leu Arg Ser
                245                 250                 255

Leu Met Glu Ser Leu Pro Gly Lys Lys Val Gly Ala Glu Asp Ile Glu
            260                 265                 270

Lys Thr Ile Lys Ala Cys Lys Pro Ser Asp Gln Ile Leu Lys Leu Leu
        275                 280                 285

Ser Leu Trp Arg Ile Lys Asn Gly Asp Gln Asp Thr Leu Lys Gly Leu
    290                 295                 300

Met His Ala Leu Lys His Ser Lys Thr Tyr His Phe Pro Lys Thr Val
305                 310                 315                 320

Thr Gln Ser Leu Lys Lys Thr Ile Arg Phe Leu His Ser Phe Thr Met
```

```
                325                 330                 335
Tyr Lys Leu Tyr Gln Lys Leu Phe Leu Glu Met Ile Gly Asn Gln Val
            340                 345                 350

Gln Ser Val Lys Ile Ser Cys Leu
        355                 360

<210> SEQ ID NO 68
<211> LENGTH: 359
<212> TYPE: PRT
<213> ORGANISM: Homo sapiens

<400> SEQUENCE: 68

Met Asn Asn Leu Leu Cys Cys Ala Leu Val Phe Leu Asp Ile Ser Ile
1               5                   10                  15

Lys Trp Thr Thr Gln Glu Thr Phe Pro Pro Lys Tyr Leu His Tyr Asp
            20                  25                  30

Glu Glu Thr Ser His Gln Leu Leu Cys Asp Lys Cys Pro Pro Gly Thr
        35                  40                  45

Tyr Leu Lys Gln His Cys Thr Ala Lys Trp Lys Thr Val Cys Ala Glu
    50                  55                  60

Cys Lys Glu Gly Arg Tyr Leu Glu Ile Glu Phe Cys Leu Lys His Arg
65                  70                  75                  80

Ser Cys Pro Pro Gly Phe Gly Val Val Gln Ala Gly Thr Pro Glu Arg
                85                  90                  95

Asn Thr Val Cys Lys Arg Cys Pro Asp Gly Phe Phe Ser Asn Glu Thr
            100                 105                 110

Ser Ser Lys Ala Pro Cys Arg Lys His Thr Asn Cys Ser Val Phe Gly
        115                 120                 125

Leu Leu Leu Thr Gln Lys Gly Asn Ala Thr His Asp Asn Ile Cys Ser
    130                 135                 140

Gly Asn Ser Glu Ser Thr Gln Lys Cys Gly Ile Asp Val Thr Leu Cys
145                 150                 155                 160

Glu Glu Ala Phe Phe Arg Phe Ala Val Pro Thr Lys Phe Thr Pro Asn
                165                 170                 175

Trp Leu Ser Val Leu Val Asp Asn Leu Pro Gly Thr Lys Val Asn Ala
            180                 185                 190

Glu Ser Val Glu Arg Ile Lys Arg Gln His Ser Ser Gln Glu Gln Thr
        195                 200                 205

Phe Gln Leu Leu Lys Leu Trp Lys His Gln Asn Lys Asp Gln Asp Ile
    210                 215                 220

Val Lys Lys Ile Ile Gln Asp Ile Asp Leu Cys Glu Asn Ser Val Gln
225                 230                 235                 240

Arg His Ile Gly His Ala Asn Leu Thr Phe Glu Gln Leu Arg Ser Leu
                245                 250                 255

Met Glu Ser Leu Pro Gly Lys Lys Val Gly Ala Glu Asp Ile Glu Lys
            260                 265                 270

Thr Ile Lys Ala Cys Lys Pro Ser Asp Gln Ile Leu Lys Leu Leu Ser
        275                 280                 285

Leu Trp Arg Ile Lys Asn Gly Asp Gln Asp Thr Leu Lys Gly Leu Met
    290                 295                 300

His Ala Leu Lys His Ser Lys Thr Tyr His Phe Pro Lys Thr Val Thr
305                 310                 315                 320

Gln Ser Leu Lys Lys Thr Ile Arg Phe Leu His Ser Phe Thr Met Tyr
                325                 330                 335
```

```
Lys Leu Tyr Gln Lys Leu Phe Leu Glu Met Ile Gly Asn Gln Val Gln
            340                 345                 350

Ser Val Lys Ile Ser Cys Leu
        355

<210> SEQ ID NO 69
<211> LENGTH: 363
<212> TYPE: PRT
<213> ORGANISM: Homo sapiens

<400> SEQUENCE: 69

Met Asn Asn Leu Leu Cys Cys Ala Leu Val Phe Leu Asp Ile Ser Ile
1               5                   10                  15

Lys Trp Thr Thr Gln Glu Thr Phe Pro Pro Lys Tyr Leu His Tyr Asp
            20                  25                  30

Glu Glu Thr Ser His Gln Leu Leu Cys Asp Lys Cys Pro Pro Gly Thr
        35                  40                  45

Tyr Leu Lys Gln His Cys Thr Ala Lys Trp Lys Thr Val Cys Ala Pro
    50                  55                  60

Cys Pro Asp His Tyr Tyr Thr Asp Ser Trp His Thr Ser Asp Glu Cys
65                  70                  75                  80

Leu Tyr Cys Ser Pro Val Cys Lys Glu Leu Gln Tyr Val Lys Gln Glu
                85                  90                  95

Cys Asn Arg Thr His Asn Arg Val Cys Arg Cys Pro Asp Gly Phe Phe
            100                 105                 110

Ser Asn Glu Thr Ser Ser Lys Ala Pro Cys Arg Lys His Thr Asn Cys
        115                 120                 125

Ser Val Phe Gly Leu Leu Leu Thr Gln Lys Gly Asn Ala Thr His Asp
    130                 135                 140

Asn Ile Cys Ser Gly Asn Ser Glu Ser Thr Gln Lys Cys Gly Ile Asp
145                 150                 155                 160

Val Thr Leu Cys Glu Glu Ala Phe Phe Arg Phe Ala Val Pro Thr Lys
                165                 170                 175

Phe Thr Pro Asn Trp Leu Ser Val Leu Val Asp Asn Leu Pro Gly Thr
            180                 185                 190

Lys Val Asn Ala Glu Ser Val Glu Arg Ile Lys Arg Gln His Ser Ser
        195                 200                 205

Gln Glu Gln Thr Phe Gln Leu Leu Lys Leu Trp Lys His Gln Asn Lys
    210                 215                 220

Asp Gln Asp Ile Val Lys Lys Ile Ile Gln Asp Ile Asp Leu Cys Glu
225                 230                 235                 240

Asn Ser Val Gln Arg His Ile Gly His Ala Asn Leu Thr Phe Glu Gln
                245                 250                 255

Leu Arg Ser Leu Met Glu Ser Leu Pro Gly Lys Lys Val Gly Ala Glu
            260                 265                 270

Asp Ile Glu Lys Thr Ile Lys Ala Cys Lys Pro Ser Asp Gln Ile Leu
        275                 280                 285

Lys Leu Leu Ser Leu Trp Arg Ile Lys Asn Gly Asp Gln Asp Thr Leu
    290                 295                 300

Lys Gly Leu Met His Ala Leu Lys His Ser Lys Thr Tyr His Phe Pro
305                 310                 315                 320

Lys Thr Val Thr Gln Ser Leu Lys Lys Thr Ile Arg Phe Leu His Ser
                325                 330                 335

Phe Thr Met Tyr Lys Leu Tyr Gln Lys Leu Phe Leu Glu Met Ile Gly
            340                 345                 350
```

```
Asn Gln Val Gln Ser Val Lys Ile Ser Cys Leu
        355                 360
```

<210> SEQ ID NO 70
<211> LENGTH: 359
<212> TYPE: PRT
<213> ORGANISM: Homo sapiens

<400> SEQUENCE: 70

```
Met Asn Asn Leu Leu Cys Cys Ala Leu Val Phe Leu Asp Ile Ser Ile
1               5                   10                  15

Lys Trp Thr Thr Gln Glu Thr Phe Pro Pro Lys Tyr Leu His Tyr Asp
            20                  25                  30

Glu Glu Thr Ser His Gln Leu Leu Cys Asp Lys Cys Pro Pro Gly Thr
        35                  40                  45

Tyr Leu Lys Gln His Cys Thr Ala Lys Trp Lys Thr Val Cys Ala Pro
    50                  55                  60

Cys Pro Asp His Tyr Tyr Thr Asp Ser Trp His Thr Ser Asp Glu Cys
65                  70                  75                  80

Leu Tyr Cys Ser Pro Val Cys Lys Glu Leu Gln Tyr Val Lys Gln Glu
                85                  90                  95

Cys Asn Arg Thr His Asn Arg Val Cys Glu Cys Lys Glu Gly Arg Tyr
            100                 105                 110

Leu Glu Ile Glu Phe Cys Leu Lys His Arg Ser Cys Pro Pro Gly Phe
        115                 120                 125

Gly Val Val Gln Ala Gly Thr Pro Glu Arg Asn Thr Val Cys Lys Ser
    130                 135                 140

Gly Asn Ser Glu Ser Thr Gln Lys Cys Gly Ile Asp Val Thr Leu Cys
145                 150                 155                 160

Glu Glu Ala Phe Phe Arg Phe Ala Val Pro Thr Lys Phe Thr Pro Asn
                165                 170                 175

Trp Leu Ser Val Leu Val Asp Asn Leu Pro Gly Thr Lys Val Asn Ala
            180                 185                 190

Glu Ser Val Glu Arg Ile Lys Arg Gln His Ser Ser Gln Glu Gln Thr
        195                 200                 205

Phe Gln Leu Leu Lys Leu Trp Lys His Gln Asn Lys Asp Gln Asp Ile
    210                 215                 220

Val Lys Lys Ile Ile Gln Asp Ile Asp Leu Cys Glu Asn Ser Val Gln
225                 230                 235                 240

Arg His Ile Gly His Ala Asn Leu Thr Phe Glu Gln Leu Arg Ser Leu
                245                 250                 255

Met Glu Ser Leu Pro Gly Lys Lys Val Gly Ala Glu Asp Ile Glu Lys
            260                 265                 270

Thr Ile Lys Ala Cys Lys Pro Ser Asp Gln Ile Leu Lys Leu Leu Ser
        275                 280                 285

Leu Trp Arg Ile Lys Asn Gly Asp Gln Asp Thr Leu Lys Gly Leu Met
    290                 295                 300

His Ala Leu Lys His Ser Lys Thr Tyr His Phe Pro Lys Thr Val Thr
305                 310                 315                 320

Gln Ser Leu Lys Lys Thr Ile Arg Phe Leu His Ser Phe Thr Met Tyr
                325                 330                 335

Lys Leu Tyr Gln Lys Leu Phe Leu Glu Met Ile Gly Asn Gln Val Gln
            340                 345                 350

Ser Val Lys Ile Ser Cys Leu
```

<210> SEQ ID NO 71
<211> LENGTH: 326
<212> TYPE: PRT
<213> ORGANISM: Homo sapiens

<400> SEQUENCE: 71

Met Asn Asn Leu Leu Cys Cys Ala Leu Val Phe Leu Asp Ile Ser Ile
1               5                   10                  15

Lys Trp Thr Thr Gln Glu Thr Phe Pro Pro Lys Tyr Leu His Tyr Asp
            20                  25                  30

Glu Glu Thr Ser His Gln Leu Leu Cys Asp Lys Cys Pro Pro Gly Thr
        35                  40                  45

Tyr Leu Lys Gln His Cys Thr Ala Lys Trp Lys Thr Val Cys Ala Pro
    50                  55                  60

Cys Pro Asp His Tyr Tyr Thr Asp Ser Trp His Thr Ser Asp Glu Cys
65                  70                  75                  80

Leu Tyr Cys Ser Pro Val Cys Lys Glu Leu Gln Tyr Val Lys Gln Glu
                85                  90                  95

Cys Asn Arg Thr His Asn Arg Val Cys Glu Cys Lys Glu Gly Arg Tyr
            100                 105                 110

Leu Glu Ile Glu Phe Cys Leu Lys His Arg Ser Cys Pro Pro Gly Phe
        115                 120                 125

Gly Val Val Gln Ala Gly Thr Pro Glu Arg Asn Thr Val Cys Lys Arg
    130                 135                 140

Cys Pro Asp Gly Phe Phe Ser Asn Glu Thr Ser Ser Lys Ala Pro Cys
145                 150                 155                 160

Arg Lys His Thr Asn Cys Ser Val Phe Gly Leu Leu Leu Thr Gln Lys
                165                 170                 175

Gly Asn Ala Thr His Asp Asn Ile Cys Ser Gly Asn Ser Glu Ser Thr
            180                 185                 190

Gln Lys Cys Gly Ile Asp Ile Asp Leu Cys Glu Asn Ser Val Gln Arg
        195                 200                 205

His Ile Gly His Ala Asn Leu Thr Phe Glu Gln Leu Arg Ser Leu Met
    210                 215                 220

Glu Ser Leu Pro Gly Lys Lys Val Gly Ala Glu Asp Ile Glu Lys Thr
225                 230                 235                 240

Ile Lys Ala Cys Lys Pro Ser Asp Gln Ile Leu Lys Leu Leu Ser Leu
                245                 250                 255

Trp Arg Ile Lys Asn Gly Asp Gln Asp Thr Leu Lys Gly Leu Met His
            260                 265                 270

Ala Leu Lys His Ser Lys Thr Tyr His Phe Pro Lys Thr Val Thr Gln
        275                 280                 285

Ser Leu Lys Lys Thr Ile Arg Phe Leu His Ser Phe Thr Met Tyr Lys
    290                 295                 300

Leu Tyr Gln Lys Leu Phe Leu Glu Met Ile Gly Asn Gln Val Gln Ser
305                 310                 315                 320

Val Lys Ile Ser Cys Leu
                325

<210> SEQ ID NO 72
<211> LENGTH: 327
<212> TYPE: PRT
<213> ORGANISM: Homo sapiens -continued

```
<400> SEQUENCE: 72

Met Asn Asn Leu Leu Cys Cys Ala Leu Val Phe Leu Asp Ile Ser Ile
1               5                   10                  15

Lys Trp Thr Thr Gln Glu Thr Phe Pro Pro Lys Tyr Leu His Tyr Asp
            20                  25                  30

Glu Glu Thr Ser His Gln Leu Leu Cys Asp Lys Cys Pro Pro Gly Thr
        35                  40                  45

Tyr Leu Lys Gln His Cys Thr Ala Lys Trp Lys Thr Val Cys Ala Pro
    50                  55                  60

Cys Pro Asp His Tyr Tyr Thr Asp Ser Trp His Thr Ser Asp Glu Cys
65                  70                  75                  80

Leu Tyr Cys Ser Pro Val Cys Lys Glu Leu Gln Tyr Val Lys Gln Glu
                85                  90                  95

Cys Asn Arg Thr His Asn Arg Val Cys Glu Cys Lys Glu Gly Arg Tyr
            100                 105                 110

Leu Glu Ile Glu Phe Cys Leu Lys His Arg Ser Cys Pro Pro Gly Phe
        115                 120                 125

Gly Val Val Gln Ala Gly Thr Pro Glu Arg Asn Thr Val Cys Lys Arg
    130                 135                 140

Cys Pro Asp Gly Phe Phe Ser Asn Glu Thr Ser Ser Lys Ala Pro Cys
145                 150                 155                 160

Arg Lys His Thr Asn Cys Ser Val Phe Gly Leu Leu Leu Thr Gln Lys
                165                 170                 175

Gly Asn Ala Thr His Asp Asn Ile Cys Ser Gly Asn Ser Glu Ser Thr
            180                 185                 190

Gln Lys Cys Gly Ile Asp Val Thr Leu Cys Glu Glu Ala Phe Phe Arg
        195                 200                 205

Phe Ala Val Pro Thr Lys Phe Thr Pro Asn Trp Leu Ser Val Leu Val
    210                 215                 220

Asp Asn Leu Pro Gly Thr Lys Val Asn Ala Glu Ser Val Glu Arg Ile
225                 230                 235                 240

Lys Arg Gln His Ser Ser Gln Glu Gln Thr Phe Gln Leu Leu Lys Leu
                245                 250                 255

Trp Lys His Gln Asn Lys Asp Gln Asp Ile Val Lys Lys Ile Ile Gln
            260                 265                 270

Asp Ala Leu Lys His Ser Lys Thr Tyr His Phe Pro Lys Thr Val Thr
        275                 280                 285

Gln Ser Leu Lys Lys Thr Ile Arg Phe Leu His Ser Phe Thr Met Tyr
    290                 295                 300

Lys Leu Tyr Gln Lys Leu Phe Leu Glu Met Ile Gly Asn Gln Val Gln
305                 310                 315                 320

Ser Val Lys Ile Ser Cys Leu
                325

<210> SEQ ID NO 73
<211> LENGTH: 399
<212> TYPE: PRT
<213> ORGANISM: Homo sapiens

<400> SEQUENCE: 73

Met Asn Asn Leu Leu Cys Cys Ala Leu Val Phe Leu Asp Ile Ser Ile
1               5                   10                  15

Lys Trp Thr Thr Gln Glu Thr Phe Pro Pro Lys Tyr Leu His Tyr Asp
            20                  25                  30
```

```
Glu Glu Thr Ser His Gln Leu Leu Cys Asp Lys Cys Pro Gly Thr
            35                  40                  45
Tyr Leu Lys Gln His Cys Thr Ala Lys Trp Lys Thr Val Cys Ala Pro
     50                  55                  60
Cys Pro Asp His Tyr Tyr Thr Asp Ser Trp His Thr Ser Asp Glu Cys
 65              70                  75                  80
Leu Tyr Cys Ser Pro Val Cys Lys Glu Leu Gln Tyr Val Lys Gln Glu
                85                  90                  95
Cys Asn Arg Thr His Asn Arg Val Cys Glu Cys Lys Glu Gly Arg Tyr
            100                 105                 110
Leu Glu Ile Glu Phe Cys Leu Lys His Arg Ser Cys Pro Pro Gly Phe
        115                 120                 125
Gly Val Val Gln Ala Gly Thr Pro Glu Arg Asn Thr Val Cys Lys Arg
    130                 135                 140
Cys Pro Asp Gly Phe Phe Ser Asn Glu Thr Ser Ser Lys Ala Pro Cys
145                 150                 155                 160
Arg Lys His Thr Asn Cys Ser Val Phe Gly Leu Leu Leu Thr Gln Lys
                165                 170                 175
Gly Asn Ala Thr His Asp Asn Ile Cys Ser Gly Asn Ser Glu Ser Thr
            180                 185                 190
Gln Lys Cys Gly Ile Asp Val Thr Leu Cys Glu Glu Ala Phe Phe Arg
        195                 200                 205
Phe Ala Val Pro Thr Lys Phe Thr Pro Asn Trp Leu Ser Val Leu Val
    210                 215                 220
Asp Asn Leu Pro Gly Thr Lys Val Asn Ala Glu Ser Val Glu Arg Ile
225                 230                 235                 240
Lys Arg Gln His Ser Ser Gln Glu Gln Thr Phe Gln Leu Leu Lys Leu
                245                 250                 255
Trp Lys His Gln Asn Lys Asp Gln Asp Ile Val Lys Lys Ile Ile Gln
            260                 265                 270
Asp Ile Asp Leu Cys Glu Asn Ser Val Gln Arg His Ile Gly His Ala
        275                 280                 285
Asn Leu Thr Phe Glu Gln Leu Arg Ser Leu Met Glu Ser Leu Pro Gly
    290                 295                 300
Lys Lys Val Gly Ala Glu Asp Ile Glu Lys Thr Ile Lys Ala Cys Lys
305                 310                 315                 320
Pro Ser Asp Gln Ile Leu Lys Leu Leu Ser Leu Trp Arg Ile Lys Asn
                325                 330                 335
Gly Asp Gln Asp Thr Leu Lys Gly Leu Met His Ala Leu Lys His Ser
            340                 345                 350
Lys Thr Tyr His Phe Pro Lys Thr Val Thr Gln Ser Leu Lys Lys Thr
        355                 360                 365
Ile Arg Phe Leu His Ser Phe Thr Met Tyr Lys Leu Tyr Gln Lys Leu
    370                 375                 380
Phe Leu Glu Met Ile Gly Asn Gln Val Gln Ser Val Lys Ile Ser
385                 390                 395

<210> SEQ ID NO 74
<211> LENGTH: 351
<212> TYPE: PRT
<213> ORGANISM: Homo sapiens

<400> SEQUENCE: 74

Met Asn Asn Leu Leu Cys Cys Ala Leu Val Phe Leu Asp Ile Ser Ile
 1               5                  10                  15
```

```
Lys Trp Thr Thr Gln Glu Thr Phe Pro Pro Lys Tyr Leu His Tyr Asp
            20                  25                  30

Glu Glu Thr Ser His Gln Leu Leu Cys Asp Lys Cys Pro Pro Gly Thr
            35                  40                  45

Tyr Leu Lys Gln His Cys Thr Ala Lys Trp Lys Thr Val Cys Ala Pro
         50                  55                  60

Cys Pro Asp His Tyr Tyr Thr Asp Ser Trp His Thr Ser Asp Glu Cys
 65                  70                  75                  80

Leu Tyr Cys Ser Pro Val Cys Lys Glu Leu Gln Tyr Val Lys Gln Glu
             85                  90                  95

Cys Asn Arg Thr His Asn Arg Val Cys Glu Cys Lys Glu Gly Arg Tyr
            100                 105                 110

Leu Glu Ile Glu Phe Cys Leu Lys His Arg Ser Cys Pro Pro Gly Phe
            115                 120                 125

Gly Val Val Gln Ala Gly Thr Pro Glu Arg Asn Thr Val Cys Lys Arg
    130                 135                 140

Cys Pro Asp Gly Phe Phe Ser Asn Glu Thr Ser Ser Lys Ala Pro Cys
145                 150                 155                 160

Arg Lys His Thr Asn Cys Ser Val Phe Gly Leu Leu Leu Thr Gln Lys
                165                 170                 175

Gly Asn Ala Thr His Asp Asn Ile Cys Ser Gly Asn Ser Glu Ser Thr
            180                 185                 190

Gln Lys Cys Gly Ile Asp Val Thr Leu Cys Glu Glu Ala Phe Phe Arg
        195                 200                 205

Phe Ala Val Pro Thr Lys Phe Thr Pro Asn Trp Leu Ser Val Leu Val
    210                 215                 220

Asp Asn Leu Pro Gly Thr Lys Val Asn Ala Glu Ser Val Glu Arg Ile
225                 230                 235                 240

Lys Arg Gln His Ser Ser Gln Glu Gln Thr Phe Gln Leu Leu Lys Leu
                245                 250                 255

Trp Lys His Gln Asn Lys Asp Gln Asp Ile Val Lys Lys Ile Ile Gln
            260                 265                 270

Asp Ile Asp Leu Cys Glu Asn Ser Val Gln Arg His Ile Gly His Ala
        275                 280                 285

Asn Leu Thr Phe Glu Gln Leu Arg Ser Leu Met Glu Ser Leu Pro Gly
    290                 295                 300

Lys Lys Val Gly Ala Glu Asp Ile Glu Lys Thr Ile Lys Ala Cys Lys
305                 310                 315                 320

Pro Ser Asp Gln Ile Leu Lys Leu Leu Ser Leu Trp Arg Ile Lys Asn
                325                 330                 335

Gly Asp Gln Asp Thr Leu Lys Gly Leu Met His Ala Leu Lys His
            340                 345                 350

<210> SEQ ID NO 75
<211> LENGTH: 272
<212> TYPE: PRT
<213> ORGANISM: Homo sapiens

<400> SEQUENCE: 75

Met Asn Asn Leu Leu Cys Cys Ala Leu Val Phe Leu Asp Ile Ser Ile
 1               5                  10                  15

Lys Trp Thr Thr Gln Glu Thr Phe Pro Pro Lys Tyr Leu His Tyr Asp
            20                  25                  30

Glu Glu Thr Ser His Gln Leu Leu Cys Asp Lys Cys Pro Pro Gly Thr
```

```
              35                  40                  45
Tyr Leu Lys Gln His Cys Thr Ala Lys Trp Lys Thr Val Cys Ala Pro
 50                  55                  60

Cys Pro Asp His Tyr Tyr Thr Asp Ser Trp His Thr Ser Asp Glu Cys
 65                  70                  75                  80

Leu Tyr Cys Ser Pro Val Cys Lys Glu Leu Gln Tyr Val Lys Gln Glu
                 85                  90                  95

Cys Asn Arg Thr His Asn Arg Val Cys Glu Cys Lys Glu Gly Arg Tyr
                100                 105                 110

Leu Glu Ile Glu Phe Cys Leu Lys His Arg Ser Cys Pro Pro Gly Phe
            115                 120                 125

Gly Val Val Gln Ala Gly Thr Pro Glu Arg Asn Thr Val Cys Lys Arg
        130                 135                 140

Cys Pro Asp Gly Phe Phe Ser Asn Glu Thr Ser Ser Lys Ala Pro Cys
145                 150                 155                 160

Arg Lys His Thr Asn Cys Ser Val Phe Gly Leu Leu Leu Thr Gln Lys
                165                 170                 175

Gly Asn Ala Thr His Asp Asn Ile Cys Ser Gly Asn Ser Glu Ser Thr
            180                 185                 190

Gln Lys Cys Gly Ile Asp Val Thr Leu Cys Glu Glu Ala Phe Phe Arg
        195                 200                 205

Phe Ala Val Pro Thr Lys Phe Thr Pro Asn Trp Leu Ser Val Leu Val
    210                 215                 220

Asp Asn Leu Pro Gly Thr Lys Val Asn Ala Glu Ser Val Glu Arg Ile
225                 230                 235                 240

Lys Arg Gln His Ser Ser Gln Glu Gln Thr Phe Gln Leu Leu Lys Leu
                245                 250                 255

Trp Lys His Gln Asn Lys Asp Gln Asp Ile Val Lys Lys Ile Ile Gln
                260                 265                 270

<210> SEQ ID NO 76
<211> LENGTH: 197
<212> TYPE: PRT
<213> ORGANISM: Homo sapiens

<400> SEQUENCE: 76

Met Asn Asn Leu Leu Cys Cys Ala Leu Val Phe Leu Asp Ile Ser Ile
 1               5                  10                  15

Lys Trp Thr Thr Gln Glu Thr Phe Pro Pro Lys Tyr Leu His Tyr Asp
                 20                  25                  30

Glu Glu Thr Ser His Gln Leu Leu Cys Asp Lys Cys Pro Pro Gly Thr
             35                  40                  45

Tyr Leu Lys Gln His Cys Thr Ala Lys Trp Lys Thr Val Cys Ala Pro
 50                  55                  60

Cys Pro Asp His Tyr Tyr Thr Asp Ser Trp His Thr Ser Asp Glu Cys
 65                  70                  75                  80

Leu Tyr Cys Ser Pro Val Cys Lys Glu Leu Gln Tyr Val Lys Gln Glu
                 85                  90                  95

Cys Asn Arg Thr His Asn Arg Val Cys Glu Cys Lys Glu Gly Arg Tyr
                100                 105                 110

Leu Glu Ile Glu Phe Cys Leu Lys His Arg Ser Cys Pro Pro Gly Phe
            115                 120                 125

Gly Val Val Gln Ala Gly Thr Pro Glu Arg Asn Thr Val Cys Lys Arg
        130                 135                 140
```

```
Cys Pro Asp Gly Phe Phe Ser Asn Glu Thr Ser Ser Lys Ala Pro Cys
145                 150                 155                 160

Arg Lys His Thr Asn Cys Ser Val Phe Gly Leu Leu Leu Thr Gln Lys
                165                 170                 175

Gly Asn Ala Thr His Asp Asn Ile Cys Ser Gly Asn Ser Glu Ser Thr
            180                 185                 190

Gln Lys Cys Gly Ile
        195

<210> SEQ ID NO 77
<211> LENGTH: 143
<212> TYPE: PRT
<213> ORGANISM: Homo sapiens

<400> SEQUENCE: 77

Met Asn Asn Leu Leu Cys Cys Ala Leu Val Phe Leu Asp Ile Ser Ile
1               5                   10                  15

Lys Trp Thr Thr Gln Glu Thr Phe Pro Pro Lys Tyr Leu His Tyr Asp
                20                  25                  30

Glu Glu Thr Ser His Gln Leu Leu Cys Asp Lys Cys Pro Pro Gly Thr
            35                  40                  45

Tyr Leu Lys Gln His Cys Thr Ala Lys Trp Lys Thr Val Cys Ala Pro
        50                  55                  60

Cys Pro Asp His Tyr Tyr Thr Asp Ser Trp His Thr Ser Asp Glu Cys
65                  70                  75                  80

Leu Tyr Cys Ser Pro Val Cys Lys Glu Leu Gln Tyr Val Lys Gln Glu
                85                  90                  95

Cys Asn Arg Thr His Asn Arg Val Cys Glu Cys Lys Glu Gly Arg Tyr
            100                 105                 110

Leu Glu Ile Glu Phe Cys Leu Lys His Arg Ser Cys Pro Pro Gly Phe
        115                 120                 125

Gly Val Val Gln Ala Gly Thr Pro Glu Arg Asn Thr Val Cys Lys
    130                 135                 140

<210> SEQ ID NO 78
<211> LENGTH: 106
<212> TYPE: PRT
<213> ORGANISM: Homo sapiens

<400> SEQUENCE: 78

Met Asn Asn Leu Leu Cys Cys Ala Leu Val Phe Leu Asp Ile Ser Ile
1               5                   10                  15

Lys Trp Thr Thr Gln Glu Thr Phe Pro Pro Lys Tyr Leu His Tyr Asp
                20                  25                  30

Glu Glu Thr Ser His Gln Leu Leu Cys Asp Lys Cys Pro Pro Gly Thr
            35                  40                  45

Tyr Leu Lys Gln His Cys Thr Ala Lys Trp Lys Thr Val Cys Ala Pro
        50                  55                  60

Cys Pro Asp His Tyr Tyr Thr Asp Ser Trp His Thr Ser Asp Glu Cys
65                  70                  75                  80

Leu Tyr Cys Ser Pro Val Cys Lys Glu Leu Gln Tyr Val Lys Gln Glu
                85                  90                  95

Cys Asn Arg Thr His Asn Arg Val Cys Glu
            100                 105

<210> SEQ ID NO 79
<211> LENGTH: 393
```

```
<212> TYPE: PRT
<213> ORGANISM: Homo sapiens

<400> SEQUENCE: 79

Met Asn Leu Leu Cys Cys Ala Leu Val Phe Leu Asp Ile Ser Ile
1               5                   10                  15

Lys Trp Thr Thr Gln Glu Thr Phe Pro Pro Lys Tyr Leu His Tyr Asp
            20                  25                  30

Glu Glu Thr Ser His Gln Leu Leu Cys Asp Lys Cys Pro Pro Gly Thr
            35                  40                  45

Tyr Leu Lys Gln His Cys Thr Ala Lys Trp Lys Thr Val Cys Ala Pro
50                  55                  60

Cys Pro Asp His Tyr Tyr Thr Asp Ser Trp His Thr Ser Asp Glu Cys
65                  70                  75                  80

Leu Tyr Cys Ser Pro Val Cys Lys Glu Leu Gln Tyr Val Lys Gln Glu
                85                  90                  95

Cys Asn Arg Thr His Asn Arg Val Cys Glu Cys Lys Glu Gly Arg Tyr
            100                 105                 110

Leu Glu Ile Glu Phe Cys Leu Lys His Arg Ser Cys Pro Pro Gly Phe
        115                 120                 125

Gly Val Val Gln Ala Gly Thr Pro Glu Arg Asn Thr Val Cys Lys Arg
130                 135                 140

Cys Pro Asp Gly Phe Phe Ser Asn Glu Thr Ser Ser Lys Ala Pro Cys
145                 150                 155                 160

Arg Lys His Thr Asn Cys Ser Val Phe Gly Leu Leu Leu Thr Gln Lys
                165                 170                 175

Gly Asn Ala Thr His Asp Asn Ile Cys Ser Gly Asn Ser Glu Ser Thr
            180                 185                 190

Gln Lys Cys Gly Ile Asp Val Thr Leu Cys Glu Glu Ala Phe Phe Arg
        195                 200                 205

Phe Ala Val Pro Thr Lys Phe Thr Pro Asn Trp Leu Ser Val Leu Val
210                 215                 220

Asp Asn Leu Pro Gly Thr Lys Val Asn Ala Glu Ser Val Glu Arg Ile
225                 230                 235                 240

Lys Arg Gln His Ser Ser Gln Glu Gln Thr Phe Gln Leu Leu Lys Leu
                245                 250                 255

Trp Lys His Gln Asn Lys Asp Gln Asp Ile Val Lys Lys Ile Ile Gln
            260                 265                 270

Asp Ile Asp Leu Cys Glu Asn Ser Val Gln Arg His Ile Gly His Ala
        275                 280                 285

Asn Leu Thr Phe Glu Gln Leu Arg Ser Leu Met Glu Ser Leu Pro Gly
290                 295                 300

Lys Lys Val Gly Ala Glu Asp Ile Glu Lys Thr Ile Lys Ala Cys Lys
305                 310                 315                 320

Pro Ser Asp Gln Ile Leu Lys Leu Leu Ser Leu Trp Arg Ile Lys Asn
                325                 330                 335

Gly Asp Gln Asp Thr Leu Lys Gly Leu Met His Ala Leu Lys His Ser
            340                 345                 350

Lys Thr Tyr His Phe Pro Lys Thr Val Thr Gln Ser Leu Lys Lys Thr
        355                 360                 365

Ile Arg Phe Leu His Ser Phe Thr Met Tyr Lys Leu Tyr Gln Lys Leu
370                 375                 380

Phe Leu Glu Met Ile Gly Asn Leu Val
385                 390
```

<210> SEQ ID NO 80
<211> LENGTH: 321
<212> TYPE: PRT
<213> ORGANISM: Homo sapiens

<400> SEQUENCE: 80

Met Asn Leu Leu Cys Cys Ala Leu Val Phe Leu Asp Ile Ser Ile
1               5                   10                  15

Lys Trp Thr Thr Gln Glu Thr Phe Pro Pro Lys Tyr Leu His Tyr Asp
            20                  25                  30

Glu Glu Thr Ser His Gln Leu Leu Cys Asp Lys Cys Pro Pro Gly Thr
        35                  40                  45

Tyr Leu Lys Gln His Cys Thr Ala Lys Trp Lys Thr Val Cys Ala Pro
    50                  55                  60

Cys Pro Asp His Tyr Tyr Thr Asp Ser Trp His Thr Ser Asp Glu Cys
65                  70                  75                  80

Leu Tyr Cys Ser Pro Val Cys Lys Glu Leu Gln Tyr Val Lys Gln Glu
                85                  90                  95

Cys Asn Arg Thr His Asn Arg Val Cys Glu Cys Lys Glu Gly Arg Tyr
            100                 105                 110

Leu Glu Ile Glu Phe Cys Leu Lys His Arg Ser Cys Pro Pro Gly Phe
        115                 120                 125

Gly Val Val Gln Ala Gly Thr Pro Glu Arg Asn Thr Val Cys Lys Arg
    130                 135                 140

Cys Pro Asp Gly Phe Phe Ser Asn Glu Thr Ser Ser Lys Ala Pro Cys
145                 150                 155                 160

Arg Lys His Thr Asn Cys Ser Val Phe Gly Leu Leu Leu Thr Gln Lys
                165                 170                 175

Gly Asn Ala Thr His Asp Asn Ile Cys Ser Gly Asn Ser Glu Ser Thr
            180                 185                 190

Gln Lys Cys Gly Ile Asp Val Thr Leu Cys Glu Glu Ala Phe Phe Arg
        195                 200                 205

Phe Ala Val Pro Thr Lys Phe Thr Pro Asn Trp Leu Ser Val Leu Val
    210                 215                 220

Asp Asn Leu Pro Gly Thr Lys Val Asn Ala Glu Ser Val Glu Arg Ile
225                 230                 235                 240

Lys Arg Gln His Ser Ser Gln Glu Gln Thr Phe Gln Leu Leu Lys Leu
                245                 250                 255

Trp Lys His Gln Asn Lys Asp Gln Asp Ile Val Lys Lys Ile Ile Gln
            260                 265                 270

Asp Ile Asp Leu Cys Glu Asn Ser Val Gln Arg His Ile Gly His Ala
        275                 280                 285

Asn Leu Thr Phe Glu Gln Leu Arg Ser Leu Met Glu Ser Leu Pro Gly
    290                 295                 300

Lys Lys Val Gly Ala Glu Asp Ile Glu Lys Thr Ile Lys Ala Ser Leu
305                 310                 315                 320

Asp

<210> SEQ ID NO 81
<211> LENGTH: 187
<212> TYPE: PRT
<213> ORGANISM: Homo sapiens

<400> SEQUENCE: 81

```
Met Asn Asn Leu Leu Cys Cys Ala Leu Val Phe Leu Asp Ile Ser Ile
1               5                   10                  15

Lys Trp Thr Thr Gln Glu Thr Phe Pro Pro Lys Tyr Leu His Tyr Asp
            20                  25                  30

Glu Glu Thr Ser His Gln Leu Leu Cys Asp Lys Cys Pro Pro Gly Thr
        35                  40                  45

Tyr Leu Lys Gln His Cys Thr Ala Lys Trp Lys Thr Val Cys Ala Pro
    50                  55                  60

Cys Pro Asp His Tyr Tyr Thr Asp Ser Trp His Thr Ser Asp Glu Cys
65                  70                  75                  80

Leu Tyr Cys Ser Pro Val Cys Lys Glu Leu Gln Tyr Val Lys Gln Glu
                85                  90                  95

Cys Asn Arg Thr His Asn Arg Val Cys Glu Cys Lys Glu Gly Arg Tyr
            100                 105                 110

Leu Glu Ile Glu Phe Cys Leu Lys His Arg Ser Cys Pro Pro Gly Phe
        115                 120                 125

Gly Val Val Gln Ala Gly Thr Pro Glu Arg Asn Thr Val Cys Lys Arg
    130                 135                 140

Cys Pro Asp Gly Phe Phe Ser Asn Glu Thr Ser Ser Lys Ala Pro Cys
145                 150                 155                 160

Arg Lys His Thr Asn Cys Ser Val Phe Gly Leu Leu Leu Thr Gln Lys
            165                 170                 175

Gly Asn Ala Thr His Asp Asn Ile Cys Ser Gly
            180                 185

<210> SEQ ID NO 82
<211> LENGTH: 84
<212> TYPE: PRT
<213> ORGANISM: Homo sapiens

<400> SEQUENCE: 82

Met Asn Asn Leu Leu Cys Cys Ala Leu Val Phe Leu Asp Ile Ser Ile
1               5                   10                  15

Lys Trp Thr Thr Gln Glu Thr Phe Pro Pro Lys Tyr Leu His Tyr Asp
            20                  25                  30

Glu Glu Thr Ser His Gln Leu Leu Cys Asp Lys Cys Pro Pro Gly Thr
        35                  40                  45

Tyr Leu Lys Gln His Cys Thr Ala Lys Trp Lys Thr Val Cys Ala Pro
    50                  55                  60

Cys Pro Asp His Tyr Tyr Thr Asp Ser Trp His Thr Ser Asp Glu Cys
65                  70                  75                  80

Leu Tyr Leu Val

<210> SEQ ID NO 83
<211> LENGTH: 1206
<212> TYPE: DNA
<213> ORGANISM: Homo sapiens

<400> SEQUENCE: 83
atgaacaact tgctgtgctg cgcgctcgtg tttctggaca tctccattaa gtggaccacc      60
caggaaacgt tcctccaaa gtaccttcat tatgacgaag aaacctctca tcagctgttg     120
tgtgacaaat gtcctcctgg tacctaccta aaacaacact gtacagcaaa gtggaagacc    180
gtgtgcgccc cttgccctga ccactactac acagacagct ggcacaccag tgacgagtgt    240
ctatactgca gccccgtgtg caaggagctg cagtacgtca gcaggagtg caatcgcacc    300
```

```
cacaaccgcg tgtgcgaatg caaggaaggg cgctaccttg agatagagtt ctgcttgaaa    360
cataggagct gccctcctgg atttggagtg gtgcaagctg aaccccaga gcgaaataca     420 gtttgcaaaa gatgtccaga tgggttcttc tcaaatgaga cgtcatctaa agcaccctgt    480
agaaaacaca caaattgcag tgtctttggt ctcctgctaa ctcagaaagg aaatgcaaca    540
cacgacaaca tatgttccgg aaacagtgaa tcaactcaaa aagtggaat agatgttacc     600 ctgtgtgagg aggcattctt caggtttgct gttcctacaa agtttacgcc taactggctt    660
agtgtcttgg tagacaattt gcctggcacc aaagtaaacg cagagagtgt agagaggata    720
aaacggcaac acagctcaca agaacagact ttccagctgc tgaagttatg gaaacatcaa    780
aacaaagacc aagatatagt caagaagatc atccaagata ttgacctctg tgaaaacagc    840
gtgcagcggc acattggaca tgctaacctc accttcgagc agcttcgtag cttgatggaa    900
agcttaccgg gaagaaagt gggagcagaa gacattgaaa aacaataaa ggcatgcaaa      960 cccagtgacc agatcctgaa gctgctcagt ttgtggcgaa taaaaatgg cgaccaagac    1020 accttgaagg gcctaatgca cgcactaaag cactcaaaga cgtaccactt tcccaaaact    1080
gtcactcaga gtctaaagaa gaccatcagg ttccttcaca gcttcacaat gtacaaattg    1140
tatcagaagt tattttttaga aatgataggt aaccaggtcc aatcagtaaa aataagctgc   1200
ttataa                                                               1206

<210> SEQ ID NO 84
<211> LENGTH: 1206
<212> TYPE: DNA
<213> ORGANISM: Homo sapiens

<400> SEQUENCE: 84
atgaacaact tgctgtgctg cgcgctcgtg tttctggaca tctccattaa gtggaccacc     60
caggaaacgt ttcctccaaa gtaccttcat tatgacgaag aaacctctca tcagctgttg    120
tgtgacaaat gtcctcctgg tacctaccta aaacaacact gtacagcaaa gtggaagacc    180
gtgtgcgccc cttgccctga ccactactac acagacagct ggcacaccag tgacgagtgt    240
ctatactgca gccccgtgtg caaggagctg cagtacgtca agcaggagtg caatcgcacc    300
cacaaccgcg tgtgcgaatg caaggaaggg cgctaccttg agatagagtt ctgcttgaaa    360
cataggagct gccctcctgg atttggagtg gtgcaagctg aaccccaga gcgaaataca     420 gtttgcaaaa gatgtccaga tgggttcttc tcaaatgaga cgtcatctaa agcaccctgt    480
agaaaacaca caaattgcag tgtctttggt ctcctgctaa ctcagaaagg aaatgcaaca    540
cacgacaaca tatgttccgg aaacagtgaa tcaactcaaa aatgtggaat agatgttacc    600
ctgagtgagg aggcattctt caggtttgct gttcctacaa agtttacgcc taactggctt    660
agtgtcttgg tagacaattt gcctggcacc aaagtaaacg cagagagtgt agagaggata    720
aaacggcaac acagctcaca agaacagact ttccagctgc tgaagttatg gaaacatcaa    780
aacaaagacc aagatatagt caagaagatc atccaagata ttgacctctg tgaaaacagc    840
gtgcagcggc acattggaca tgctaacctc accttcgagc agcttcgtag cttgatggaa    900
agcttaccgg gaagaaagt gggagcagaa gacattgaaa aacaataaa ggcatgcaaa      960 cccagtgacc agatcctgaa gctgctcagt ttgtggcgaa taaaaatgg cgaccaagac    1020 accttgaagg gcctaatgca cgcactaaag cactcaaaga cgtaccactt tcccaaaact    1080
gtcactcaga gtctaaagaa gaccatcagg ttccttcaca gcttcacaat gtacaaattg    1140
tatcagaagt tattttttaga aatgataggt aaccaggtcc aatcagtaaa aataagctgc   1200
```

<210> SEQ ID NO 85
<211> LENGTH: 1206
<212> TYPE: DNA
<213> ORGANISM: Homo sapiens

<400> SEQUENCE: 85

```
atgaacaact tgctgtgctg cgcgctcgtg tttctggaca tctccattaa gtggaccacc      60
caggaaacgt tcctccaaa gtaccttcat tatgacgaag aaacctctca tcagctgttg     120
tgtgacaaat gtcctcctgg tacctaccta aacaacact gtacagcaaa gtggaagacc     180
gtgtgcgccc cttgccctga ccactactac acagacagc ggcacaccag tgacgagtgt     240
ctatactgca gccccgtgtg caaggagctg cagtacgtca gcaggagtg caatcgcacc     300
cacaaccgcg tgtgcgaatg caaggaaggg cgctaccttg agatagagtt ctgcttgaaa     360
cataggagct gccctcctgg atttggagtg gtgcaagctg aaccccaga gcgaaataca     420
gtttgcaaaa gatgtccaga tgggttcttc tcaaatgaga cgtcatctaa agcaccctgt     480
agaaaacaca caaattgcag tgtctttggt ctcctgctaa ctcagaaagg aaatgcaaca     540
cacgacaaca tatgttccgg aaacagtgaa tcaactcaaa atgtggaat agatgttacc     600
ctgtgtgagg aggcattctt caggtttgct gttcctacaa agtttacgcc taactggctt     660
agtgtcttgg tagacaattt gcctggcacc aaagtaaacg cagagagtgt agagaggata     720
aaacggcaac acagctcaca agaacagact ttccagctgc tgaagttatg gaaacatcaa     780
aacaagacc aagatatagt caagaagatc atccaagata ttgacctcag tgaaaacagc     840
gtgcagcggc acattggaca tgctaacctc accttcgagc agcttcgtag cttgatggaa     900
agcttaccgg gaaagaaagt gggagcagaa gacattgaaa aaacaataaa ggcatgcaaa     960
cccagtgacc agatcctgaa gctgctcagt ttgtggcgaa taaaaatgg cgaccaagac    1020
accttgaagg gcctaatgca cgcactaaag cactcaaaga cgtaccactt tcccaaaact    1080
gtcactcaga gtctaaagaa gaccatcagg ttccttcaca gcttcacaat gtacaaattg    1140
tatcagaagt tattttttaga aatgataggt aaccaggtcc aatcagtaaa aataagctgc    1200
ttataa                                                                1206
```

<210> SEQ ID NO 86
<211> LENGTH: 1206
<212> TYPE: DNA
<213> ORGANISM: Homo sapiens

<400> SEQUENCE: 86

```
atgaacaact tgctgtgctg cgcgctcgtg tttctggaca tctccattaa gtggaccacc      60
caggaaacgt tcctccaaa gtaccttcat tatgacgaag aaacctctca tcagctgttg     120
tgtgacaaat gtcctcctgg tacctaccta aacaacact gtacagcaaa gtggaagacc     180
gtgtgcgccc cttgccctga ccactactac acagacagc ggcacaccag tgacgagtgt     240
ctatactgca gccccgtgtg caaggagctg cagtacgtca gcaggagtg caatcgcacc     300
cacaaccgcg tgtgcgaatg caaggaaggg cgctaccttg agatagagtt ctgcttgaaa     360
cataggagct gccctcctgg atttggagtg gtgcaagctg aaccccaga gcgaaataca     420
gtttgcaaaa gatgtccaga tgggttcttc tcaaatgaga cgtcatctaa agcaccctgt     480
agaaaacaca caaattgcag tgtctttggt ctcctgctaa ctcagaaagg aaatgcaaca     540
```

-continued

| | |
|---|---|
| cacgacaaca tatgttccgg aaacagtgaa tcaactcaaa aatgtggaat agatgttacc | 600 |
| ctgtgtgagg aggcattctt caggtttgct gttcctacaa agtttacgcc taactggctt | 660 |
| agtgtcttgg tagacaattt gcctggcacc aaagtaaacg cagagagtgt agagaggata | 720 |
| aaacggcaac acagctcaca agaacagact ttccagctgc tgaagttatg gaaacatcaa | 780 |
| aacaaagacc aagatatagt caagaagatc atccaagata ttgacctctg tgaaaacagc | 840 |
| gtgcagcggc acattggaca tgctaacctc accttcgagc agcttcgtag cttgatggaa | 900 |
| agcttaccgg gaaagaaagt gggagcagaa gacattgaaa aaacaataaa ggcaagcaaa | 960 |
| cccagtgacc agatcctgaa gctgctcagt ttgtggcgaa taaaaaatgg cgaccaagac | 1020 |
| accttgaagg gcctaatgca cgcactaaag cactcaaaga cgtaccactt tcccaaaact | 1080 |
| gtcactcaga gtctaaagaa gaccatcagg ttccttcaca gcttcacaat gtacaaattg | 1140 |
| tatcagaagt tattttttaga aatgataggt aaccaggtcc aatcagtaaa ataagctgc | 1200 |
| ttataa | 1206 |

<210> SEQ ID NO 87
<211> LENGTH: 1206
<212> TYPE: DNA
<213> ORGANISM: Homo sapiens

<400> SEQUENCE: 87

| | |
|---|---|
| atgaacaact tgctgtgctg cgcgctcgtg tttctggaca tctccattaa gtggaccacc | 60 |
| caggaaacgt ttcctccaaa gtaccttcat tatgacgaag aaacctctca tcagctgttg | 120 |
| tgtgacaaat gtcctcctgg tacctaccta aaacaacact gtacagcaaa gtggaagacc | 180 |
| gtgtgcgccc cttgccctga ccactactac acagacagct ggcacaccag tgacgagtgt | 240 |
| ctatactgca gccccgtgtg caaggagctg cagtacgtca gcaggagtg caatcgcacc | 300 |
| cacaaccgcg tgtgcgaatg caaggaaggg cgctaccttg agatagagtt ctgcttgaaa | 360 |
| cataggagct gccctcctgg atttggagtg gtgcaagctg gaacccccaga gcgaaataca | 420 |
| gtttgcaaaa gatgtccaga tgggttcttc tcaaatgaga cgtcatctaa gcaccctgt | 480 |
| agaaaacaca caaattgcag tgtctttggt ctcctgctaa ctcagaaagg aaatgcaaca | 540 |
| cacgacaaca tatgttccgg aaacagtgaa tcaactcaaa aatgtggaat agatgttacc | 600 |
| ctgtgtgagg aggcattctt caggtttgct gttcctacaa agtttacgcc taactggctt | 660 |
| agtgtcttgg tagacaattt gcctggcacc aaagtaaacg cagagagtgt agagaggata | 720 |
| aaacggcaac acagctcaca agaacagact ttccagctgc tgaagttatg gaaacatcaa | 780 |
| aacaaagacc aagatatagt caagaagatc atccaagata ttgacctctg tgaaaacagc | 840 |
| gtgcagcggc acattggaca tgctaacctc accttcgagc agcttcgtag cttgatggaa | 900 |
| agcttaccgg gaaagaaagt gggagcagaa gacattgaaa aaacaataaa ggcatgcaaa | 960 |
| cccagtgacc agatcctgaa gctgctcagt ttgtggcgaa taaaaaatgg cgaccaagac | 1020 |
| accttgaagg gcctaatgca cgcactaaag cactcaaaga cgtaccactt tcccaaaact | 1080 |
| gtcactcaga gtctaaagaa gaccatcagg ttccttcaca gcttcacaat gtacaaattg | 1140 |
| tatcagaagt tattttttaga aatgataggt aaccaggtcc aatcagtaaa ataagcagc | 1200 |
| ttataa | 1206 |

<210> SEQ ID NO 88
<211> LENGTH: 1083
<212> TYPE: DNA
<213> ORGANISM: Homo sapiens

<400> SEQUENCE: 88

| | |
|---|---|
| atgaacaact tgctgtgctg cgcgctcgtg tttctggaca tctccattaa gtggaccacc | 60 |
| caggaacctt gccctgacca ctactacaca gacagctggc acaccagtga cgagtgtcta | 120 |
| tactgcagcc ccgtgtgcaa ggagctgcag tacgtcaagc aggagtgcaa tcgcacccac | 180 |
| aaccgcgtgt gcgaatgcaa ggaagggcgc taccttgaga tagagttctg cttgaaacat | 240 |
| aggagctgcc ctcctggatt tggagtggtg caagctggaa ccccagagcg aaatacagtt | 300 |
| tgcaaaagat gtccagatgg gttcttctca aatgagacgt catctaaagc accctgtaga | 360 |
| aaacacacaa attgcagtgt ctttggtctc ctgctaactc agaaaggaaa tgcaacacac | 420 |
| gacaacatat gttccggaaa cagtgaatca actcaaaaat gtggaataga gttaccctg | 480 |
| tgtgaggagg cattcttcag gtttgctgtt cctacaaagt ttacgcctaa ctggcttagt | 540 |
| gtcttggtag acaatttgcc tggcaccaaa gtaaacgcag agagtgtaga gaggataaaa | 600 |
| cggcaacaca gctcacaaga acagactttc cagctgctga gttatggaaa catcaaaac | 660 |
| aaagaccaag atatagtcaa gaagatcatc caagatattg acctctgtga aaacagcgtg | 720 |
| cagcggcaca ttggacatgc taacctcacc ttcgagcagc ttcgtagctt gatggaaagc | 780 |
| ttaccgggaa agaaagtggg agcagaagac attgaaaaaa caataaaggc atgcaaaccc | 840 |
| agtgaccaga tcctgaagct gctcagtttg tggcgaataa aaaatggcga ccaagacacc | 900 |
| ttgaagggcc taatgcacgc actaaagcac tcaaagacgt accactttcc caaaactgtc | 960 |
| actcagagtc taaagaagac catcaggttc cttcacagct tcacaatgta caaattgtat | 1020 |
| cagaagttat ttttagaaat gataggtaac caggtccaat cagtaaaaat aagctgctta | 1080 |
| taa | 1083 |

<210> SEQ ID NO 89
<211> LENGTH: 1080
<212> TYPE: DNA
<213> ORGANISM: Homo sapiens

<400> SEQUENCE: 89

| | |
|---|---|
| atgaacaact tgctgtgctg cgcgctcgtg tttctggaca tctccattaa gtggaccacc | 60 |
| caggaaacgt tcctccaaa gtaccttcat tatgacgaag aaacctctca tcagctgttg | 120 |
| tgtgacaaat gtcctcctgg tacctaccta aaacaacact gtacagcaaa gtggaagacc | 180 |
| gtgtgcgccg aatgcaagga agggcgctac cttgagatag agttctgctt gaaacatagg | 240 |
| agctgccctc ctggatttgg agtggtgcaa gctggaaccc cagagcgaaa tacagtttgc | 300 |
| aaaagatgtc cagatgggtt cttctcaaat gagacgtcat ctaaagcacc tgtagaaaa | 360 |
| cacacaaatt gcagtgtctt tggtctcctg ctaactcaga aggaaatgc aacacacgac | 420 |
| aacatatgtt ccggaaacag tgaatcaact caaaaatgtg aatagatgt taccctgtgt | 480 |
| gaggaggcat tcttcaggtt tgctgttcct acaaagttta cgcctaactg cttagtgtc | 540 |
| ttggtagaca atttgcctgg caccaaagta acgcagaga gtgtagagag gataaacgg | 600 |
| caacacagct cacaagaaca gactttccag ctgctgaagt tatggaaaca tcaaaacaaa | 660 |
| gaccaagata tagtcaagaa gatcatccaa gatattgacc tctgtgaaaa cagcgtgcag | 720 |
| cggcacattg gacatgctaa cctcaccttc gagcagcttc gtagcttgat ggaaagctta | 780 |
| ccgggaaaga agtgggagc agaagacatt gaaaaaacaa taaaggcatg caaacccagt | 840 |
| gaccagatcc tgaagctgct cagtttgtgg cgaataaaaa atggcgacca agacaccttg | 900 |

-continued

| aagggcctaa tgcacgcact aaagcactca aagacgtacc actttcccaa aactgtcact | 960 |
| cagagtctaa agaagaccat caggttcctt cacagcttca caatgtacaa attgtatcag | 1020 |
| aagttatttt tagaaatgat aggtaaccag gtccaatcag taaaaataag ctgcttataa | 1080 |

<210> SEQ ID NO 90
<211> LENGTH: 1092
<212> TYPE: DNA
<213> ORGANISM: Homo sapiens

<400> SEQUENCE: 90

| atgaacaact tgctgtgctg cgcgctcgtg tttctggaca tctccattaa gtggaccacc | 60 |
| caggaaacgt ttcctccaaa gtaccttcat tatgacgaag aaacctctca tcagctgttg | 120 |
| tgtgacaaat gtcctcctgg tacctaccta aaacaacact gtacagcaaa gtggaagacc | 180 |
| gtgtgcgccc cttgccctga ccactactac acagacagct ggcacaccag tgacgagtgt | 240 |
| ctatactgca gccccgtgtg caaggagctg cagtacgtca agcaggagtg caatcgcacc | 300 |
| cacaaccgcg tgtgcagatg tccagatggg ttcttctcaa atgagacgtc atctaaagca | 360 |
| ccctgtagaa acacacaaa ttgcagtgtc tttggtctcc tgctaactca gaaaggaaat | 420 |
| gcaacacacg acaacatatg ttccggaaac agtgaatcaa ctcaaaaatg tggaatagat | 480 |
| gttaccctgt gtgaggaggc attcttcagg tttgctgttc ctacaaagtt tacgcctaac | 540 |
| tggcttagtg tcttggtaga caatttgcct ggcaccaaag taaacgcaga gagtgtagag | 600 |
| aggataaaac ggcaacacag ctcacaagaa cagactttcc agctgctgaa gttatggaaa | 660 |
| catcaaaaca aagaccaaga tatagtcaag aagatcatcc aagatattga cctctgtgaa | 720 |
| aacagcgtgc agcggcacat tggacatgct aacctcacct cgagcagct tcgtagcttg | 780 |
| atggaaagct taccgggaaa gaaagtggga gcagaagaca ttgaaaaaac aataaaggca | 840 |
| tgcaaaccca gtgaccagat cctgaagctg ctcagtttgt ggcgaataaa aaatggcgac | 900 |
| caagacacct tgaagggcct aatgcacgca ctaaagcact caaagacgta ccactttccc | 960 |
| aaaactgtca ctcagagtct aaagaagacc atcaggttcc ttcacagctt cacaatgtac | 1020 |
| aaattgtatc agaagttatt tttagaaatg ataggtaacc aggtccaatc agtaaaaata | 1080 |
| agctgcttat aa | 1092 |

<210> SEQ ID NO 91
<211> LENGTH: 1080
<212> TYPE: DNA
<213> ORGANISM: Homo sapiens

<400> SEQUENCE: 91

| atgaacaact tgctgtgctg cgcgctcgtg tttctggaca tctccattaa gtggaccacc | 60 |
| caggaaacgt ttcctccaaa gtaccttcat tatgacgaag aaacctctca tcagctgttg | 120 |
| tgtgacaaat gtcctcctgg tacctaccta aaacaacact gtacagcaaa gtggaagacc | 180 |
| gtgtgcgccc cttgccctga ccactactac acagacagct ggcacaccag tgacgagtgt | 240 |
| ctatactgca gccccgtgtg caaggagctg cagtacgtca agcaggagtg caatcgcacc | 300 |
| cacaaccgcg tgtgcgaatg caaggaaggg cgctaccttg agatagagtt ctgcttgaaa | 360 |
| cataggagct gccctcctgg atttggagtg gtgcaagctg gaaccccaga gcgaaataca | 420 |
| gtttgcaaat ccggaaacag tgaatcaact caaaaatgtg gaatagatgt taccctgtgt | 480 |
| gaggaggcat tcttcaggtt tgctgttcct acaaagttta cgcctaactg gcttagtgtc | 540 |
| ttggtagaca atttgcctgg caccaaagta aacgcagaga gtgtagagag gataaaacgg | 600 |

| caacacagct cacaagaaca gactttccag ctgctgaagt tatggaaaca tcaaaacaaa | 660 |
| gaccaagata tagtcaagaa gatcatccaa gatattgacc tctgtgaaaa cagcgtgcag | 720 |
| cggcacattg acatgctaa cctcaccttc gagcagcttc gtagcttgat ggaaagctta | 780 |
| ccgggaaaga agtgggagc agaagacatt gaaaaaacaa taaaggcatg caaacccagt | 840 |
| gaccagatcc tgaagctgct cagtttgtgg cgaataaaaa atggcgacca agacaccttg | 900 |
| aagggcctaa tgcacgcact aaagcactca aagacgtacc actttcccaa aactgtcact | 960 |
| cagagtctaa agaagaccat caggttcctt cacagcttca caatgtacaa attgtatcag | 1020 |
| aagttatttt tagaaatgat aggtaaccag gtccaatcag taaaaataag ctgcttataa | 1080 |

```
<210> SEQ ID NO 92
<211> LENGTH: 981
<212> TYPE: DNA
<213> ORGANISM: Homo sapiens

<400> SEQUENCE: 92
```

| atgaacaact tgctgtgctg cgcgctcgtg tttctggaca tctccattaa gtggaccacc | 60 |
| caggaaacgt ttcctccaaa gtaccttcat tatgacgaag aaacctctca tcagctgttg | 120 |
| tgtgacaaat gtcctcctgg tacctaccta aaacaacact gtacagcaaa gtggaagacc | 180 |
| gtgtgcgccc cttgccctga ccactactac acagacagct ggcacaccag tgacgagtgt | 240 |
| ctatactgca gccccgtgtg caaggagctg cagtacgtca agcaggagtg caatcgcacc | 300 |
| cacaaccgcg tgtgcgaatg caaggaaggg cgctaccttg agatagagtt ctgcttgaaa | 360 |
| cataggagct gccctcctgg atttggagtg gtgcaagctg aaccccaga gcgaaataca | 420 |
| gtttgcaaaa gatgtccaga tgggttcttc tcaaatgaga cgtcatctaa gcaccctgt | 480 |
| agaaaacaca caaattgcag tgtctttggt ctcctgctaa ctcagaaagg aaatgcaaca | 540 |
| cacgacaaca tatgttccgg aaacagtgaa tcaactcaaa atgtggaat agatattgac | 600 |
| ctctgtgaaa acagcgtgca gcggcacatt ggacatgcta acctcacctt cgagcagctt | 660 |
| cgtagcttga tggaaagctt accgggaaag aagtgggag cagaagacat tgaaaaaaca | 720 |
| ataaaggcat gcaaacccag tgaccagatc ctgaagctgc tcagtttgtg gcgaataaaa | 780 |
| aatggcgacc aagacacctt gaagggccta atgcacgcac taaagcactc aaagacgtac | 840 |
| cactttccca aaactgtcac tcagagtcta agaagacca tcaggttcct tcacagcttc | 900 |
| acaatgtaca aattgtatca gaagttattt ttagaaatga taggtaacca ggtccaatca | 960 |
| gtaaaaataa gctgcttata a | 981 |

```
<210> SEQ ID NO 93
<211> LENGTH: 984
<212> TYPE: DNA
<213> ORGANISM: Homo sapiens

<400> SEQUENCE: 93
```

| atgaacaact tgctgtgctg cgcgctcgtg tttctggaca tctccattaa gtggaccacc | 60 |
| caggaaacgt ttcctccaaa gtaccttcat tatgacgaag aaacctctca tcagctgttg | 120 |
| tgtgacaaat gtcctcctgg tacctaccta aaacaacact gtacagcaaa gtggaagacc | 180 |
| gtgtgcgccc cttgccctga ccactactac acagacagct ggcacaccag tgacgagtgt | 240 |
| ctatactgca gccccgtgtg caaggagctg cagtacgtca agcaggagtg caatcgcacc | 300 |
| cacaaccgcg tgtgcgaatg caaggaaggg cgctaccttg agatagagtt ctgcttgaaa | 360 |

```
cataggagct gccctcctgg atttggagtg gtgcaagctg aacccccaga gcgaaataca    420
gtttgcaaaa gatgtccaga tgggttcttc tcaaatgaga cgtcatctaa agcaccctgt    480
agaaaacaca caaattgcag tgtctttggt ctcctgctaa ctcagaaagg aaatgcaaca    540
cacgacaaca tatgttccgg aaacagtgaa tcaactcaaa aatgtggaat agatgttacc    600
ctgtgtgagg aggcattctt caggtttgct gttcctacaa agtttacgcc taactggctt    660
agtgtcttgg tagacaattt gcctggcacc aaagtaaacg cagagagtgt agagaggata    720
aaacggcaac acagctcaca agaacagact ttccagctgc tgaagttatg gaaacatcaa    780
aacaaagacc aagatatagt caagaagatc atccaagacg cactaaagca ctcaaagacg    840
taccactttc ccaaaactgt cactcagagt ctaaagaaga ccatcaggtt ccttcacagc    900
ttcacaatgt acaaattgta tcagaagtta ttttagaaa tgataggtaa ccaggtccaa    960
tcagtaaaaa taagctgctt ataa                                          984

<210> SEQ ID NO 94
<211> LENGTH: 1200
<212> TYPE: DNA
<213> ORGANISM: Homo sapiens

<400> SEQUENCE: 94
atgaacaact tgctgtgctg cgcgctcgtg tttctggaca tctccattaa gtggaccacc     60
caggaaacgt ttcctccaaa gtaccttcat tatgacgaag aaacctctca tcagctgttg    120
tgtgacaaat gtcctcctgg tacctaccta aaacaacact gtacagcaaa gtggaagacc    180
gtgtgcgccc cttgccctga ccactactac acagacagct ggcacaccag tgacgagtgt    240
ctatactgca gccccgtgtg caaggagctg cagtacgtca agcaggagtg caatcgcacc    300
cacaaccgcg tgtgcgaatg caaggaaggg cgctaccttg agatagagtt ctgcttgaaa    360
cataggagct gccctcctgg atttggagtg gtgcaagctg aacccccaga gcgaaataca    420
gtttgcaaaa gatgtccaga tgggttcttc tcaaatgaga cgtcatctaa agcaccctgt    480
agaaaacaca caaattgcag tgtctttggt ctcctgctaa ctcagaaagg aaatgcaaca    540
cacgacaaca tatgttccgg aaacagtgaa tcaactcaaa aatgtggaat agatgttacc    600
ctgtgtgagg aggcattctt caggtttgct gttcctacaa agtttacgcc taactggctt    660
agtgtcttgg tagacaattt gcctggcacc aaagtaaacg cagagagtgt agagaggata    720
aaacggcaac acagctcaca agaacagact ttccagctgc tgaagttatg gaaacatcaa    780
aacaaagacc aagatatagt caagaagatc atccaagata ttgacctctg tgaaaacagc    840
gtgcagcggc acattggaca tgctaacctc accttcgagc agcttcgtag cttgatggaa    900
agcttaccgg gaaagaaagt gggagcagaa gacattgaaa aaacaataaa ggcatgcaaa    960
cccagtgacc agatcctgaa gctgctcagt ttgtggcgaa taaaaaatgg cgaccaagac   1020
accttgaagg gcctaatgca cgcactaaag cactcaagga cgtaccactt tcccaaaact   1080
gtcactcaga gtctaaagaa gaccatcagg ttccttcaca gcttcacaat gtacaaattg   1140
tatcagaagt tattttttaga aatgataggt aaccaggtcc aatcagtaaa aataagctaa   1200

<210> SEQ ID NO 95
<211> LENGTH: 1056
<212> TYPE: DNA
<213> ORGANISM: Homo sapiens

<400> SEQUENCE: 95
atgaacaact tgctgtgctg cgcgctcgtg tttctggaca tctccattaa gtggaccacc     60
```

| caggaaacgt | ttcctccaaa | gtaccttcat | tatgacgaag | aaacctctca | tcagctgttg | 120 |
| tgtgacaaat | gtcctcctgg | tacctaccta | aaacaacact | gtacagcaaa | gtggaagacc | 180 |
| gtgtgcgccc | cttgccctga | ccactactac | acagacagct | ggcacaccag | tgacgagtgt | 240 |
| ctatactgca | gccccgtgtg | caaggagctg | cagtacgtca | agcaggagtg | caatcgcacc | 300 |
| cacaaccgcg | tgtgcgaatg | caaggaaggg | cgctaccttg | agatagagtt | ctgcttgaaa | 360 |
| cataggagct | gccctcctgg | atttggagtg | gtgcaagctg | gaaccccaga | gcgaaataca | 420 |
| gtttgcaaaa | gatgtccaga | tgggttcttc | tcaaatgaga | cgtcatctaa | agcaccctgt | 480 |
| agaaaacaca | caaattgcag | tgtctttggt | ctcctgctaa | ctcagaaagg | aaatgcaaca | 540 |
| cacgacaaca | tatgttccgg | aaacagtgaa | tcaactcaaa | aatgtggaat | agatgttacc | 600 |
| ctgtgtgagg | aggcattctt | caggtttgct | gttcctacaa | agtttacgcc | taactggctt | 660 |
| agtgtcttgg | tagacaattt | gcctggcacc | aaagtaaacg | cagagagtgt | agagaggata | 720 |
| aaacggcaac | acagctcaca | agaacagact | ttccagctgc | tgaagttatg | gaaacatcaa | 780 |
| aacaaagacc | aagatatagt | caagaagatc | atccaagata | ttgacctctg | tgaaaacagc | 840 |
| gtgcagcggc | acattggaca | tgctaacctc | accttcgagc | agcttcgtag | cttgatggaa | 900 |
| agcttaccgg | gaaagaaagt | gggagcagaa | gacattgaaa | aaacaataaa | ggcatgcaaa | 960 |
| cccagtgacc | agatcctgaa | gctgctcagt | ttgtggcgaa | taaaaaatgg | cgaccaagac | 1020 |
| accttgaagg | gcctaatgca | cgcactaaag | cactga | | | 1056 |

<210> SEQ ID NO 96
<211> LENGTH: 819
<212> TYPE: DNA
<213> ORGANISM: Homo sapiens

<400> SEQUENCE: 96

| atgaacaact | tgctgtgctg | cgcgctcgtg | tttctggaca | tctccattaa | gtggaccacc | 60 |
| caggaaacgt | ttcctccaaa | gtaccttcat | tatgacgaag | aaacctctca | tcagctgttg | 120 |
| tgtgacaaat | gtcctcctgg | tacctaccta | aaacaacact | gtacagcaaa | gtggaagacc | 180 |
| gtgtgcgccc | cttgccctga | ccactactac | acagacagct | ggcacaccag | tgacgagtgt | 240 |
| ctatactgca | gccccgtgtg | caaggagctg | cagtacgtca | agcaggagtg | caatcgcacc | 300 |
| cacaaccgcg | tgtgcgaatg | caaggaaggg | cgctaccttg | agatagagtt | ctgcttgaaa | 360 |
| cataggagct | gccctcctgg | atttggagtg | gtgcaagctg | gaaccccaga | gcgaaataca | 420 |
| gtttgcaaaa | gatgtccaga | tgggttcttc | tcaaatgaga | cgtcatctaa | agcaccctgt | 480 |
| agaaaacaca | caaattgcag | tgtctttggt | ctcctgctaa | ctcagaaagg | aaatgcaaca | 540 |
| cacgacaaca | tatgttccgg | aaacagtgaa | tcaactcaaa | aatgtggaat | agatgttacc | 600 |
| ctgtgtgagg | aggcattctt | caggtttgct | gttcctacaa | agtttacgcc | taactggctt | 660 |
| agtgtcttgg | tagacaattt | gcctggcacc | aaagtaaacg | cagagagtgt | agagaggata | 720 |
| aaacggcaac | acagctcaca | agaacagact | ttccagctgc | tgaagttatg | gaaacatcaa | 780 |
| aacaaagacc | aagatatagt | caagaagatc | atccaatga | | | 819 |

<210> SEQ ID NO 97
<211> LENGTH: 594
<212> TYPE: DNA
<213> ORGANISM: Homo sapiens

<400> SEQUENCE: 97

```
atgaacaact tgctgtgctg cgcgctcgtg tttctggaca tctccattaa gtggaccacc      60
caggaaacgt ttcctccaaa gtaccttcat tatgacgaag aaacctctca tcagctgttg     120
tgtgacaaat gtcctcctgg tacctaccta aaacaacact gtacagcaaa gtggaagacc     180
gtgtgcgccc cttgccctga ccactactac acagacagct ggcacaccag tgacgagtgt     240
ctatactgca gccccgtgtg caaggagctg cagtacgtca agcaggagtg caatcgcacc     300
cacaaccgcg tgtgcgaatg caaggaaggg cgctaccttg agatagagtt ctgcttgaaa     360
cataggagct gccctcctgg atttggagtg gtgcaagctg aacccagca gcgaaataca     420 gtttgcaaaa gatgtccaga tgggttcttc tcaaatgaga cgtcatctaa agcaccctgt     480
agaaaacaca caaattgcag tgtctttggt ctcctgctaa ctcagaaagg aaatgcaaca     540
cacgacaaca tatgttccgg aaacagtgaa tcaactcaaa aatgtggaat atga           594

<210> SEQ ID NO 98
<211> LENGTH: 432
<212> TYPE: DNA
<213> ORGANISM: Homo sapiens

<400> SEQUENCE: 98
atgaacaact tgctgtgctg cgcgctcgtg tttctggaca tctccattaa gtggaccacc      60
caggaaacgt ttcctccaaa gtaccttcat tatgacgaag aaacctctca tcagctgttg     120
tgtgacaaat gtcctcctgg tacctaccta aaacaacact gtacagcaaa gtggaagacc     180
gtgtgcgccc cttgccctga ccactactac acagacagct ggcacaccag tgacgagtgt     240
ctatactgca gccccgtgtg caaggagctg cagtacgtca agcaggagtg caatcgcacc     300
cacaaccgcg tgtgcgaatg caaggaaggg cgctaccttg agatagagtt ctgcttgaaa     360
cataggagct gccctcctgg atttggagtg gtgcaagctg aacccagca gcgaaataca     420 gtttgcaaat ga                                                         432

<210> SEQ ID NO 99
<211> LENGTH: 321
<212> TYPE: DNA
<213> ORGANISM: Homo sapiens

<400> SEQUENCE: 99
atgaacaact tgctgtgctg cgcgctcgtg tttctggaca tctccattaa gtggaccacc      60
caggaaacgt ttcctccaaa gtaccttcat tatgacgaag aaacctctca tcagctgttg     120
tgtgacaaat gtcctcctgg tacctaccta aaacaacact gtacagcaaa gtggaagacc     180
gtgtgcgccc cttgccctga ccactactac acagacagct ggcacaccag tgacgagtgt     240
ctatactgca gccccgtgtg caaggagctg cagtacgtca agcaggagtg caatcgcacc     300
cacaaccgcg tgtgcgaatg a                                               321

<210> SEQ ID NO 100
<211> LENGTH: 1182
<212> TYPE: DNA
<213> ORGANISM: Homo sapiens

<400> SEQUENCE: 100
atgaacaact tgctgtgctg cgcgctcgtg tttctggaca tctccattaa gtggaccacc      60
caggaaacgt ttcctccaaa gtaccttcat tatgacgaag aaacctctca tcagctgttg     120
tgtgacaaat gtcctcctgg tacctaccta aaacaacact gtacagcaaa gtggaagacc     180
gtgtgcgccc cttgccctga ccactactac acagacagct ggcacaccag tgacgagtgt     240
```

```
ctatactgca gccccgtgtg caaggagctg cagtacgtca agcaggagtg caatcgcacc      300
cacaaccgcg tgtgcgaatg caaggaaggg cgctaccttg agatagagtt ctgcttgaaa      360
cataggagct gccctcctgg atttggagtg gtgcaagctg gaaccccaga gcgaaataca      420
gtttgcaaaa gatgtccaga tgggttcttc tcaaatgaga cgtcatctaa agcaccctgt      480
agaaaacaca caaattgcag tgtctttggt ctcctgctaa ctcagaaagg aaatgcaaca      540
cacgacaaca tatgttccgg aaacagtgaa tcaactcaaa aatgtggaat agatgttacc      600
ctgtgtgagg aggcattctt caggtttgct gttcctacaa agtttacgcc taactggctt      660
agtgtcttgg tagacaattt gcctggcacc aaagtaaacg cagagagtgt agagaggata      720
aaacggcaac acagctcaca agaacagact ttccagctgc tgaagttatg gaaacatcaa      780
aacaaagacc aagatatagt caagaagatc atccaagata ttgacctctg tgaaaacagc      840
gtgcagcggc acattggaca tgctaacctc accttcgagc agcttcgtag cttgatggaa      900
agcttaccgg gaaagaaagt gggagcagaa gacattgaaa aacaataaa ggcatgcaaa       960 cccagtgacc agatcctgaa gctgctcagt ttgtggcgaa taaaaatgg cgaccaagac      1020 accttgaagg gcctaatgca cgcactaaag cactcaaaga cgtaccactt tcccaaaact      1080
gtcactcaga gtctaaagaa gaccatcagg ttccttcaca gcttcacaat gtacaaattg      1140
tatcagaagt tattttaga aatgataggt aacctagtct ag                         1182
```

<210> SEQ ID NO 101
<211> LENGTH: 966
<212> TYPE: DNA
<213> ORGANISM: Homo sapiens

<400> SEQUENCE: 101

```
atgaacaact tgctgtgctg cgcgctcgtg tttctggaca tctccattaa gtggaccacc       60
caggaaacgt ttcctccaaa gtaccttcat tatgacgaag aaacctctca tcagctgttg      120
tgtgacaaat gtcctcctgg tacctaccta aaacaacact gtacagcaaa gtggaagacc      180
gtgtgcgccc cttgccctga ccactactac acagacagct ggcacaccag tgacgagtgt      240
ctatactgca gccccgtgtg caaggagctg cagtacgtca agcaggagtg caatcgcacc      300
cacaaccgcg tgtgcgaatg caaggaaggg cgctaccttg agatagagtt ctgcttgaaa      360
cataggagct gccctcctgg atttggagtg gtgcaagctg gaaccccaga gcgaaataca      420
gtttgcaaaa gatgtccaga tgggttcttc tcaaatgaga cgtcatctaa agcaccctgt      480
agaaaacaca caaattgcag tgtctttggt ctcctgctaa ctcagaaagg aaatgcaaca      540
cacgacaaca tatgttccgg aaacagtgaa tcaactcaaa aatgtggaat agatgttacc      600
ctgtgtgagg aggcattctt caggtttgct gttcctacaa agtttacgcc taactggctt      660
agtgtcttgg tagacaattt gcctggcacc aaagtaaacg cagagagtgt agagaggata      720
aaacggcaac acagctcaca agaacagact ttccagctgc tgaagttatg gaaacatcaa      780
aacaaagacc aagatatagt caagaagatc atccaagata ttgacctctg tgaaaacagc      840
gtgcagcggc acattggaca tgctaacctc accttcgagc agcttcgtag cttgatggaa      900
agcttaccgg gaaagaaagt gggagcagaa gacattgaaa aacaataaa ggctagtcta      960 gactag                                                                966
```

<210> SEQ ID NO 102
<211> LENGTH: 564
<212> TYPE: DNA

<400> SEQUENCE: 102

```
atgaacaact tgctgtgctg cgcgctcgtg tttctggaca tctccattaa gtggaccacc      60
caggaaacgt ttcctccaaa gtaccttcat tatgacgaag aaacctctca tcagctgttg     120
tgtgacaaat gtcctcctgg tacctaccta aaacaacact gtacagcaaa gtggaagacc     180
gtgtgcgccc cttgccctga ccactactac acagacagct ggcacaccag tgacgagtgt     240
ctatactgca gccccgtgtg caaggagctg cagtacgtca gcaggagtg caatcgcacc      300
cacaaccgcg tgtgcgaatg caaggaaggg cgctaccttg agatagagtt ctgcttgaaa     360
cataggagct gccctcctgg atttggagtg gtgcaagctg aaccccaga gcgaaataca      420
gtttgcaaaa gatgtccaga tgggttcttc tcaaatgaga cgtcatctaa agcaccctgt     480
agaaaacaca caaattgcag tgtctttggt ctcctgctaa ctcagaaagg aaatgcaaca     540
cacgacaaca tatgttccgg ctag                                            564
```

<210> SEQ ID NO 103
<211> LENGTH: 255
<212> TYPE: DNA
<213> ORGANISM: Homo sapiens

<400> SEQUENCE: 103

```
atgaacaact tgctgtgctg cgcgctcgtg tttctggaca tctccattaa gtggaccacc      60
caggaaacgt ttcctccaaa gtaccttcat tatgacgaag aaacctctca tcagctgttg     120
tgtgacaaat gtcctcctgg tacctaccta aaacaacact gtacagcaaa gtggaagacc     180
gtgtgcgccc cttgccctga ccactactac acagacagct ggcacaccag tgacgagtgt     240
ctatacctag tctag                                                      255
```

<210> SEQ ID NO 104
<211> LENGTH: 1317
<212> TYPE: DNA
<213> ORGANISM: Homo sapiens

<400> SEQUENCE: 104

```
ctggagacat ataacttgaa cacttggccc tgatggggaa gcagctctgc agggactttt      60
tcagccatct gtaaacaatt tcagtggcaa cccgcgaact gtaatccatg aatgggacca     120
cactttacaa gtcatcaagt ctaacttcta gaccagggaa ttaatggggg agacagcgaa     180
ccctagagca aagtgccaaa cttctgtcga tagcttgagg ctagtggaaa gacctcgagg     240
aggctactcc agaagttcag cgcgtaggaa gctccgatac caatagccct ttgatgatgg     300
tggggttggt gaagggaaca gtgctccgca aggttatccc tgcccaggc agtccaattt      360
tcactctgca gattctctct ggctctaact accccagata caaggagtg aatgcagaat      420
agcacgggct ttagggccaa tcagacatta gttagaaaaa ttcctactac atggtttatg     480
taaacttgaa gatgaatgat tgcgaactcc ccgaaaaggg ctcagacaat gccatgcata     540
aagaggggcc ctgtaatttg aggtttcaga acccgaagtg aaggggtcag gcagccgggt     600
acggcggaaa ctcacagctt tcgcccagcg agaggacaaa ggtctgggac acactccaac     660
tgcgtccgga tcttggctgg atcggactct caggtggag gagacacaag cacagcagct      720
gcccagcgtg tgcccagccc tccaccgct ggtcccggct gccaggaggc tggccgctgg      780
cgggaagggg ccgggaaacc tcagagcccc gcggagacag cagccgcctt gttcctcagc     840
ccggtggctt ttttttcccc tgctctccca ggggacagac accaccgccc caccccctcac    900
```

```
gccccacctc cctgggggat cctttccgcc ccagccctga aagcgttaat cctggagctt    960
tctgcacacc ccccgaccgc tcccgcccaa gcttcctaaa aagaaaggt gcaaagtttg   1020
gtccaggata gaaaaatgac tgatcaaagg caggcgatac ttcctgttgc cgggacgcta   1080
tataacgt gatgagcgca cgggctgcgg agacgcaccg gagcgctcgc ccagccgccg    1140
cctccaagcc cctgaggttt ccggggacca caatgaacaa gttgctgtgc tgcgcgctcg   1200
tggtaagtcc ctgggccagc cgacgggtgc ccggcgcctg gggaggctgc tgccacctgg   1260
tctcccaacc tcccagcgga ccggcgggga aaaggctcc actcgctccc tcccaag      1317
```

<210> SEQ ID NO 105
<211> LENGTH: 10190
<212> TYPE: DNA
<213> ORGANISM: Homo sapiens

<400> SEQUENCE: 105

```
gcttactttg tgccaaatct cattaggctt aaggtaatac aggactttga gtcaaatgat     60
actgttgcac ataagaacaa acctattttc atgctaagat gatgccactg tgttcctttc    120
tccttctagt ttctggacat ctccattaag tggaccaccc aggaaacgtt tcctccaaag    180
taccttcatt atgacgaaga aacctctcat cagctgttgt gtgacaaatg tcctcctggt    240
acctacctaa aacaacactg tacagcaaag tggaagaccg tgtgcgcccc ttgccctgac    300
cactactaca cagacagctg gcacaccagt gacgagtgtc tatactgcag ccccgtgtgc    360
aaggagctgc agtacgtcaa gcaggagtgc aatcgcaccc acaaccgcgt gtgcgaatgc    420
aaggaagggc gctaccttga gatagagttc tgcttgaaac ataggagctg ccctcctgga    480
tttggagtgg tgcaagctgg tacgtgtcaa tgtgcagcaa aattaattag gatcatgcaa    540
agtcagatag ttgtgacagt ttaggagaac acttttgttc tgatgacatt ataggatagc    600
aaattgcaaa ggtaatgaaa cctgccaggt aggtactatg tgtctggagt gcttccaaag    660
gaccattgct cagaggaata ctttgccact acagggcaat ttaatgacaa atctcaaatg    720
cagcaaatta ttctctcatg agatgcatga tggttttttt ttttttttt aaagaaacaa    780
actcaagttg cactattgat agttgatcta tacctctata tttcacttca gcatggacac    840
cttcaaactg cagcacttt tgacaaacat cagaaatgtt aatttatacc aagagagtaa    900
ttatgctcat attaatgaga ctctggagtg ctaacaataa gcagttataa ttaattatgt    960
aaaaaatgag aatggtgagg ggaattgcat ttcattatta aaaacaaggc tagttcttcc   1020
tttagcatgg gagctgagtg tttgggaggg taaggactat agcagaatct cttcaatgag   1080
cttattcttt atcttagaca aaacagattg tcaagccaag agcaagcact tgcctataaa   1140
ccaagtgctt tctcttttgc attttgaaca gcattggtca gggctcatgt gtattgaatc   1200
ttttaaacca gtaacccacg ttttttttct gccacatttg cgaagcttca gtgcagccta   1260
taacttttca tagcttgaga aaattaagag tatccactta cttagatgga agaagtaatc   1320
agtatagatt ctgatgactc agtttgaagc agtgtttctc aactgaagcc ctgctgtatat  1380
tttaagaaat atctggattc ctaggctgga ctccttttg tgggcagctg tcctgcgcat    1440
tgtagaattt tggcagcacc cctggactct agccactaga taccaatagc agtccttccc   1500
ccatgtgaca gccaaaaatg tcttcagaca ctgtcaaatg tcgccaggtg gcaaaatcac   1560
tcctggttga gaacagggtc atcaatgcta agtatctgta actatttaa ctctcaaaac    1620
ttgtgatata caaagtctaa attattagac gaccaatact ttaggtttaa aggcatacaa   1680
```

```
atgaaacatt caaaaatcaa aatctattct gtttctcaaa tagtgaatct tataaaatta    1740
atcacagaag atgcaaattg catcagagtc ccttaaaatt cctcttcgta tgagtatttg    1800
agggaggaat tggtgatagt tcctactttc tattggatgg tactttgaga ctcaaaagct    1860
aagctaagtt gtgtgtgtgt cagggtgcgg ggtgtggaat cccatcagat aaaagcaaat    1920
ccatgtaatt cattcagtaa gttgtatatg tagaaaaatg aaaagtgggc tatgcagctt    1980
ggaaactaga gaattttgaa aaataatgga atcacaagta tctttctta aataagtaag     2040
aaaatctgtt tgtagaatga agcaagcagg cagccagaag actcagaaca aaagtacaca    2100
ttttactctg tgtacactgg cagcacagtg ggatttattt acctctccct ccctaaaaac    2160
ccacacagcg gttcctcttg ggaaataaga ggtttccagc ccaaagagaa ggaaagacta    2220
tgtggtgtta ctctaaaaag tatttaataa ccgttttgtt gttgctgttg ctgttttgaa    2280
atcagattgt ctcctctcca tattttattt acttcattct gttaattcct gtggaattac    2340
ttagagcaag catggtgaat tctcaactgt aaagccaaat ttctccatca ttataatttc    2400
acattttgcc tggcaggtta aattttttat atttccactg atagtaataa ggtaaaatca    2460
ttacttagat ggatagatct tttttcataaa aagtaccatc agttatagag ggaagtcatg    2520
ttcatgttca ggaaggtcat tagataaagc ttctgaatat attatgaaac attagttctg    2580
tcattcttag attcttttg ttaaataact ttaaaagcta acttacctaa aagaaatatc      2640
tgacacatat gaacttctca ttaggatgca ggagaagacc caagccacag atatgtatct    2700
gaagaatgaa caagattctt aggcccggca cggtggctca catctgtaat ctcaagagtt    2760
tgagaggtca aggcgggcag atcacctgag gtcaggagtt caagaccagc ctggccaaca    2820
tgatgaaacc ctgcctctac taaaaataca aaaattagca gggcatggtg gtgcatgcct    2880
gcaaccctag ctactcagga ggctgagaca ggagaatctc ttgaaccctc gaggcggagg    2940
ttgtggtgag ctgagatccc tctactgcac tccagcctgg gtgacagaga tgagactccg    3000
tccctgccgc cgcccccgcc ttccccccca aaaagattct tcttcatgca gaacatacgg    3060
cagtcaacaa agggagacct gggtccaggt gtccaagtca cttatttcga gtaaattagc    3120
aatgaaagaa tgccatggaa tccctgccca aatacctctg cttatgatat tgtagaattt    3180
gatatagagt tgtatcccat ttaaggagta ggatgtagta ggaaagtact aaaaacaaac    3240
acacaaacag aaaaccctct tgctttgta aggtggttcc taagataatg tcagtgcaat     3300
gctggaaata atatttaata tgtgaaggtt ttaggctgtg ttttcccctc ctgttcttt     3360
tttctgccag ccctttgtca tttttgcagg tcaatgaatc atgtagaaag agacaggaga    3420
tgaaactaga accagtccat tttgccccctt tttttatttt ctggttttgg taaaagatac    3480
aatgaggtag gaggttgaga tttataaatg aagtttaata agtttctgta gctttgattt    3540
ttctctttca tatttgttat cttgcataag ccagaattgg cctgtaaaat ctacatatgg    3600
atattgaagt ctaaatctgt tcaactagct tacactagat ggagatattt tcatattcag    3660
atacactgga atgtatgatc tagccatgcg taatatagtc aagtgtttga aggtatttat    3720
ttttaatagc gtcttttagtt gtggactggt tcaagttttt ctgccaatga tttcttcaaa   3780
tttatcaaat atttttccat catgaagtaa aatgcccttg cagtcaccct tcctgaagtt    3840
tgaacgactc tgctgtttta aacagtttaa gcaaatggta tatcatcttc cgtttactat    3900
gtagcttaac tgcaggctta cgcttttgag tcagcggcca actttattgc caccttcaaa    3960
agtttattat aatgttgtaa attttttactt ctcaaggtta gcatacttag gagttgcttc    4020
acaattagga ttcaggaaag aaagaacttc agtaggaact gattggaatt taatgatgca    4080
```

```
gcattcaatg ggtactaatt tcaaagaatg atattacagc agacacacag cagttatctt   4140
gattttctag gaataattgt atgaagaata tggctgacaa cacggcctta ctgccactca   4200
gcggaggctg gactaatgaa caccctaccc ttctttcctt tcctctcaca tttcatgagc   4260
gttttgtagg taacgagaaa attgacttgc atttgcatta caaggaggag aaactggcaa   4320
aggggatgat ggtggaagtt ttgttctgtc taatgaagtg aaaaatgaaa atgctagagt   4380
tttgtgcaac ataatagtag cagtaaaaac caagtgaaaa gtcttccaa  aactgtgtta   4440 agagggcatc tgctgggaaa cgatttgagg agaaggtact aaattgcttg gtattttccg   4500
taggaacccc agagcgaaat acagtttgca aaagatgtcc agatgggttc ttctcaaatg   4560
agacgtcatc taaagcaccc tgtagaaaac acacaaattg cagtgtcttt ggtctcctgc   4620
taactcagaa aggaaatgca acacacgaca acatatgttc cggaaacagt gaatcaactc   4680
aaaaatgtgg aataggtaat tacattccaa aatcgtctt  tgtacgattt tgtagtatca   4740
tctctctctc tgagttgaac acaaggcctc cagccacatt cttggtcaaa cttacatttt   4800
ccctttcttg aatcttaacc agctaaggct actctcgatg cattactgct aaagctacca   4860
ctcagaatct ctcaaaaact catcttctca cagataacac ctcaaagctt gattttctct   4920
cctttcacac tgaaatcaaa tcttgcccat aggcaagggg cagtgtcaag tttgccactg   4980
agatgaaatt aggagagtcc aaactgtaga attcacgttg tgtgttatta cttttcacgaa   5040 tgtctgtatt attaactaaa gtatatattg gcaactaaga agcaaagtga tataaacatg   5100
atgacaaatt aggccaggca tggtggctta ctcctataat cccaacattt tgggggggcca   5160 aggtaggcag atcacttgag gtcaggattt caagaccagc ctgaccaaca tggtgaaacc   5220
ttgtctctac taaaaataca aaaattagct gggcatggta gcaggcactt ctagtaccag   5280
ctactcaggg ctgaggcagg agaatcgctt gaacccagga gatggaggtt gcagtgagct   5340
gagattgtac cactgcactc cagtctgggc aacagagcaa gatttcatca cacacacaca   5400
cacacacaca cacacacaca ttagaaatgt gtacttggct ttgttaccta tggtattagt   5460
gcatctattg catggaactt ccaagctact ctggttgtgt taagctcttc attgggtaca   5520
ggtcactagt attaagttca ggttattcgg atgcattcca cggtagtgat gacaattcat   5580
caggctagtg tgtgtgttca ccttgtcact cccaccacta gactaatctc agaccttcac   5640
tcaaagacac attacactaa agatgatttg cttttttgtg tttaatcaag caatggtata   5700
aaccagcttg actctcccca aacagttttt cgtactacaa agaagtttat gaagcagaga   5760
aatgtgaatt gatatatata tgagattcta acccagttcc agcattgttt cattgtgtaa   5820
ttgaaatcat agacaagcca ttttagcctt tgctttctta tctaaaaaaa aaaaaaaaa   5880 aatgaaggaa ggggtattaa aaggagtgat caaattttaa cattctcttt aattaattca   5940
ttttaatttt tactttttttt catttattgt gcacttacta tgtggtactg tgctatagag   6000
gctttaacat ttataaaaac actgtgaaag ttgcttcaga tgaatatagg tagtagaacg   6060
gcagaactag tattcaaagc caggtctgat gaatccaaaa acaaacaccc attactccca   6120
ttttctggga catacttact ctacccagat gctctgggct ttgtaatgcc tatgtaaata   6180
acatagtttt atgtttggtt attttcctat gtaatgtcta cttatatatc tgtatctatc   6240
tcttgctttg tttccaaagg taaactatgt gtctaaatgt gggcaaaaaa taacacacta   6300
ttccaaatta ctgttcaaat tccttttaagt cagtgataat tatttgtttt gacattaatc   6360
atgaagttcc ctgtgggtac taggtaaacc tttaatagaa tgttaatgtt tgtattcatt   6420
```

```
ataagaattt ttggctgtta cttatttaca acaatatttc actctaatta gacatttact   6480
aaactttctc ttgaaaacaa tgcccaaaaa agaacattag aagacacgta agctcagttg   6540
gtctctgcca ctaagaccag ccaacagaag cttgatttta ttcaaacttt gcattttagc   6600
atattttatc ttggaaaatt caattgtgtt ggttttttgt ttttgtttgt attgaataga   6660
ctctcagaaa tccaattgtt gagtaaatct tctgggtttt ctaacctttc tttagatgtt   6720
accctgtgtg aggaggcatt cttcaggttt gctgttccta caaagtttac gcctaactgg   6780
cttagtgtct tggtagacaa tttgcctggc accaaagtaa acgcagagag tgtagagagg   6840
ataaaacggc aacacagctc acaagaacag actttccagc tgctgaagtt atggaaacat   6900
caaaacaaag accaagatat agtcaagaag atcatccaag gtaattacat tccaaaatac   6960
gtctttgtac gattttgtag tatcatctct ctctctgagt tgaacacaag gcctccagcc   7020
acattcttgg tcaaacttac attttcccctt tcttgaatct taaccagcta aggctactct   7080
cgatgcatta ctgctaaagc taccactcag aatctctcaa aaactcatct tctcacagat   7140
aacacctcaa agcttgattt tctctccttt cacactgaaa tcaaatcttg cccataggca   7200
aagggcagtg tcaagtttgc cactgagatg aaattaggag agtccaaact gtagaattca   7260
cgttgtgtgt tattactttc acgaatgtct gtattattaa ctaaagtata tattggcaac   7320
taagaagcaa agtgatataa acatgatgac aaattaggcc aggcatggtg gcttactcct   7380
ataatcccaa cattttgggg ggccaaggta ggcagatcac ttgaggtcag gatttcaaga   7440
ccagcctgac caacatggtg aaaccttgtc tctactaaaa atacaaaaat tagctgggca   7500
tggtagcagg cacttctagt accagctact cagggctgag gcaggagaat cgcttgaacc   7560
caggagatgg aggttgcagt gagctgagat tgtaccactg cactccagtc tgggcaacag   7620
agcaagattt catcacacac acacacacac acacacacac acacattaga aatgtgtact   7680
tggcttttgtt acctatggta ttagtgcatc tattgcatgg aacttccaag ctactctggt   7740
tgtgttaagc tcttcattgg gtacaggtca ctagtattaa gttcaggtta ttcggatgca   7800
ttccacggta gtgatgacaa ttcatcaggc tagtgtgtgt gttcaccttg tcactcccac   7860
cactagacta atctcagacc ttcactcaaa gacacattac actaaagatg atttgctttt   7920
ttgtgtttaa tcaagcaatg gtataaacca gcttgactct cccaaacag ttttttcgtac   7980
tacaaagaag tttatgaagc agagaaatgt gaattgatat atatatgaga ttctaaccca   8040
gttccagcat tgtttcattg tgtaattgaa atcatagaca agccatttta gcctttgctt   8100
tcttatctaa aaaaaaaaa aaaaaaatga aggaagggt attaaaagga gtgatcaaat   8160
tttaacattc tctttaatta attcattttt aatttttactt tttttcattt attgtgcact   8220
tactatgtgg tactgtgcta tagaggcttt aacatttata aaaacactgt gaaagttgct   8280
tcagatgaat ataggtagta gaacggcaga actagtattc aaagccaggt ctgatgaatc   8340
caaaacaaa cacccattac tcccattttc tgggacatac ttactctacc cagatgctct   8400
gggctttgta atgcctatgt aaataacata gttttatgtt tggttatttt cctatgtaat   8460
gtctacttat atatctgtat ctatctcttg ctttgtttcc aaaggtaaac tatgtgtcta   8520
aatgtgggca aaaataaca cactattcca aattactgtt caaattcctt taagtcagtg   8580
ataattattt gttttgacat taatcatgaa gttccctgtg ggtactaggt aaaccttttaa   8640
tagaatgtta atgtttgtat tcattataag aattttttggc tgttacttat ttacaacaat   8700
atttcactct aattagacat ttactaaact ttctcttgaa aacaatgccc aaaaaagaac   8760
attagaagac acgtaagctc agttggtctc tgccactaag accagccaac agaagcttga   8820
```

-continued

```
ttttattcaa actttgcatt ttagcatatt ttatcttgga aaattcaatt gtgttggttt      8880 tttgttttg  tttgtattga atagactctc agaaatccaa ttgttgagta aatcttctgg      8940
gttttctaac ctttctttag atattgacct ctgtgaaaac agcgtgcagc ggcacattgg      9000
acatgctaac ctcaccttcg agcagcttcg tagcttgatg gaaagcttac cgggaagaa       9060 agtgggagca gaagacattg aaaaaacaat aaaggcatgc aaacccagtg accagatcct      9120
gaagctgctc agtttgtggc gaataaaaaa tggcgaccaa gacaccttga agggcctaat      9180
gcacgcacta aagcactcaa agacgtacca ctttcccaaa actgtcactc agagtctaaa      9240
gaagaccatc aggttccttc acagcttcac aatgtacaaa ttgtatcaga agttattttt      9300
agaaatgata ggtaaccagg tccaatcagt aaaaataagc tgcttataac tggaaatggc      9360
cattgagctg tttcctcaca attggcgaga tcccatggat gagtaaactg tttctcaggc      9420
acttgaggct ttcagtgata tctttctcat taccagtgac taattttgcc acagggtact      9480
aaaagaaact atgatgtgga gaaggactaa acatctcctc aataaaccc  caaatggtta      9540 atccaactgt cagatctgga tcgttatcta ctgactatat tttcccttat tactgcttgc      9600
agtaattcaa ctggaaatta aaaaaaaaaa actagactcc actgggcctt actaaatatg      9660
ggaatgtcta acttaaatag ctttgggatt ccagctatgc tagaggcttt tattagaaag      9720
ccatattttt ttctgtaaaa gttactaata tatctgtaac actattacag tattgctatt      9780
tatattcatt cagatataag atttggacat attatcatcc tataaagaaa cggtatgact      9840
taattttaga aagaaaatta tattctgttt attatgacaa atgaaagaga aaatatatat      9900
ttttaatgga aagtttgtag cattttttcta ataggtactg ccatattttt ctgtgtggag      9960 tattttata atttttatctg tataagctgt aatatcattt tatagaaaat gcattattta     10020
gtcaattgtt taatgttgga aaacatatga aatataaatt atctgaatat tagatgctct     10080
gagaaattga atgtaccta  tttaaaagat tttatggttt tataactata taaatgacat     10140
tattaaagtt ttcaaattat tttttattgc tttctctgtt gcttttattt               10190
```

<210> SEQ ID NO 106
<211> LENGTH: 391
<212> TYPE: PRT
<213> ORGANISM: Homo sapiens

<400> SEQUENCE: 106

```
Phe Leu Asp Ile Ser Ile Lys Trp Thr Thr Gln Glu Thr Phe Pro Pro
1               5                   10                  15

Lys Tyr Leu His Tyr Asp Glu Glu Thr Ser His Gln Leu Leu Cys Asp
            20                  25                  30

Lys Cys Pro Pro Gly Thr Tyr Leu Lys Gln His Cys Thr Ala Lys Trp
        35                  40                  45

Lys Thr Val Cys Ala Pro Cys Pro Asp His Tyr Tyr Thr Asp Ser Trp
    50                  55                  60

His Thr Ser Asp Glu Cys Leu Tyr Cys Ser Pro Val Cys Lys Glu Leu
65                  70                  75                  80

Gln Tyr Val Lys Gln Glu Cys Asn Arg Thr His Asn Arg Val Cys Glu
                85                  90                  95

Cys Lys Glu Gly Arg Tyr Leu Glu Ile Glu Phe Cys Leu Lys His Arg
            100                 105                 110

Ser Cys Pro Pro Gly Phe Gly Val Val Gln Ala Gly Thr Pro Glu Arg
        115                 120                 125
```

```
Asn Thr Val Cys Lys Arg Cys Pro Asp Gly Phe Phe Ser Asn Glu Thr
    130                 135                 140

Ser Ser Lys Ala Pro Cys Arg Lys His Thr Asn Cys Ser Val Phe Gly
145                 150                 155                 160

Leu Leu Leu Thr Gln Lys Gly Asn Ala Thr His Asp Asn Ile Cys Ser
                165                 170                 175

Gly Asn Ser Glu Ser Thr Gln Lys Cys Gly Ile Asp Val Thr Leu Cys
            180                 185                 190

Glu Glu Ala Phe Phe Arg Phe Ala Val Pro Thr Lys Phe Thr Pro Asn
        195                 200                 205

Trp Leu Ser Val Leu Val Asp Asn Leu Pro Gly Thr Lys Val Asn Ala
    210                 215                 220

Glu Ser Val Glu Arg Ile Lys Arg Gln His Ser Ser Gln Glu Gln Thr
225                 230                 235                 240

Phe Gln Leu Leu Lys Leu Trp Lys His Gln Asn Lys Asp Gln Asp Ile
                245                 250                 255

Val Lys Lys Ile Ile Gln Asp Ile Asp Leu Cys Glu Asn Ser Val Gln
            260                 265                 270

Arg His Ile Gly His Ala Asn Leu Thr Phe Glu Gln Leu Arg Ser Leu
        275                 280                 285

Met Glu Ser Leu Pro Gly Lys Lys Val Gly Ala Glu Asp Ile Glu Lys
    290                 295                 300

Thr Ile Lys Ala Cys Lys Pro Ser Asp Gln Ile Leu Lys Leu Leu Ser
305                 310                 315                 320

Leu Trp Arg Ile Lys Asn Gly Asp Gln Asp Thr Leu Lys Gly Leu Met
                325                 330                 335

His Ala Leu Lys His Ser Lys Thr Tyr His Phe Pro Lys Thr Val Thr
            340                 345                 350

Gln Ser Leu Lys Lys Thr Ile Arg Phe Leu His Ser Phe Thr Met Tyr
        355                 360                 365

Lys Leu Tyr Gln Lys Leu Phe Leu Glu Met Ile Gly Asn Gln Val Gln
    370                 375                 380

Ser Val Lys Ile Ser Cys Leu
385                 390

<210> SEQ ID NO 107
<211> LENGTH: 20
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (12)..(12)
<223> OTHER INFORMATION: n = unknown

<400> SEQUENCE: 107
cargarcara cnttycaryt                                         20

<210> SEQ ID NO 108
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (10)..(10)
<223> OTHER INFORMATION: n = unknown
<220> FEATURE:
```

-continued

```
<221> NAME/KEY: misc_feature
<222> LOCATION: (16)..(16)
<223> OTHER INFORMATION: n = unknown

<400> SEQUENCE: 108
yttrtacatn gtraanswrt g                                           21
```

NUCLEIC ACID MOLECULES ENCODING OSTEOCLASTOGENESIS INHIBITORY FACTOR PROTEINS

CROSS-REFERENCE TO RELATED APPLICATIONS

This is a continuation of U.S. application Ser. No. 10/232,858, filed Sep. 3, 2002, now U.S. Pat. No. 6,855,808 which is a continuation of U.S. application Ser. No. 08/915,004, filed Aug. 20, 1997, now U.S. Pat. No. 7,125,686 which is a continuation-in-part of international application PCT/JP96/00374, filed Feb. 20, 1996, which claims priority to Japanese applications JP/054977, filed Feb. 20, 1995 and JP/207508, filed Jul. 21, 1995.

INCORPORATION OF SEQUENCE LISTING

Herein incorporated by reference is the Sequence Listing, which has been submitted on paper and diskette as a file named "SubSeq16991018.txt" which is 136,653 bytes in size (measured in MS-DOS), and which was created on Aug. 27, 2004.

FIELD OF THE INVENTION

This invention relates to a novel protein, osteoclastogenesis inhibitory factor (OCIF), and methods for producing the protein.

BACKGROUND OF THE INVENTION

Human bones are always remodelling by the repeated process of resorption and reconstitution. Osteoblasts and osteoclasts are considered to be the cells mainly responsible for bone formation and bone resorption, respectively. A typical example of a disease caused by abnormal bone metabolism is osteoporosis. Osteoporosis is known to develop when bone resorption by osteoclasts exceeds bone formation by osteoblasts, but the mechanism of osteoporosis has not yet been completely elucidated. Osteoporosis causes bone pain and makes bones fragile, leading to fracture, particularly in elderly patients. Osteoporosis has therefore become a social issue with the increasing number of elderly people in the population. Therefore, effective drugs for the treatment of the disease are expected to be developed. Bone mass reduction caused by abnormal bone metabolism is thought to be prevented by inhibiting bone resorption, improving bone formation, or improving the balance of bone metabolism.

Bone formation is promoted by stimulating growth, differentiation, or activation of osteoblasts. Many cytokines reportedly stimulate growth or differentiation of osteoblasts, i.e. fibroblast growth factor (FGF) (Rodan S. B. et al., Endocrinology vol. 121, p 1917, 1987), insulin-like growth factor-I (IGF-I) (Hock J. M. et al., Endocrinology vol. 122, p 254, 1988), insulin-like growth factor-II (IGF-II) (McCarthy T. et al., Endocrinology vol. 124, p 301, 1989), Activin A (Centrella M. et al., Mol. Cell Biol. vol. 11, p 250, 1991), Vasculotropin (Varonique M. et al., Biochem. Biophys. Res. Commun. vol. 199, p 380, 1994), and bone morphogenetic protein (BMP) (Yamaguchi, A. et al., J. Cell Biol. vol. 113, p 682, 1991, Sampath T. K. et al., J. Biol. Chem. vol. 267, p 20532, 1992, and Knutsen R. et al., Biochem. Biophys. Res. Commun. vol. 194, p 1352, 1993).

On the other hand, cytokines which inhibit differentiation and/or maturation of osteoclasts have also been intensively studied. Transforming growth factor-β (Chenu C. et al., Proc. Natl. Acad. Sci. USA, vol. 85, p 5683, 1988) and interleukin-4 (Kasano K. et al., Bone-Miner., vol. 21, p 179, 1993) inhibit the differentiation of osteoclasts. Calcitonin (Bone-Miner., vol. 17, p 347, 1992), macrophage colony-stimulating factor (Hattersley G. et al., J. Cell. Physiol. vol. 137, p 199, 1988), interleukin-4 (Watanabe, K. et al., Biochem. Biophys. Res. Commun. vol. 172, p 1035, 1990), and interferon-γ (Gowen M. et al., J. Bone-Miner. Res., vol. 1, p 469, 1986) inhibit bone resorption by osteoclasts.

These cytokines are expected to be effective drugs for improving bone mass reduction by stimulating bone formation and/or by inhibiting bone resorption. Cytokines such as insulin like growth factor-I and bone morphogenetic proteins have been investigated in clinical trials for their effectiveness for treating patients with bone diseases. Calcitonin is already used for osteoporosis and to diminish pain in osteoporosis patients.

Examples of drugs now clinically utilized for the treatment of bone diseases and for shortening the treatment period are dihydroxyvitamine $D_3$, vitamin $K_2$, calcitonin and its derivatives, hormones such as estradiol, ipriflavon, and calcium preparations. However, these drugs do not provide satisfactory therapeutic effects, and novel drug substances are expected to be developed. Since bone metabolism is manifest in the balance between bone resorption and bone formation, cytokines which inhibit osteoclast differentiation and/or maturation are expected to be developed as drugs for the treatment of bone diseases such as osteoporosis.

SUMMARY OF THE INVENTION

The purpose of this invention is to offer both a novel factor, termed osteoclastogenesis inhibitory factor (OCIF), and a procedure to produce the factor efficiently.

The inventors have intensively searched for osteoclastogenesis inhibitory factors in human embryonic fibroblast IMR-90 (ATCC CCL186) conditioned medium and have found a novel osteoclastogenesis inhibitory factor (OCIF) which inhibits differentiation and/or maturation of osteoclasts.

The inventors have established a method for accumulating the protein to a high concentration by culturing IMR-90 cells on alumina ceramic pieces, which function as cell adherence matrices.

The inventors have also established an efficient method for isolating the protein, OCIF, from the IMR-90 conditioned medium using the following sequential column chromatography: ion-exchange, heparin affinity, cibacron-blue affinity, and reverse phase.

After determining the amino acid sequence of the purified natural OCIF, a cDNA encoding this protein was successfully cloned. A procedure for producing this protein was also established. The invention concerns a protein which is produced by human lung fibroblast cells, has a molecular weight by SDS-PAGE of 60 kD under reducing conditions and molecular weights of 60 kD and 120 kD under non-reducing conditions, and has affinity for both cation-exchange resins and heparin. The protein's ability to inhibit the differentiation and maturation of osteoclasts is reduced when treated for 10 minutes at 70° C. or for 30 minutes at 56° C., and its ability to inhibit differentiation and maturation of osteoclasts is lost when treated for 10 minutes at 90° C. The amino acid sequence of the OCIF protein of the present invention is clearly different from any other factors known to inhibit the formation of osteoclasts.

The invention includes a method for purifying OCIF protein, comprising: (1) culturing human fibroblasts, (2) applying the conditioned medium to a heparin column to obtain the adsorbed fraction, (3) purifying the OCIF protein using a cation-exchange column, (4) purifying the OCIF protein using a heparin affinity column, (5) purifying the OCIF protein using a Cibacron blue affinity column, and (6) isolating the OCIF protein using reverse-phase column chromatography. Cibacron blue F3GA dye may be coupled to a carrier made of synthetic hydrophilic polymers, for example, to form columns conventionally called "blue columns".

The invention includes a method for producing OCIF protein in high concentration by culturing human fibroblasts using alumina ceramic pieces as the cell-adherence matrices.

Moreover, the inventors determined the amino acid sequences of peptides derived from OCIF, designed the oligonucleotide primers based on these amino acid sequences, and obtained cDNA fragments encoding OCIF from a cDNA library of IMR-90 human fetal lung fibroblast cells. The full length OCIF cDNA encoding the OCIF protein is cloned from a cDNA library using an OCIF DNA fragment as a probe. The OCIF cDNA containing the entire coding region is inserted into an expression vector. Recombinant OCIF can be produced by expressing the OCIF cDNA, containing the entire coding region, in mammalian cells or bacteria.

BRIEF DESCRIPTION OF THE FIGURES

FIGS. 1A and 1B show the elution pattern of crude OCIF protein (HILOAD™-Q/FF pass-through fraction; sample 3) from a HILOAD™-S/HP column.

FIG. 9 shows a comparison of OCIF (SEQ ID NO: 5) and OCIF2 (SEQ ID NO: 9) amino acid sequences.

FIG. 10 shows a comparison of OCIF (SEQ ID NO: 5) and OCIF3 (SEQ ID NO: 11) amino acid sequences.

FIG. 11 shows a comparison of OCIF (SEQ ID NO: 5) and OCIF4 (SEQ ID NO: 13) amino acid sequences.

FIG. 12 shows a comparison of OCIF (SEQ ID NO: 5) and OCIF5 (SEQ ID NO: 15) amino acid sequences.

DETAILED DESCRIPTION OF THE INVENTION

Figure 1A:
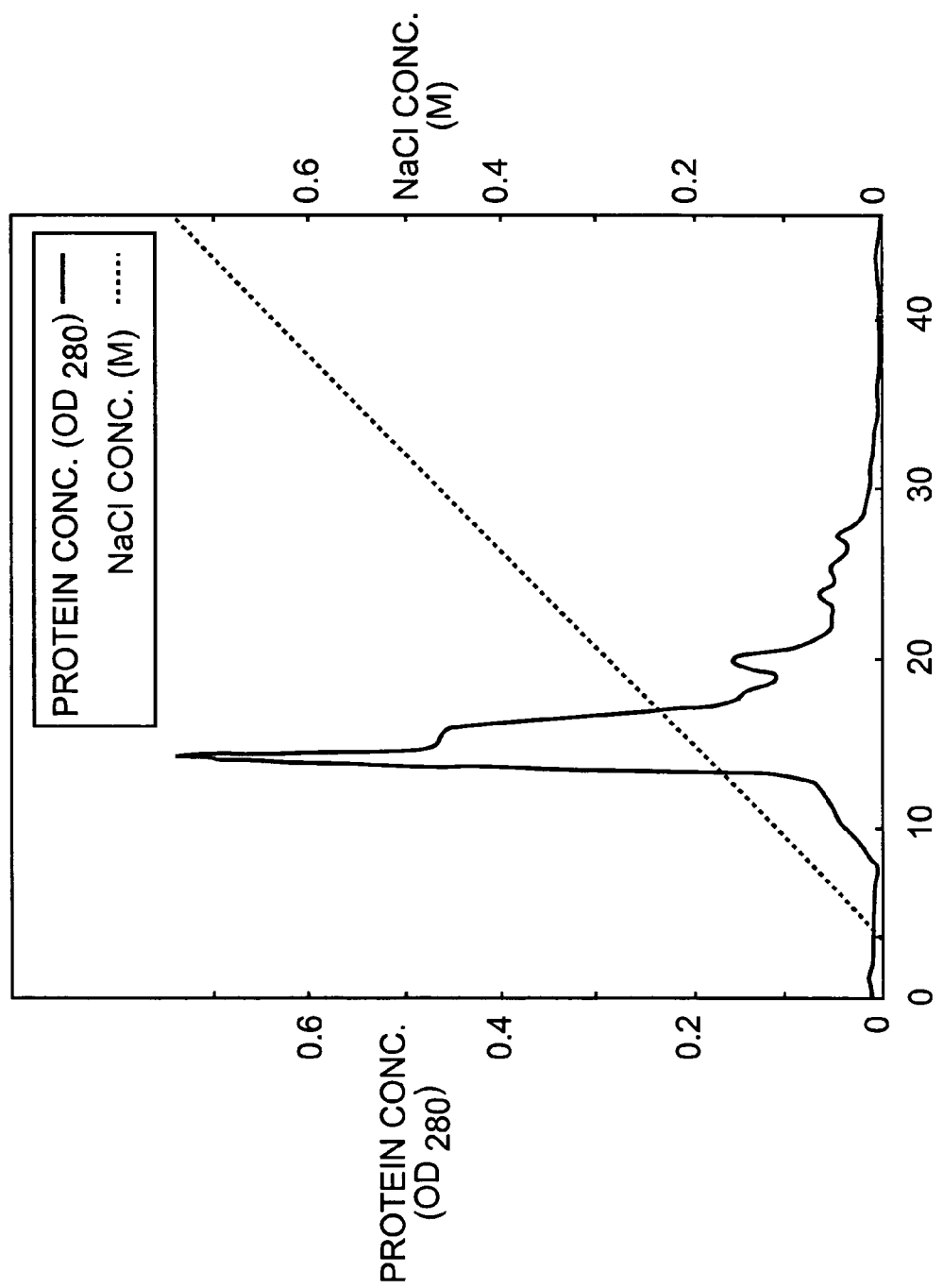

The OCIF protein of the present invention can be isolated from human fibroblast conditioned medium with high yield. The procedure to isolate OCIF is based on ordinary techniques for purifying proteins from biomaterials, in accordance with the physical and chemical properties of OCIF protein. For example, concentrating procedures include ordinary biochemical techniques such as ultrafiltration, lyophilization, and dialysis. Purifying procedures include combinations of several chromatographic techniques for purifying proteins such as ion-exchange column chromatography, affinity column chromatography, gel filtration column chromatography, hydrophobic column chromatography, reverse phase column chromatography, and preparative gel electrophoresis. The human fibroblasts used for the production of OCIF protein are preferably IMR-90 cells. A method for producing IMR-90 conditioned medium is preferably a process comprising adhering human embryonic fibroblast IMR-90 cells to alumina ceramic pieces in roller-bottles in DMEM medium supplemented with 5% newborn calf serum, and cultivating the cells in roller-bottles for 7 to 10 days by stand cultivation. CHAPS (3-[(3-cholamidopropyl)-dimethylammonio]-1-propanesulfonate) is preferably added to the buffer as a detergent in the protein purification procedure.

The OCIF protein of the instant invention can be obtained initially as a basic heparin binding OCIF fraction by applying the culture medium to a heparin column (Heparin-SEPHAROSE™ CL-6B, Pharmacia), eluting with 10 mM Tris-HCl buffer, pH 7.5, containing 2 M NaCl, and applying the OCIF fraction to a Q • anion-exchange column (HILOAD™-Q/FF, Pharmacia), and collecting the non-adsorbed fraction. OCIF protein can be purified by subjecting the obtained OCIF fraction to purification on an S • cation-exchange column (HILOAD™-S/FF, Pharmacia), a heparin column (Heparin-5PW, TOSOH), a Cibacron Blue column (Blue-5PW, TOSOH), and a reverse-phase column (BU-300 C4, Perkin Elmer).

The present invention relates to a method of cloning cDNA encoding the OCIF protein based on the amino acid sequence of natural OCIF and a method for obtaining recombinant OCIF protein. The OCIF protein is purified according to the method described in the present invention and is treated with endopeptidase (for example, lysylendopeptidase). The amino acid sequences of the peptides produced by the digestion are determined and the mixture of oligonucleotides that can encode each internal amino acid sequence is synthesized. The OCIF cDNA fragment is obtained by PCR (preferably RT-PCR, reverse transcriptase PCR) using the oligonucleotide mixtures described above as primers. The full length OCIF cDNA encoding the OCIF protein is cloned from a cDNA library using an OCIF DNA fragment as a probe. The OCIF cDNA containing the entire coding region is inserted into an expression vector. Recombinant OCIF can be produced by expressing the OCIF cDNA, containing the entire coding region, in mammalian cells or bacteria.

The present invention relates to the novel proteins OCIF2, OCIF3, OCIF4, and OCIF5 that are variants of OCIF and have the activity described above. These OCIF variants are obtained from the cDNA library constructed with IMR-90 poly(A)+RNA using the OCIF cDNA fragment as a hybridization probe. Each of the OCIF variant cDNAs containing the entire coding region is inserted into an expression vector. Each recombinant OCIF variant protein can be produced by expressing each of the OCIF variant cDNAs, containing the entire coding region, in conventional hosts. Each recombinant OCIF variant protein can be purified according to the method described in this invention. Each recombinant OCIF variant protein has the ability to inhibit osteoclastogenesis.

The present invention further includes OCIF mutants. They are substitution mutants comprising the replacement of one cysteine residue, possibly involved in dimer formation, with a serine residue or various deletion mutants of OCIF. Substitutions or deletions are introduced into the OCIF cDNA using polymerase chain reaction (PCR) or restriction enzyme digestion. Each of these mutated OCIF cDNAs is inserted into a vector having an appropriate promoter for gene expression. The resultant expression vector for each of the OCIF mutants is introduced into eukaryotic cells such as mammalian cells. Each of OCIF mutants can be obtained and purified from the conditioned media of the transfected cells.

The present invention provides polyclonal antibodies and a method to quantitatively determine OCIF concentration using these polyclonal antibodies.

Natural OCIF obtained from IMR-90 conditioned medium, recombinant OCIF produced by such hosts as microorganisms and eukaryotes using OCIF cDNA, synthetic peptides based on the amino acid sequence of OCIF, or peptides obtained from OCIF by partial digestion can be used as antigens. Anti-OCIF polyclonal antibodies are obtained by immunizing appropriate mammals with the antigens, in combination with adjuvants if necessary, and purifying the antibodies from the serum by ordinary purification methods. Anti-OCIF polyclonal antibodies which are labelled with radioisotopes or enzymes can be used in radio-immunoassay (RIA) systems or enzyme-immunoassay (EIA) systems. Using these assay systems, the concentration of OCIF in biological materials such as blood, ascites and cell-culture medium can be easily determined.

The present invention provides novel monoclonal antibodies and a method for quantitatively determining OCIF concentration using these monoclonal antibodies.

Anti-OCIF monoclonal antibodies can be produced by conventional methods using OCIF as an antigen. Native OCIF obtained from the culture medium of IMR-90 cells and recombinant OCIF produced by such hosts as microorganisms and eukaryotes transfected with OCIF cDNA can be used as antigens. Alternatively, synthetic peptides based on the amino acid sequence of OCIF and peptides obtained from OCIF by partial digestion can be also used as antigens. Immunized lymphocytes obtained by immunizing mammals such as mice or rats with the antigen or by an in vitro immunization method were fused with mammalian myeloma cells to obtain hybridomas. The hybridoma clones secreting antibodies which recognize OCIF were selected and cultured to obtain the desired antibodies. For immunizations, OCIF is suitably diluted with a saline solution (0.15 M NaCl), and is intravenously or intraperitoneally administered with an adjuvant to animals 2-5 times every 2-20 days. The immunized animal was killed three days after the final immunization, the spleen was removed and the splenocytes were used as immunized B lymphocytes.

Mouse myeloma cell lines useful for cell fusion with immunized B lymphocytes include, for example, p3/x63-Ag8, p3-U1, NS-1, MPC-11, SP-2/0, FO, p3x63 Ag8.653, and S194 cells. The rat cell line R-210 may also be used. Alternatively human B lymphocytes immunized by an in vitro immunization method are fused with human myeloma cells or EB virus transformed human B lymphocytes to produce human type antibodies.

Cell fusion of immunized B lymphocytes and myeloma cells is carried out principally by conventional methods. For example, the method of Koehler G. et al. (Nature 256, 495-497, 1975) is generally used. Alternatively, an electric pulse method can be used. The immunized B lymphocytes and transformed B cells are mixed at conventional ratios and a cell culture medium without FBS containing polyethylene glycol is generally used to fuse the cells. The fusions products are cultured in HAT selection medium containing FBS to select hybridomas.

An EIA, plaque assay, Ouchterlony, or agglutination assay can be used to screen for hybridomas producing anti-OCIF antibodies. EIA is a simple assay which is easy to perform with sufficient accuracy and is therefore generally used. The desired antibody can be selected easily and accurately using EIA and purified OCIF. Hybridomas obtained thereby can be cultured by conventional methods of cell culture and frozen for stock if necessary. The antibody can be produced by culturing hybridoma cells using ordinary cell culture methods or by transplanting hybridoma cells intraperitoneally into live animals. The antibody can be purified by ordinary purification methods such as salt precipitation, gel filtration, and affinity chromatography. The antibody obtained specifically reacts with OCIF and can be used to determine OCIF concentration and to purify OCIF protein. The antibodies of the present invention recognize epitopes of OCIF and have high affinity for OCIF. Therefore, they can be used for the construction of EIA. This assay system is useful for determining the concentration of OCIF in biological materials such as blood and ascites.

The present invention provides agents containing OCIF as an effective ingredient, that are useful for treating bone diseases. Rats were subjected to denervation of the left forelimb. Test compounds were administered daily after surgery for 14 days. After 2 weeks of treatment, the animals were sacrificed and their forelimbs were dissected. Thereafter bones were tested for mechanical strength by the three point bending method. OCIF improved the mechanical strength of bone in a dose dependent manner.

The OCIF protein of the invention is useful as a pharmaceutical ingredient for treating or improving decreased bone mass in bone diseases such as osteoporosis, rheumatism, osteoarthritis, and abnormal bone metabolism in multiple myeloma. OCIF protein is also useful as an antigen in the immunological diagnosis of bone diseases. Pharmaceutical preparations containing OCIF protein as an active ingredient are formulated and can be orally or parenterally administered. The preparation contains the OCIF protein of the present invention as an effective ingredient and is safely administered to humans and animals. Examples of pharmaceutical preparations include compositions for injection or intravenous drip, suppositories, nasal preparations, sublingual preparations, and tapes for percutaneous absorption. The pharmaceutical preparation for injection can be prepared by mixing a pharmacologically effective amount of OCIF protein and a pharmaceutically acceptable carrier. The carriers are vehicles and/or activators, e.g. amino acids, saccharides, cellulose derivatives, and other organic and inorganic compounds, which are generally added to active ingredients. When the OCIF protein is mixed with the vehicles and/or activators for injection, pH adjusters, buffers, stabilizers, solubilizing agents, etc. can be added by conventional methods, if necessary.

BEST MODE FOR CARRYING OUT THE INVENTION

The present invention will be further explained by the following examples, though the scope of the invention is not restricted thereto.

EXAMPLE 1

Preparation of a Conditioned Medium of Human Fibroblast IMR-90

Human fetal lung fibroblast IMR-90 (ATCC-CCL186) cells were cultured on alumina ceramic pieces (80 g) (alumina: 99.5%, manufactured by Toshiba Ceramic K.K.) in DMEM medium (manufactured by Gibco BRL Co.) supplemented with 5% CS and 10 mM HEPES buffer (500 ml/roller bottle) at 37° C. in the presence of 5% $CO_2$ for 7 to 10 days using 60 roller bottles (490 $cm^2$, 110×171 mm, manufactured by Corning Co.) in static culture. The conditioned medium was harvested and a fresh medium was added to the roller bottles. About 30 L of IMR-90 conditioned medium per batch culture was obtained. The conditioned medium was designated as sample 1.

EXAMPLE 2

Assay Method for Osteoclast Development Inhibitory Activity

Osteoclast development inhibitory activity was assayed by measuring tartrate-resistant acid phosphatase (TRAP) activity according to the methods of M. Kumegawa et al. (Protein Nucleic Acid Enzyme, vol. 34 p 999, 1989) and N. Takahashi et al. (Endocrinology, vol. 122, p 1373, 1988 ) with modifications. Briefly, bone marrow cells obtained from a 17 day-old mouse were suspended in α-MEM™ (manufactured by GIBCO BRL Co.) containing 10% FBS, $2 \times 10^{-8}$ M of activated vitamin $D_3$ and a test sample and were inoculated into each well of a 96-well plate at a cell density of $3 \times 10^5$ cells/0.2 ml/well. The plates were incubated for 7 days at 37° C. in humidified 5% $CO_2$. Cultures were maintained by replacing 0.16 ml of old medium with the same volume of fresh medium on day 3 and day 5 after cultivation began. On day 7, the plates were washed with phosphate buffered saline, and the cells were fixed with ethanol/acetone (1:1) for 1 min. at room temperature. Osteoclast development was tested by determining acid phosphatase activity using a kit (Acid Phosphatase, Leucocyte, Catalog No. 387-A, manufactured by Sigma Co.). A decrease in the number of TRAP positive cells was taken as an indication of OCIF activity.

EXAMPLE 3

Purification of OCIF i) Heparin SEPHAROSE™ CL-6B Column Chromatography

90 L of IMR-90 conditioned medium (sample 1) was filtered using a 0.22μ membrane filter (hydrophilic MILLIDISK™ 2000 $cm^2$, Millipore Co.), and was divided into three 30 liter portions. Each portion was applied to a heparin SEPHAROSE™ CL-6B column (5×4.1 cm, Pharmacia Co.) equilibrated with 10 mM Tris-HCl containing 0.3 M NaCl, pH 7.5. After washing the column with 10 mM Tris-HCl pH 7.5 at a flow rate of 500 ml/hr., the heparin SEPHAROSE™ CL-6B adsorbent protein fraction was eluted with 10 mM Tris-HCl, pH 7.5, containing 2 M NaCl. The fraction was designated sample 2.

ii) HILOAD™-Q/FF Column Chromatography

The heparin SEPHAROSE™-adsorbent fraction (sample 2) was dialyzed against 10 mM Tris-HCl, pH 7.5, supplemented with CHAPS to a final concentration of 0.1%, incubated at 4° C. overnight and divided into two portions. Each portion was then applied to an anion-exchange column (HILOAD™-Q/FF, 2.6×10 cm, Pharmacia Co.) which was equilibrated with 50 mM Tris-HCl, 0.1% CHAPS, pH 7.5 to obtain a non-adsorbent fraction (1000 ml). The fraction was designated sample 3.

iii) HILOAD™-S/HP Column Chromatography

The HILOAD™-Q non-adsorbent fraction (sample 3) was applied to a cation-exchange column (HILOAD™-S/HP, 2.6×10 cm, Pharmacia Co.) which was equilibrated with 50 mM Tris-HCl, 0.1% CHAPS, pH 7.5. After washing the column with 50 mM Tris-HCl, 0.1% CHAPS, pH 7.5, the adsorbed protein was eluted with a linear gradient from 0 to 1 M NaCl at a flow rate of 8 ml/min for 100 min. and fractions (12 ml) were collected. Every ten fractions from numbers 1 to 40 were pooled to form one portion. 100 μL each of the four portions was tested for OCIF activity. OCIF activity was observed in fractions 11 to 30 (as shown in FIGS. 1A and 1B). Fractions 21 to 30, which had higher specific activity, were pooled and designated sample 4.

iv) Heparin-5PW Affinity Column Chromatography

One hundred and twenty ml of HILOAD™-S fractions 21 to 30 (sample 4) was diluted with 240 ml of 50 mM Tris-HCl, 0.1% CHAPS, pH 7.5, and applied to a heparin-5PW affinity column (0.8×7.5 cm, Tosoh Co.) which was equilibrated with 50 mM Tris-HCl, 0.1% CHAPS, pH 7.5. After washing the column with 50 mM Tris-HCl, 0.1% CHAPS, pH 7.5, the adsorbed protein was eluted with a linear gradient from 0 to 2 M NaCl at a flow rate of 0.5 ml/min for 60 min. and fractions (0.5 ml) were collected. Fifty μL were removed from each fraction to test for OCIF activity. The active fractions, eluted with 0.7 to 1.3 M NaCl were pooled and designated sample 5.

v) Blue 5PW Affinity Column Chromatography

Ten ml of sample 5 were diluted with 190 ml of 50 mM Tris-HCl, 0.1% CHAPS, pH 7.5 and applied to a blue-5PW affinity column, (0.5×5 cm, Tosoh Co.) which was equilibrated with 50 mM Tris-HCl, 0.1% CHAPS, pH 7.5. After washing the column with 50 mM Tris-HCl, 0.1% CHAPS, pH 7.5, the adsorbed protein was eluted with a 30 ml linear gradient from 0 to 2 M NaCl at a flow rate of 0.5 ml/min. and fractions (0.5 ml) were collected. Using 25 µL of each fraction, OCIF activity was evaluated. Fractions 49 to 70, eluted with 1.0-1.6 M NaCl, had OCIF activity.

vi) Reverse Phase Column Chromatography

Figure 3:
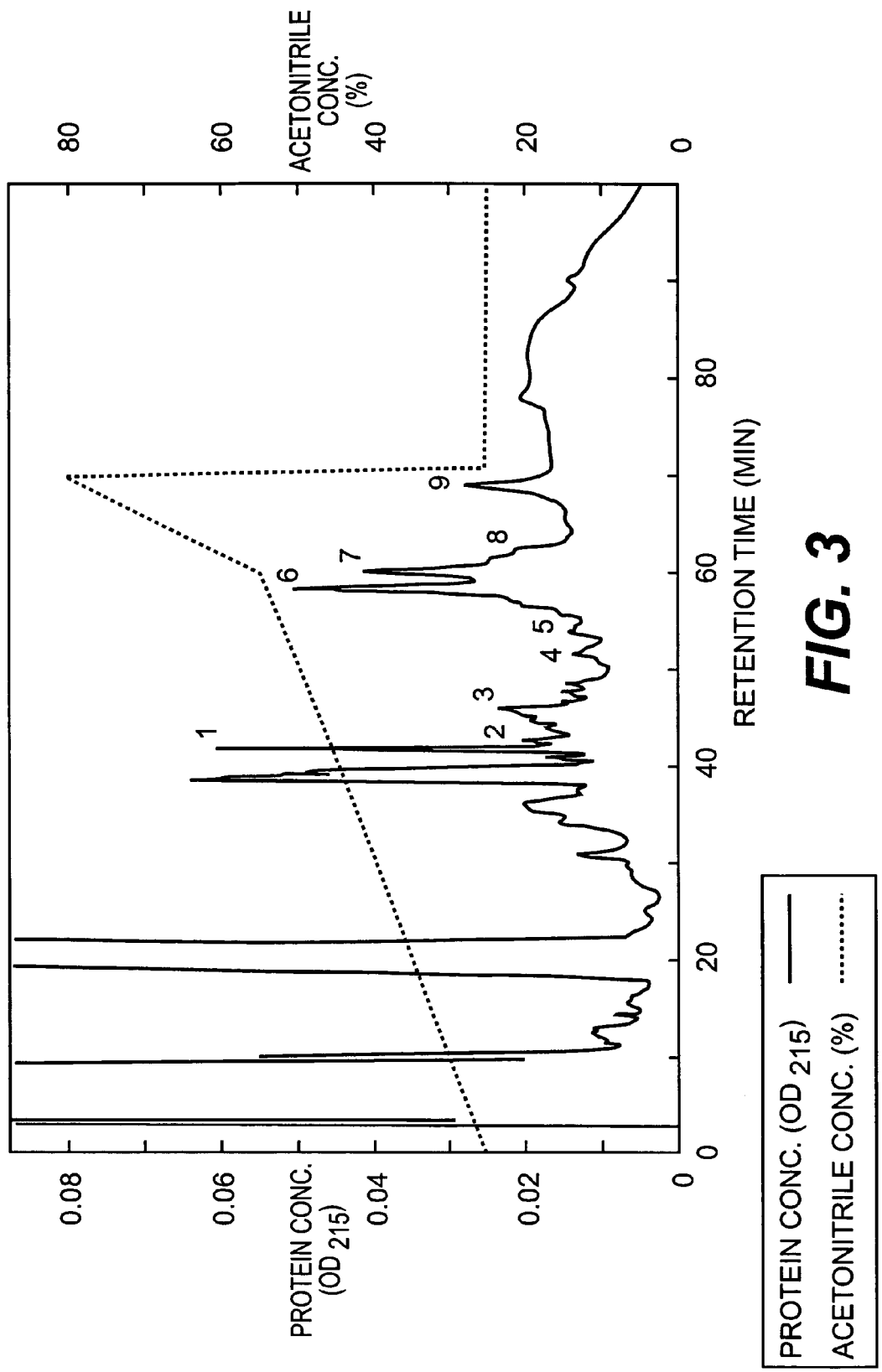
FIG. 3 shows the elution pattern of OCIF protein (blue-5PW fraction 49 to 50) from a reverse-phase column.

The blue 5PW fraction obtained by collecting fractions 49 and 50 was acidified with 10 µL of 25% TFA and applied to a reverse phase C4 column (BU-300, 2.1×220 mm, manufactured by Perkin-Elmer) which was equilibrated with 0.1% of TFA and 25% acetonitrile. The adsorbed protein was eluted with a linear gradient from 25 to 55% acetonitrile at a flow rate of 0.2 ml/min. for 60 min., and each protein peak was collected (FIG. 3). One hundred µL of each peak fraction was tested for OCIF activity, and peaks 6 and 7 had OCIF activity. The result was shown in Table 1.

TABLE 1

| Sample | Dilution | | | |
|---|---|---|---|---|
| | 1/40 | 1/120 | 1/360 | 1/1080 |
| Peak 6 | ++ | ++ | + | − |
| Peak 7 | ++ | + | − | − |

[++ means OCIF activity inhibiting osteoclast development more than 80%, + means OCIF activity inhibiting osteoclast development between 30% and 80%, and − means no OCIF activity.]

EXAMPLE 4

Molecular Weight of OCIF Protein

Figure 4A:
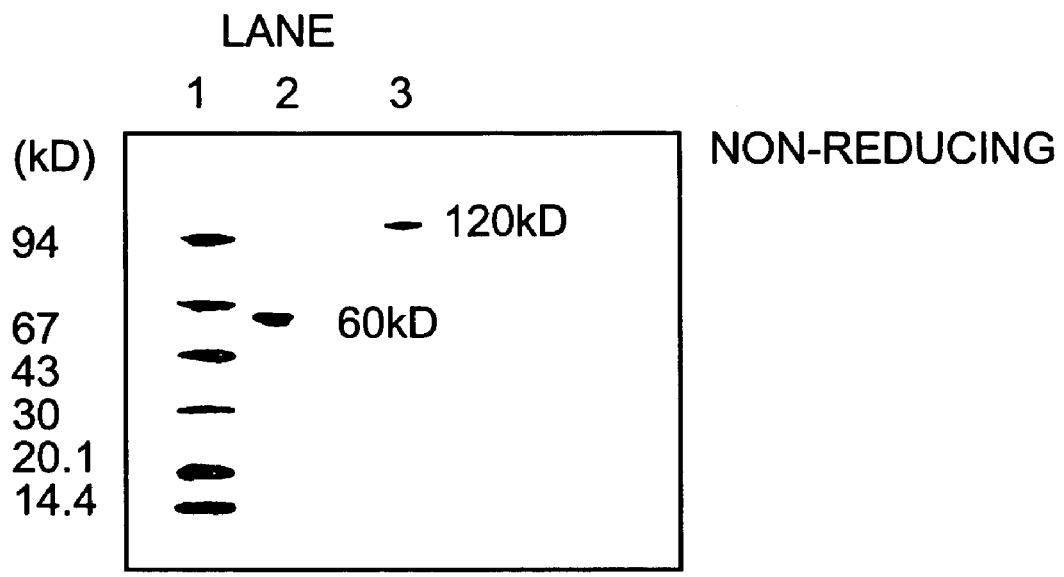
FIGS. 4A and 4B show the SDS-PAGE results of isolated OCIF proteins under reducing or non-reducing conditions. Description of the lanes:
  lane 1, 4: molecular weight marker proteins;
  lane 2, 5: OCIF protein of peak 6 in FIG. 3;
  lane 3, 6: OCIF protein of peak 7 in FIG. 3.
Figure 4B:
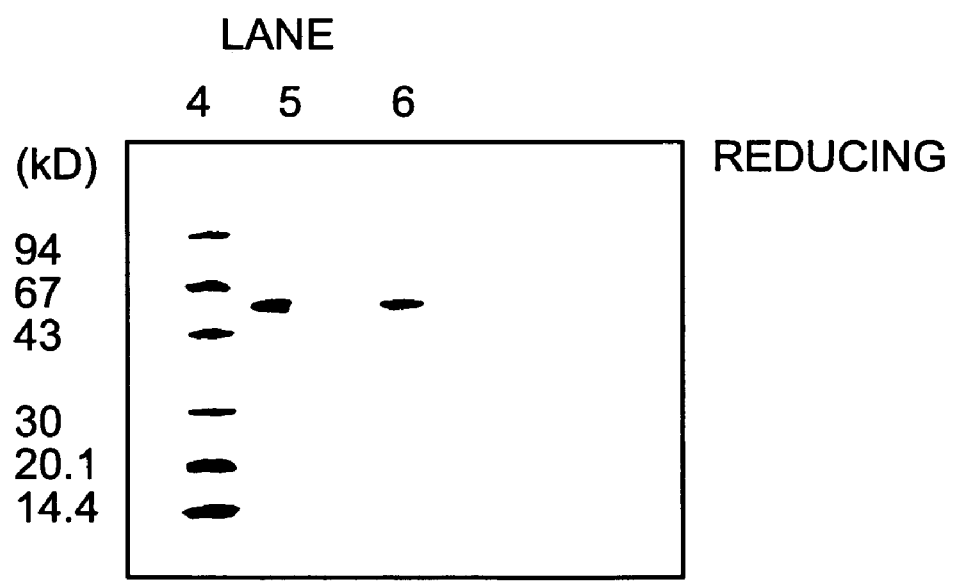
Figure 5:
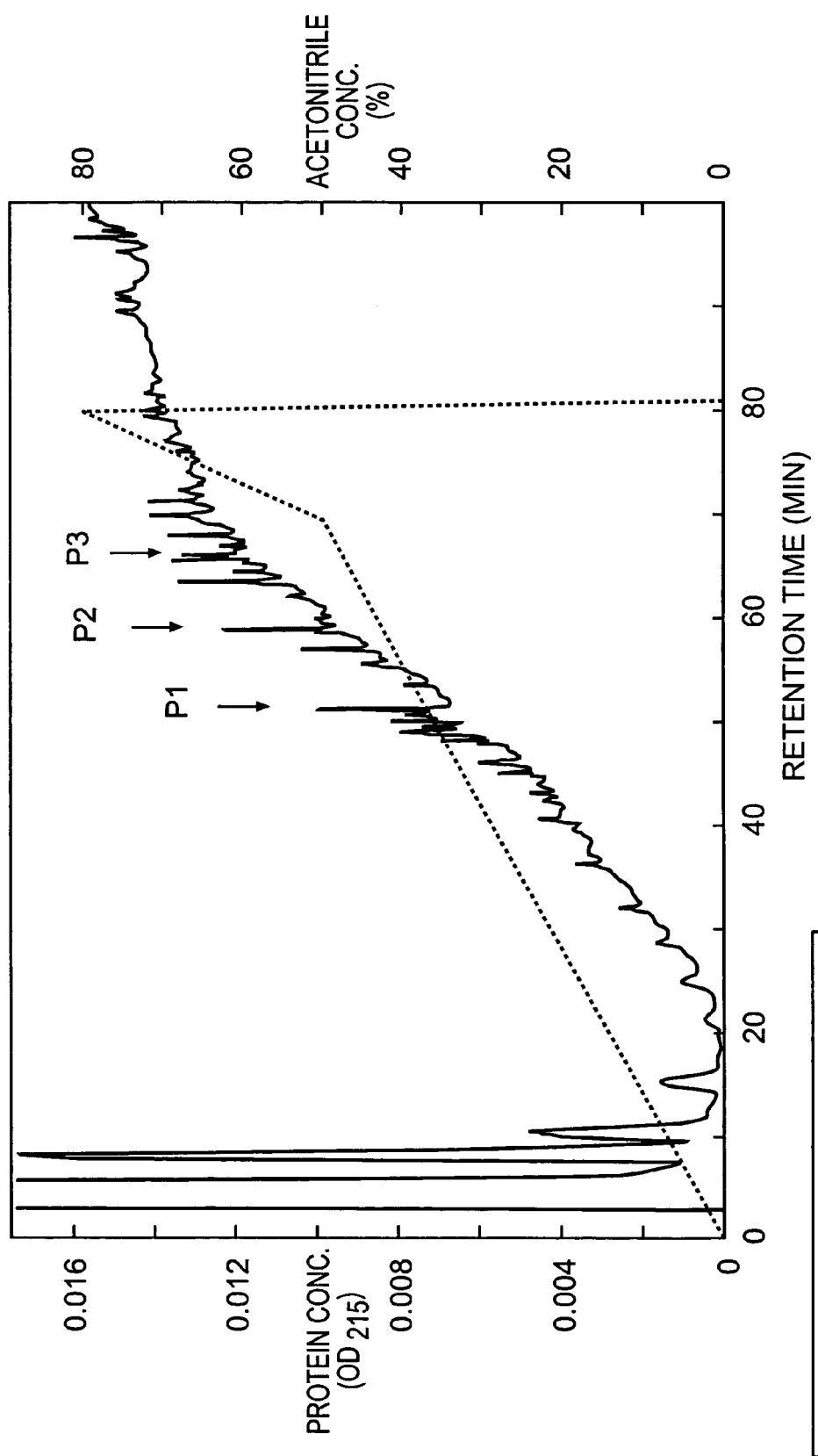
FIG. 5 shows the elution pattern of peptides (peak 7) obtained by the digestion of pyridyl ethylated OCIF protein digested with lysylendopeptidase, on a reverse-phase column.

The two protein peaks with OCIF activity (peaks 6 and 7) were subjected to SDS-polyacrylamide gel electrophoresis under reducing and non-reducing conditions. Briefly, 20 µL of each peak fraction was concentrated under vacuum and dissolved in 1.5 µL of 10 mM Tris-HCl, pH 8, 1 mM EDTA, 2.5% SDS, 0.01% bromophenol blue, and incubated at 37° C. overnight under non-reducing conditions or under reducing conditions (with 5% of 2-mercaptoethanol). Each 1.0 µL of sample was then analyzed by SDS-polyacrylamide gel electrophoresis with a gradient gel of 10-15% acrylamide (Pharmacia Co.) and an electrophoresis-device (Fast System, Pharmacia Co.). The following molecular weight marker proteins were used to calculate molecular weight: phosphorylase b (94 kD), bovine serum albumin (67 kD), ovalbumin (43 kD), carbonic anhydrase (30 kD), trypsin inhibitor (20.0 kD), and lactalbumin (14.4 kD). After electrophoresis, protein bands were visualized by silver stain using Phast Silver Stain Kit. The results are shown in FIG. 4.

A protein band with an apparent molecular weight of 60 kD was detected in the peak 6 sample under both reducing and non-reducing conditions. A protein band with an apparent 60 kD was detected under reducing conditions and a protein band with an apparent 120 kD was detected under non-reducing conditions in the peak 7 sample. Therefore, the protein of peak 7 was considered to be a homodimer of the protein of peak 6.

EXAMPLE 5

Thermostability of OCIF

Twenty µL of sample from the blue-5PW fractions 51 and 52 was diluted to 30 µL with 10 mM phosphate buffered saline, pH 7.2, and incubated for 10 min. at 70° C. or 90° C., or for 30 min. at 56° C. The heat-treated samples were tested for OCIF activity. The results are shown in Table 2.

TABLE 2

Thermostability of OCIF

| Sample | Dilution | | |
|---|---|---|---|
| | 1/300 | 1/900 | 1/2700 |
| Untreated | ++ | + | − |
| 70° C., 10 min | + | − | − |
| 56° C., 30 min | + | − | − |
| 90° C., 10 min | − | − | − |

[++ means OCIF activity inhibiting osteoclast development more than 80%, +means OCIF activity inhibiting osteoclast development between 30% and 80%, and − means no OCIF activity.]

EXAMPLE 6

Internal Amino Acid Sequence of OCIF Protein

Each 2 fractions (1 ml) from fractions 51 to 70 of the blue-5PW fractions were acidified with 10 µL of 25% TFA, and applied to a reverse phase C4 column (BU-300, 2.1×220 mm, manufactured by Perkin-Elmer Co.) equilibrated with 25% acetonitrile containing 0.1% TFA. The adsorbed protein was eluted with a 12 ml linear gradient of 25 to 55% acetonitrile at a flow rate of 0.2 ml/min, and the protein fractions corresponding to peaks 6 and 7 were collected, respectively. The protein from each peak was applied to a protein sequencer (PROCISE™ 494, Perkin-Elmer Co.). However, the N-terminal sequence of the protein of each peak could not be analyzed. Therefore, the N-terminus of the protein of each peak was considered to be blocked. Internal amino acid sequences of these proteins were therefore analyzed.

The protein from peak 6 or 7 purified by C4-HPLC, was concentrated by centrifugation and pyridilethylated under reducing conditions. Briefly, 50 µL of 0.5 M Tris-HCl, pH 8.5, containing 100 µg of dithiothreitol, 10 mM EDTA, 7 M guanidine-HCl, and 1% CHAPS was added to each of the samples, and the mixtures were incubated overnight in the dark at room temperature. Each mixture was acidified with 25% TFA (a final concentration 0.1%) and applied to a reverse phase C4 column (BU300, 2.1×30 mm, Perkin-Elmer Co.) equilibrated with 20% acetonitrile containing 0.1% TFA. The pyridilethylated OCIF protein was eluted with a 9 ml linear gradient from 20 to 50% acetonitrile at a flow rate of 0.3 ml/min, and each protein peak was collected. The pyridil-ethylated OCIF protein was concentrated under vacuum and dissolved in 25 µL of 0.1 M Tris-HCl, pH 9, containing 8 M Urea, and 0.1% TWEEN™ 80. Seventy-three µL of 0.1 M Tris-HCl, pH 9, and 0.02 µg of lysyl endopeptidase (Wako Pure Chemical, Japan) were added to the tube, and incubated at 37° C. for 15 hours. Each digest was acidified with 1 µL of 25% TFA and was applied to a reverse phase C8 column (RP-300, 2.1×220 mm, Perkin-Elmer Co.) equilibrated with 0.1% TFA.

The peptide fragments were eluted from the column with a linear gradient of 0 to 50% acetonitrile at a flow rate of 0.2 ml/min for 70 min., and each peptide peak was collected. Each peptide fragment (P1-P3) was applied to the protein sequencer. The sequences of the peptides are shown in SEQ ID NOs: 1-3, respectively.

EXAMPLE 7

Determination of the Nucleotide Sequence of OCIF cDNA i) Isolation of Poly(A)+RNA from IMR-90 Cells About 10 µg of poly(A)+RNA was isolated from 1×10[8] cells of IMR-90 using a FASTTRACK™ mRNA isolation kit (Invitrogen) according to the manufacturer's instructions.

ii) Preparation of Mixed Primers

The following two mixed primers were synthesized based on the amino acid sequences of two peptides (peptide P2 and peptide P3, SEQ ID NOs: 2 and 3, respectively). All the oligonucleotides in the mixed primers No. 2F (SEQ ID NO: 107) can code for the amino acid sequence from the sixth residue, glutamine (Gln) to the twelfth residue, leucine (Leu), in peptide P2. All the oligonucleotides in the mixed primers No. 3R (SEQ ID NO: 108) can code for the amino acid sequence from the sixth residue, histidine (His), to the twelfth residue, lysine (Lys), in peptide P3. The sequences of the mixed primers No. 2F and No. 3R were shown in Table 3.

TABLE 3

```
No. 2F (SEQ ID NO: 107)
    5'-CAAGAACAAA CTTTTCAATT-3'
        G   G   G    C  C  GC
                     A
                     G

No. 3R (SEQ ID NO: 108)
    5'-TTTATACATT GTAAAAGAAT G-3'
        C  G      C    G  GCTG
           A           C
           G           T
``` iii) Amplification of an OCIF cDNA Fragment by PCR (Polymerase Chain Reaction)

First strand cDNA was generated using a SUPER-SCRIPT™ II cDNA synthesis kit 23 (Gibco BRL) and 1 μg of poly(A)+RNA obtained in EXAMPLE 7-i), according to the manufacturer's instructions. The DNA fragment encoding OCIF was obtained by PCR using cDNA template and the primers shown in EXAMPLE 7-ii).

PCR was performed using the following conditions:

| | |
|---|---|
| 10× Ex Taq Buffer (Takara Shuzo) | 5 μl |
| 2.5 mM solution of dNTPs | 4 μl |
| cDNA solution | 1 μl |
| Ex Taq (Takara Shuzo) | 0.25 μl |
| sterile distilled water | 29.75 μl |
| 40 μM solution of primers No. 2F | 5 μl |
| 40 μM solution of primers No. 3R | 5 μl |

The components of the reaction were mixed in a microcentrifuge tube. An initial denaturation step at 95° C. for 3 min was followed by 30 cycles of denaturation at 95° C. for 30 sec, annealing at 50° C. for 30 sec and extention at 70° C. for 2 min. After the amplification, a final extention step was performed at 70° C. for 5 min. The sizes of the PCR products were determined on a 1.5% agarose gel electrophoresis. An approximately 400 bp OCIF DNA fragment was obtained.

EXAMPLE 8

Cloning of the OCIF cDNA Fragment Amplified by PCR and Determination of its DNA Sequence The OCIF cDNA fragment amplified by PCR in EXAMPLE 7-iii) was inserted into the plasmid pBLUE-SCRIPT II SK™ using a DNA ligation kit ver. 2 (Takara Shuzo) according to the method of Marchuk, D. et al. (Nucleic Acids Res., vol 19, p 1154, 1991). E. coli strain DH5 α (Gibco BRL) was transformed with the ligation mixture. The transformants were grown and a plasmid containing the OCIF cDNA (about 400 bp) was purified using commonly used methods. This plasmid was called pBSOCIF. The sequence of the OCIF cDNA in pBSOCIF was determined using a TAQ DYE DEOXY TERMINATER CYCLE SEQUENCING™ kit (Perkin Elmer). The size of the OCIF cDNA is 397 bp. The OCIF cDNA encodes an amino acid sequence containing 132 residues. The amino acid sequences of the internal peptides (peptide P2 and peptide P3, SEQ ID NOs: 2 and 3, respectively) that were used to design the primers were found at the amino or carboxyl terminus of the 132 amino acid sequence predicted by the 397 bp OCIF cDNA. In addition, the amino acid sequence of the internal peptide P1 (SEQ ID NO: 1) was also found in the predicted amino acid sequence of OCIF. These data show that the 397 bp OCIF cDNA is a portion of the full length OCIF cDNA.

EXAMPLE 9

Preparation of the DNA Probe

The 397 bp OCIF cDNA was prepared according to the conditions described in EXAMPLE 7-iii). The OCIF cDNA was subjected to a preparative agarose gel electrophoresis. The OCIF cDNA was purified from the gel using a QIAEX™ gel extraction kit (QIAGEN), labeled with [$\alpha^{32}$P]dCTP using Megaprime DNA labeling system (Amersham) and used to select a phage containing the full length OCIF cDNA.

EXAMPLE 10

Preparation of the cDNA Library cDNA was generated using a Great Lengths cDNA synthesis kit (Clontech), oligo (dT) primer, [$\alpha^{32}$P]dCTP and 2.5 μg of poly(A)+RNA obtained in EXAMPLE 7-i), according to the manufacturer's instructions. An EcoRI-SalI-NotI adaptor was ligated to the cDNA. The cDNA was separated from free adaptor DNA and unincorporated free [$\alpha^{32}$P]dCTP. The purified cDNA was precipitated with ethanol and dissolved in 10 μL of TE buffer (10 mM Tris-HCl (pH 8.0), 1 mM EDTA). The cDNA comprising the adaptor was ligated into λZAP EXPRESS™ vector (Stratagene) at the EcoRI site. The recombinant λZAP EXPRESS™ phage DNA containing the cDNA was in vitro packaged using a GIGAPACK™ gold # II packaging extract (Stratagene) yielding a recombinant λZAP EXPRESS™ phage library.

EXAMPLE 11

Screening of Recombinant Phage

Recombinant phages obtained in EXAMPLE 10 were used to infect E. coli strain, XL1-Blue MRF' (Stratagene) at 37° C. for 15 min. The infected E. coli cells were added to NZY medium containing 0.7% agar at 50° C. and plated onto NZY agar plates. After the plates were incubated at 37° C. overnight, HYBOND™ N (Amersham) membranes were placed on the surface of the plates containing plaques. The membranes were denatured in alkali solution, neutralized, and washed in 2×SSC according to standard methods. The phage DNA was immobilized onto the membranes using UV CROSSLINK™ (Stratagene). The membranes were incubated in hybridization buffer (Amersham) containing 100 μg/ml salmon sperm DNA at 65° C. for 4 hours and then incubated at 65° C. overnight in the same buffer containing 2×10⁵ cpm/ml of denatured OCIF DNA probe. The membranes were washed twice with 2×SSC and twice with a solution containing 0.1×SSC and 0.1% SDS at 65° C. for 10 min each time. The positive clones were purified by repeating the screening twice. The purified λZAP EXPRESS™ phage clone containing a DNA insert of about 1.6 kb was used in the experiments described below. This phage was called λ OCIF.

The purified λ OCIF was used to infect *E. coli* strain XL-1 blue MRF' (Stratagene) according to the protocol in the λZAP EXPRESS™ cloning kit (Stratagene). The culture broth of infected XL-1 blue MRF' was prepared. Purified λ OCIF and EXASSIST™ helper phage (Stratagene) were coinfected into *E. coil* strain XL-1 blue MRF', according to the protocol supplied with the kit. The culture broth of the coinfected XL-1 blue MRF' was added to a culture of *E. coli* strain XLOR (Stratagene) to transform them. Thus we obtained a Kanamycin-resistant transformant harboring a plasmid designated pBKOCIF which is a pBKCMV (Stratagene) vector containing the 1.6 kb insert fragment.

The transformant including the plasmid containing about 1.6 kb OCIF cDNA was obtained by lifting the Kanamycin-resistant colonies. The plasmid was called pBKOCIF. The transformant has been deposited in the National Institute of Bioscience and Human-Technology (NIBH), Agency of Industrial Science and Technology as "FERM BP-5267" as pBK/01F10. A national deposit (Accession number, FERM P-14998) was transferred to the international deposit, on Oct. 25, 1995 according to the Budapest treaty. The transformant pBK/01F10 was grown and the plasmid pBKOCIF was purified according to standard methods.

EXAMPLE 12

Determination of the Nucleotide Sequence of OCIF cDNA Containing the Full Coding Region.

The nucleotide sequence of OCIF cDNA obtained in EXAMPLE 11 was determined using a TAQ DYE DEOXY TERMINATER CYCLE SEQUENCING™ kit (Perkin Elmer). The primers used were T3, T7 (Stratagene) and synthetic primers designed according to the OCIF cDNA sequence. The sequences of these primers are shown in SEQ ID NOs: 16 to 29. The nucleotide sequence of the OCIF cDNA is shown in SEQ ID NO: 6 and the amino acid sequence predicted by the cDNA sequence is shown in SEQ ID NO: 5.

EXAMPLE 13

Production of Recombinant OCIF by 293/EBNA Cells i) Construction of the Plasmid for Expressing OCIF cDNA pBKOCIF, containing about 1.6 kb OCIF cDNA, was prepared as described in EXAMPLE 11 and digested with restriction enzymes BamHI and XhoI. The OCIF cDNA insert was cut out, isolated by an agarose gel electrophoresis and purified using a QIAEX™ gel extraction kit (QIAGEN). The purified OCIF cDNA insert was ligated into the expression vector pCEP4 (Invitrogen) using DNA ligation kit ver. 2 (Takara Shuzo) digested with restriction enzymes BamHI and XhoI. *E. coli* strain DH5 α (Gibco BRL) was transformed with the ligation mixture.

The transformants were grown and the plasmid containing the OCIF cDNA (about 1.6 kb) was purified using a QIAGEN™ column (QIAGEN). The expression plasmid pCEPOCIF was precipitated with ethanol and dissolved in sterile distilled water for use in the experiments described below.

ii) Transient Expression of OCIF cDNA and Analysis of OCIF Biological Activity

Recombinant OCIF was produced using the expression plasmid pCEPOCIF (prepared in EXAMPLE 13-i) according to the method described below. $8 \times 10^5$ cells of 293/EBNA (Invitrogen) were inoculated into each well of a 6-well plate using IMDM containing 10% fetal bovine serum (FBS; Gibco BRL). After the cells were incubated for 24 hours, the culture medium was removed and the cells were washed with serum free IMDM. The expression plasmid pCEPOCIF and lipofectamine (Gibco BRL) were diluted with OPTI-MEM™ (Gibco BRL), mixed, and added to the cells in each well according to the manufacturer's instructions. Three μg of pCEPOCIF and 12 μL of lipofectamine were used for each transfection. After the cells were incubated with pCEPOCIF and lipofectamine for 38 hours, the medium was replaced with 1 ml of OPTI-MEM™. After incubation for 30 hours, the conditioned medium was harvested and used for the biological assay. The biological activity of OCIF was analyzed according to the method described below. Bone marrow cells obtained from 17 day old mice were suspended in α-MEM™ (manufactured by GIBCO BRL Co.) containing 10% FBS, $1\times10^{-8}$M activated vitamin $D_3$ and a test sample, and were inoculated and cultured for 7 days at 37° C. in humidified 5% $CO_2$ as described in EXAMPLE 2. During incubation, 160 μL of old medium in each well was replaced with the same volume of the fresh medium containing test sample diluted with $1\times10^{-8}$ M of activated vitamin $D_3$ and α-MEM™ containing FBS on day 3 and day 5. On day 7, after washing the wells with phosphate buffered saline, cells were fixed with ethanol/acetone (1:1) for 1 min. and osteoclast development was tested using an acid phosphatase activity measuring kit (Acid Phosphatase, Leucocyte, Catalog No. 387A, Sigma Co.). A decrease in the number of TRAP positive cells was taken as an OCIF activity. The conditioned medium showed the same OCIF activity as natural OCIF protein from IMR-90 conditioned medium (Table 4).

TABLE 4

OCIF activity of 293/EBNA conditioned medium.

| Cultured Cell | Dilution | | | | | | |
|---|---|---|---|---|---|---|---|
| | 1/20 | 1/40 | 1/80 | 1/160 | 1/320 | 1/640 | 1/1280 |
| OCIF expression vector transfected | ++ | ++ | ++ | ++ | ++ | + | − |
| vector transfected | − | − | − | − | − | − | − |
| untreated | − | − | − | − | − | − | − |

[++; OCIF activity inhibiting osteoclast development more than 80%, +; OCIF activity inhibiting osteoclast development between 30% and 80%, and −; no OCIF activity.]

iii) Isolation of Recombinant OCIF Protein from 293/EBNA-conditioned Medium

293/EBNA-conditioned medium (1.8 L) obtained by cultivating the cells described in EXAMPLE 13-ii) was supplemented with 0.1% CHAPS and filtrated using a 0.22 μm membrane filter (Sterivex GS, Millipore Co.). The conditioned medium was applied to a 50 ml heparin SEPHAROSE™ CL-6B column (2.6×10 cm, Pharmacia Co.) equilibrated with 10 mM Tris-HCl, pH 7.5. After washing the column with 10 mM Tris-HCl, pH 7.5, the adsorbed protein was eluted from the column with a linear gradient from 0 to 2 M NaCl at a flow rate of 4 ml/min for 100 min. and 8 ml fractions were collected. Using 150 μL of each fraction, OCIF activity was assayed according to the method described in EXAMPLE 2. An OCIF active 112 ml fraction, eluted with approximately 0.6 to 1.2 M NaCl, was obtained.

One hundred twelve ml of the active fraction was diluted to 1000 ml with 10 mM Tris-HCl, 0.1% CHAPS, pH 7.5, and applied to a heparin affinity column (heparin-5PW, 0.8×7.5 cm, Tosoh Co.) equilibrated with 10 mM Tris-HCl, 0.1% CHAPS, pH 7.5. After washing the column with 10 mM Tris-HCl, 0.1% CHAPS, pH 7.5, the adsorbed protein was eluted from the column with a linear gradient from 0 to 2 M NaCl at a flow rate of 0.5 ml/min for 60 min. and 0.5 ml fractions were collected. Four µL of each fraction was analyzed by SDS-polyacrylamide gel electrophoresis under reducing and non-reducing conditions as described in EXAMPLE 4. A single band of rOCIF protein with an apparent molecular weight of 60 kD was detected in fractions from 30 to 32 by SDS-PAGE under reducing conditions. Bands of rOCIF protein with apparent molecular weights of 60 kD and 120 kD were also detected in fractions from 30 to 32 under non-reducing conditions. The isolated rOCIF from fractions 30 to 32 was designated as recombinant OCIF derived from 293/EBNA (rOCIF(E)). 1.5 ml of the rOCIF(E) (535 µg/ml) was obtained when determined by the method of Lowry, using bovine serum albumin as a standard protein.

EXAMPLE 14

Production of Recombinant OCIF Using CHO Cells
  i) Construction of the Plasmid for Expressing OCIF
  pBKOCIF containing about 1.6 kb OCIF cDNA was prepared as described in EXAMPLE 11, and digested with restriction enzymes SalI and EcoRV. About 1.4 kb OCIF cDNA insert was separated by agarose gel electrophoresis and purified from the gel using a QIAEX™ gel extraction kit (QIAGEN). The expression vector, pcDL-SR α 296 (Molecular and Cellular Biology, vol 8, p 466-472, 1988) was digested with restriction enzymes PstI and KpnI. About 3.4 kb of the expression vector fragment was cut out, separated by agarose gel electrophoresis and purified from the gel using a QIAEX™ gel extraction kit (QIAGEN). The ends of the purified OCIF cDNA insert and the expression vector fragment were blunted using a DNA blunting kit (Takara Shuzo). The purified OCIF cDNA insert and the expression vector fragment were ligated using a DNA ligation kit ver. 2 (Takara Shuzo). *E. coli* strain DH5a α (Gibco BRL) was transformed with the ligation mixture. A transformant containing the OCIF expression plasmid, pSR αOCIF was obtained.
  ii) Preparation of the Expression Plasmid
  The transformant containing the OCIF expression plasmid, pSR αOCIF prepared in EXAMPLE 13-i) and the transformant containing the mouse DHFR expression plasmid, pBAdDSV shown in WO 92/01053 were grown according to standard methods. Both plasmids were purified by alkali treatment, polyethylene glycol precipitation, and cesium chloride density gradient ultra centrifugation according to the method of Maniatis et al. (*Molecular Cloning*, 2nd edition).
  iii) Adaptation of CHOdhFr⁻ Cells to the Protein Free Medium
  CHOdhFr⁻ cells (ATCC, CRL 9096) were cultured in IMDM containing 10% fetal bovine serum. The cells were adapted to EXCELL™ 301 (JRH Bioscience) and then adapted to EXCELL™ PF CHO (JRH Bioscience) according to the manufacturer's instructions.
  iv) Transfection of the OCIF Expression Plasmid, and the Mouse DHFR Expression Plasmid, into CHOdhFr⁻ Cells.
  CHOdhFr⁻ cells prepared in EXAMPLE 14-iii) were transfected by electroporation with pSR αOCIF and pBAdDSV prepared in EXAMPLE 14-ii). Two hundred µg of pSR αOCIF and 20 µg of pBAdDSV were dissolved under sterile conditions in 0.8 ml of IMDM (Gibco BRL) containing 10% fetal bovine serum. CHOdhFr⁻ cells ($2 \times 10^7$) were suspended in 0.8 ml of this medium. The cell suspension was transferred to a cuvette (Bio Rad) and the cells were transfected by electroporation using a GENE PULSER™ (Bio Rad) under the conditions of 360 V and 960 µF. The suspension of electroporated cells was transferred to T-flasks (Sumitomo Bakelite) containing 10 ml of EXCELL™ PF-CHO, and incubated in the $CO_2$ incubator for 2 days. The transfected cells were then inoculated into each well of a 96 well plate (Sumitomo Bakelite) at a density of 5000 cells/well and cultured for about 2 weeks. The transformants expressing DHFR are selected since EXCELL™ PF-CHO does not contain nucleotides and the parental cell line CHOdhFr⁻ can not grow in this medium. Most of the transformants expressing DHFR express OCIF since the OCIF expression plasmid was used ten times as much as the mouse DHFR expression plasmid. The transformants whose conditioned medium had high OCIF activity were selected from among the transformants expressing DHFR according to the method described in EXAMPLE 2. The transformants that express large amounts of OCIF were cloned by the limiting dilution method. The clones whose conditioned medium had high OCIF activity were selected as described above and a transformant expressing large amounts of OCIF named, 5561, was obtained.
  v) Production of Recombinant OCIF
  To produce recombinant OCIF (rOCIF), clone 5561 was inoculated into a 3 L spinner flask with EXCELL™ 301 medium (3 L) at a cell density of $1 \times 10^5$ cells/ml. The 5561 cells were cultured in a spinner flask at 37° C. for 4 to 5 days. When the concentration of the 5561 cells reached $1 \times 10^6$ cells/ml, about 2.7 L of the conditioned medium was harvested. Then about 2.7 L of EXCELL™ 301 was added to the spinner flask and the 5561 cells were cultured repeatedly.

About 20 L of the conditioned medium was harvested using the three spinner flasks.
  vi) Isolation of Recombinant OCIF Protein from CHO Cell-conditioned Medium
  CHO cell-conditioned medium (1.0 L) described in EXAMPLE 14-v) was supplemented with 1.0 g CHAPS and filtrated with a 0.22 µm membrane filter (Sterivex-GS, Millipore Co.). The conditioned medium was applied to a heparin SEPHAROSE™-FF column (2.6×10 cm, Pharmacia Co.) equilibrated with 10 mM Tris-HCl, pH 7.5. After washing the column with 10 mM Tris-HCl, 0.1% CHAPS, pH 7.5, the adsorbed protein was eluted from the column with a linear gradient from 0 to 2 M NaCl at a flow rate of 4 ml/min for 100 min. and 8 ml fractions were collected. Using 150 µL of each fraction, OCIF activity was assayed according to the method described in EXAMPLE 2. An active fraction (112 ml) eluted with approximately 0.6 to 1.2 M NaCl was obtained.

The 112 ml active fraction was diluted to 1200 ml with 10 mM Tris-HCl, 0.1% CHAPS, pH 7.5, and applied to an affinity column (Blue-5PW, 0.5×5.0 cm, Tosoh Co.) equilibrated with 10 mM Tris-HCl, 0.1% CHAPS, pH 7.5. After washing the column with 10 mM Tris-HCl, 0.1% CHAPS, pH 7.5, the adsorbed protein was eluted from the column with a linear gradient from 0 to 3 M NaCl at a flow rate of 0.5 ml/min for 60 min. and fractions (0.5 ml) were collected. Four µL of each fraction were subjected to SDS-polyacrylamide gel electrophoresis under reducing and non-reducing conditions as described in EXAMPLE 4. A single band of rOCIF protein with an apparent molecular weight of 60 kD was detected in fractions 30 to 38 using SDS-PAGE under reducing conditions. Bands of rOCIF protein with apparent molecular weights of 60 kD and 120 kD using SDS-PAGE under non-reducing conditions were also detected in fractions 30 to 38. The isolated rOCIF fraction, from fractions 30 to 38, was designated as purified recombinant OCIF derived from CHO cells (rOCIF(C)). 4.5 ml of the rOCIF(C) (113 µg/ml) was obtained, as determined by the method of Lowry using bovine serum albumin as a standard protein.

EXAMPLE 15

Determination of N-terminal Amino Acid Sequence of rOCIFs

Three μg of the isolated rOCIF(E) and rOCIF(C) were adsorbed to polyvinylidene difluoride (PVDF) membranes with PROSPIN™ (PERKIN ELMER Co.). The membranes were washed with 20% ethanol and the N-terminal amino acid sequences of the adsorbed proteins were analyzed by protein sequencer (PROCISE™ 492, PERKIN ELMER Co.). The determined N-terminal amino acid sequence is shown in SEQ ID NO: 7.

The N-terminal amino acid of rOCIF(E) and rOCIF(C) was glutamic acid located at position 22 from Met of the translation start site, as shown in SEQ ID NO: 5. The 21 amino acids from Met to Gln were identified as a signal peptide. The N-terminal amino acid sequence of OCIF isolated from IMR-90 conditioned medium could not be determined. Accordingly, the N-terminal glutamic acid of OCIF may be blocked by the conversion of glutamic acid to pyroglutamine within cell culture or purification steps.

EXAMPLE 16

Biological Activity of Recombinant (r) OCIF and Natural (n) OCIF i) Inhibition of Vitamin $D_3$ Induced Osteoclast Formation in Murine Bone Marrow Cells Each of the rOCIF(E) and nOCIF samples were diluted with α-MEM™ (GIBCO BRL Co.) containing 10% FBS and $2\times10^{-8}$ M of activated vitamin $D_3$ (a final concentration of 250 ng/ml). Each sample was serially diluted with the same medium, and 100 μL of each diluted sample was added to each well of a 96-well plate. Bone marrow cells obtained from 17 day old mice were inoculated at a cell density of $3\times10^5$ cells/100 μL/well into each well of a 96-well plate and cultured for 7 days at 37° C. in humidified 5% $CO_2$. On day 7, the cells were fixed and stained with an acid phosphatase measuring kit (Acid Phosphatase, Leucocyte, No. 387-A, Sigma) according to the method described in EXAMPLE 2. A decrease in acid phosphatase activity (TRAP) was taken as an indication of OCIF activity. A decrease in acid phosphatase-positive cells was evaluated by solubilizing the pigment of dye and measuring absorbance. Briefly, 100 μL of a mixture of 0.1 N NaOH and dimethylsulfoxide (1:1) was added to each well and the well was vibrated to solubilize the dye. After solubilizing the dye completely, an absorbance of each well was measured at 590 nm, subtracting the absorbance at 490 nm using a microplate reader (IMMUNOREADER™ NJ-2000, InterMed). The microplate reader was adjusted to 0 absorbance using a well with monolayered bone marrow cells which were cultured in the medium without activated vitamin $D_3$. A decrease in TRAP activity was expressed as a percentage of the control absorbance value (=100%) (measured for wells with bone marrow cells cultured in the absence of OCIF). The results are shown in Table 5.

TABLE 5

Inhibition of vitamin D3-induced osteoclast formation from murine bone marrow cells

| OCIF concentration(ng/ml) | 250 | 125 | 63 | 31 | 16 | 0 |
|---|---|---|---|---|---|---|
| rOCIF(E) | 0 | 0 | 3 | 62 | 80 | 100 |
| nOCIF | 0 | 0 | 27 | 27 | 75 | 100 (%) |

Both nOCIF and rOCIF(E) inhibited osteoclast formation in a dose dependent manner at concentrations of 16 ng/ml or greater.

ii) Inhibition of Vitamin $D_3$-induced Osteoclast Formation in Co-cultures of Stromal Cells and Mouse Spleen Cells.

The effect of OCIF on osteoclast formation induced by Vitamin $D_3$ in co-cultures of stromal cells and mouse spleen cells was tested according to the method of N. Udagawa et al. (Endocrinology, vol. 125, p 1805-1813, 1989). Briefly, samples of each of rOCIF(E), rOCIF(C), and nOCIF were serially diluted with α-MEM™ (GIBCO BRL Co.) containing 10% FBS, $2\times10^{-8}$ M activated vitamin $D_3$ and $2\times10^{-7}$ M dexamethasone and 100 μL of each of the diluted samples was added to each well of 96 well-microwell plates. Murine bone marrow-derived stromal ST2 cells (RIKEN Cell Bank RCB0224) at $5\times10^3$ cells per 100 μL of α-MEM™ containing 10% FBS and spleen cells from 8 week old ddy mice at $1\times10^5$ cells per 100 μL in the same medium, were inoculated into each well of a 96-well plate and cultured for 5 days at 37° C. in humidified 5% $CO_2$. On day 5, the cells were fixed and stained using an acid phosphatase kit (Acid Phosphatase, Leucocyte, No. 387-A, Sigma). A decrease in acid phosphatase-positive cells was taken as an indication of OCIF activity. The decrease in acid phosphatase-positive cells was evaluated according to the method described in EXAMPLE 16-i). The results are shown in Table 6 (rOCIF(E) and rOCIF(C)) and Table 7 (rOCIF(E) and nOCIF).

TABLE 6

Inhibition of osteoclast formation in co-cultures of stromal cells and mouse spleen cells.

| OCIF concentration(ng/ml) | 50 | 25 | 13 | 6 | 0 |
|---|---|---|---|---|---|
| rOCIF(E) | 3 | 22 | 83 | 80 | 100 |
| rOCIF(C) | 13 | 19 | 70 | 96 | 100 (%) |

TABLE 7

Inhibition of osteoclast formation in co-cultures of stromal cells and mouse spleen cells.

| OCIF concentration(ng/ml) | 250 | 63 | 16 | 0 |
|---|---|---|---|---|
| rOCIF(E) | 7 | 27 | 37 | 100 |
| rOCIF(C) | 13 | 23 | 40 | 100 (%) | nOCIF, rOCIF(E) and rOCIF(C) inhibited osteoclast formation in a dose dependent manner at concentrations of 6-16 ng/ml or greater.

iii) Inhibition of PTH-induced Osteoclast Formation in Murine Bone Marrow Cells.

The effect of OCIF on osteoclast formation induced by PTH was tested according to the method of N. Takahashi et al. (Endocrinology, vol. 122, p 1373-1382, 1988). Briefly, samples of each of rOCIF(E) and nOCIF (125 ng/ml) were serially diluted with α-MEM™ (manufactured by GIBCO BRL Co.) containing 10% FBS and $2\times10^{-8}$ M PTH, and 100 μL of each of the diluted samples was added to the wells of 96 well-plates. Bone marrow cells from 17 day old ddy mice at a cell density of $3\times10^5$ cells per 100 μL of α-MEM™ containing 10% FBS were inoculated into each well of a 96-well plate and cultured for 5 days at 37° C. in humidified 5% $CO_2$. On day 5, the cells were fixed with ethanol/acetone (1:1) for 1 min. at room temperature and stained with an acid phosphatase kit (Acid Phosphatase, Leucocyte, No. 387-A, Sigma) according to the method described in EXAMPLE 2. A decrease in acid phosphatase-positive cells was taken as an indication of OCIF activity. The decrease in acid phosphatase-positive cells was evaluated according to the method described in EXAMPLE 16-i). The results are shown in Table 8.

TABLE 8

Inhibition of PTH-induced osteoclast formation from murine bone marrow cells.

| OCIF concentration(ng/ml) | 125 | 63 | 31 | 16 | 8 | 0 |
|---|---|---|---|---|---|---|
| rOCIF(E) | 6 | 58 | 58 | 53 | 88 | 100 |
| nOCIF | 18 | 47 | 53 | 56 | 91 | 100 | nOCIF and rOCIF(E) inhibited osteoclast formation in a dose dependent manner at concentrations of 16 ng/ml or greater.

iv) Inhibition of IL-11-induced Osteoclast Formation

The effect of OCIF on osteoclast formation induced by IL-11 was tested according to the method of T. Tamura et al. (Proc. Natl. Acad. Sci. USA, vol. 90, p 11924-11928, 1993). Briefly, samples of each of rOCIF(E) and nOCIF were serially diluted with α-MEM™ (GIBCO BRL Co.) containing 10% FBS and 20 ng/ml IL-11 and 100 µl of each diluted sample was added to each well in a 96-well plate. Newborn mouse calvaria-derived pre-adipocyte MC3T3-G2/PA6 cells (RIKEN Cell Bank RCB1127) at $5 \times 10^3$ cells per 100 µl of α-MEM™ containing 10% FBS, and spleen cells from 8 week old ddy mouse, at $1 \times 10^5$ cells per 100 µL in the same medium, were inoculated into each well of a 96-well plate and cultured for 5 days at 37° C. in humidified 5% $CO_2$. On day 5, the cells were fixed and stained with an acid phosphatase kit (Acid Phosphatase, Leucocyte, No. 387-A, Sigma). Acid phosphatase positive cells were counted under a microscope and a decrease of the cell numbers was taken as an indication of OCIF activity. The results are shown in Table 9.

TABLE 9

| OCIF concentration(ng/ml) | 500 | 125 | 31 | 7.8 | 2.0 | 0.5 | 0 |
|---|---|---|---|---|---|---|---|
| nOCIF | 0 | 0 | 1 | 4 | 13 | 49 | 31 |
| rOCIF(E) | 0 | 0 | 1 | 3 | 10 | 37 | 31 |

Both nOCIF and rOCIF(E) inhibited osteoclast formation in a dose dependent manner at concentrations of 2 ng/ml or greater.

The results shown in Tables 4-8 indicated that OCIF inhibits all the vitamin $D_3$, PTH, and IL-11-induced osteoclast formations at almost the same doses. Accordingly, OCIF could be used for treating different types of bone disorders due to decreased bone mass, that are caused by different substances that induce bone resorption.

EXAMPLE 17

Isolation of Monomer-type OCIF and Dimer-type OCIF

Each rOCIF(E) and rOCIF(C) sample containing 100 µg of OCIF protein, was supplemented with 1/100 volume of 25% trifluoro acetic acid and applied to a reverse phase column (PROTEIN-RP™, 2.0×250 mm, YMC Co.) equilibrated with 30% acetonitrile containing 0.1% trifluoro acetic acid. OCIF protein was eluted from the column with a linear gradient from 30 to 55% acetonitrile at a flow rate of 0.2 ml/min for 50 min. and each OCIF peak was collected. The monomer-type OCIF peak fraction and dimer-type OCIF peak fraction were each lyophilized.

EXAMPLE 18

Determination of the Molecular Weight of Recombinant OCIFs

Figure 6:
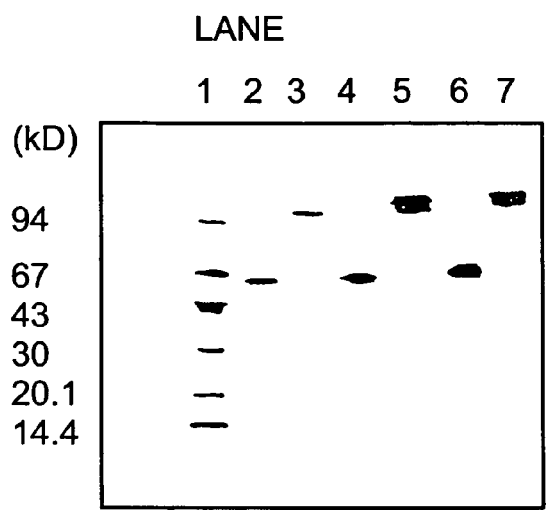
FIG. 6 shows the SDS-PAGE results of isolated natural (n) OCIF protein and recombinant (r) OCIF proteins under non-reducing conditions. rOCIF (E) and rOCIF (C) proteins were produced by 293/EBNA cells and by CHO cells, respectively. Description of the lanes:
  lane 1: molecular weight marker proteins;
  lane 2: a monomer type nOCIF protein;
  lane 3: a dimer type nOCIF protein;
  lane 4: a monomer type rOCIF (E) protein;
  lane 5: a dimer type rOCIF (E) protein;
  lane 6: a monomer type rOCIF (C) protein;
  lane 7: a dimer type rOCIF (C) protein.
Figure 7:
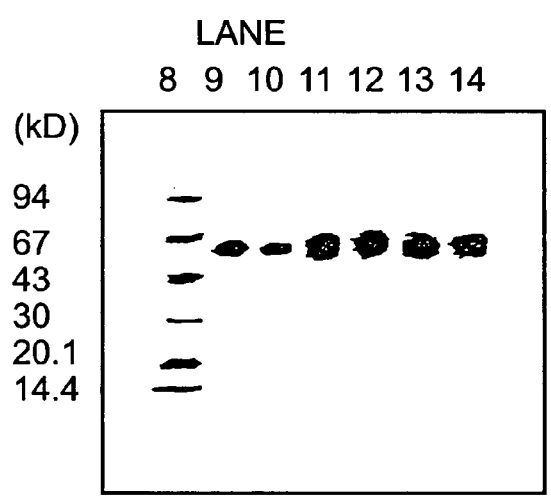
FIG. 7 shows the SDS-PAGE results of isolated natural (n) OCIF proteins and recombinant (r) OCIF proteins under reducing conditions. rOCIF (E) and rOCIF (C) were produced by 293/EBNA cells and by CHO cells, respectively. Description of the lanes:
  lane 8: molecular weight marker proteins;
  lane 9: a monomer type nOCIF protein;
  lane 10: a dimer type nOCIF protein;
  lane 11: a monomer type rOCIF (E) protein;
  lane 12: a dimer type rOCIF (E) protein;
  lane 13: a monomer type rOCIF (C) protein;
  lane 14: a dimer type rOCIF (C) protein.

Each 1 µg of the isolated monomer-type and dimer-type nOCIF purified using a reverse phase column according to EXAMPLE 3-iv) and each 1 µg of monomer-type and dimer-type rOCIF described in EXAMPLE 17 was concentrated under vacuum. Each sample was incubated in the buffer for SDS-PAGE, subjected to SDS-polyacrylamide gel electrophoresis, and protein bands on the gel were stained with silver according to the method described in EXAMPLE 4. Results of electrophoresis under non-reducing conditions and reducing conditions are shown in FIGS. 6 and 7, respectively.

A protein band with an apparent molecular weight of 60 kD was detected in each monomer-type OCIF sample, and a protein band with an apparent molecular weight of 120 kD was detected in each dimer-type OCIF sample under non-reducing conditions. A protein band with an apparent molecular weight of 60 kD was detected in each monomer-type OCIF sample under reducing conditions. Accordingly, the molecular weights of monomer-type nOCIF from IMR-90 cells, rOCIF from 293/EBNA cells and rOCIF from CHO cells were almost the same (60 kD). Molecular weights of dimer-type nOCIF from IMR-90 cells, rOCIF from 293/EBNA cells, and rOCIF from CHO cells were also the same (120 kD).

EXAMPLE 19

Figure 8:
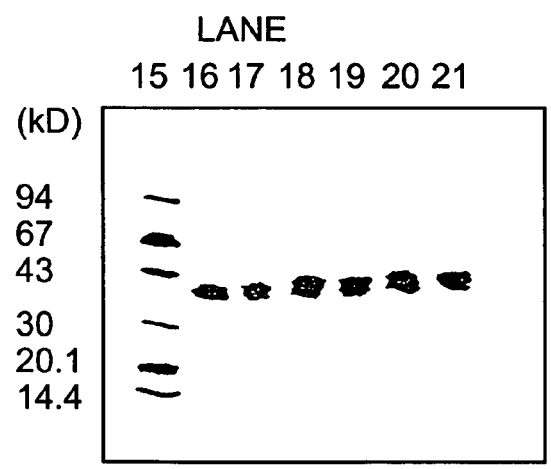
FIG. 8 shows the SDS-PAGE results of isolated natural (n) OCIF proteins and recombinant (r) OCIF proteins from which N-linked sugar chains were removed under reducing conditions. rOCIF (E) and rOCIF (C) are rOCIF proteins produced by 293/EBNA cells and by CHO cells, respectively. Description of the lanes:
  lane 15: molecular weight marker proteins;
  lane 16: a monomer type nOCIF protein;
  lane 17: a dimer type nOCIF protein;
  lane 18: a monomer type rOCIF (E) protein;
  lane 19: a dimer type rOCIF (E) protein;
  lane 20: a monomer type rOCIF (C) protein;
  lane 21: a dimer type rOCIF (C) protein.

Removal of the N-linked Oligosaccharide Chain and Measuring the Molecular Weight of Natural and Recombinant OCIF Each sample containing 5 µg of the isolated monomer-type and dimer-type nOCIF purified using a reverse phase column according to EXAMPLE 3-iv) and each sample containing 5 µg of monomer-type and dimer-type rOCIF described in EXAMPLE 17 were concentrated under vacuum. Each sample was dissolved in 9.5 µL of 50 mM sodium phosphate buffer, pH 8.6, containing 100 mM 2-mercaptoethanol, supplemented with 0.5 µL of 250 U/ml N-glycanase (Seikagaku kogyo Co.) and incubated for one day at 37° C. Each sample was supplemented with 10 µL of 20 mM Tris-HCl, pH 8.0 containing 2 mM EDTA, 5% SDS, and 0.02% bromophenol blue and heated for 5 min at 100° C. Each 1 µL of the samples was subjected to SDS-polyacrylamide gel electrophoresis, and protein bands on the gel were stained with silver as described in EXAMPLE 4. The patterns of electrophoresis are shown in FIG. 8.

An apparent molecular weight of each of the deglycosylated nOCIF from IMR-90 cells, rOCIF from CHO cells, and rOCIF from 293/EBNA cells was 40 kD under reducing conditions. An apparent molecular weight of each of the untreated nOCIF from IMR-90 cells, rOCIF from 293/EBNA cells, and rOCIF from CHO cells was 60 kD under reducing conditions. Accordingly, the results indicate that the OCIF proteins are glycoproteins with N-linked sugar chains.

EXAMPLE 20

Cloning of OCIF Variant cDNAs and Determination of their DNA Sequences

The plasmid pBKOCIF, comprising OCIF cDNA inserted into plasmid pBKCMV (Stratagene), was obtained as in EXAMPLES 10 and 11. Further, during the screening of the cDNA library with the 397 bp OCIF cDNA probe, the transformants containing plasmids whose insert sizes were different from that of pBKOCIF were obtained. These transformants containing the plasmids were grown and the plasmids were purified according to the standard method. The sequence of the insert DNA in each plasmid was determined using a TAQ DYE DEOXY TERMINATER CYCLE SEQUENCING™ kit (Perkin Elmer). The primers used were T3, T7, (Stratagene) and synthetic primers prepared based on the nucleotide sequence of OCIF cDNA. There are four OCIF variants (OCIF2, 3, 4, and 5) in addition to OCIF. The nucleotide sequence of OCIF2 is shown in SEQ ID NO: 8 and the amino acid sequence of OCIF2 predicted by the nucleotide sequence is shown in SEQ ID NO: 9. The nucleotide sequence of OCIF3 is shown in SEQ ID NO: 10 and the amino acid sequence of OCIF3 predicted by the nucleotide sequence is shown in SEQ ID NO: 11. The nucleotide sequence of OCIF4 is shown in SEQ ID NO: 12 and the amino acid sequence of OCIF4 predicted by the nucleotide sequence is shown in SEQ ID NO: 13. The nucleotide sequence of OCIF5 is shown in SEQ ID NO: 14 and the amino acid sequence of OCIF5 predicted by the nucleotide sequence is shown in SEQ ID NO: 15. The structures of OCIF variants are shown in FIGS. 9 to 12 and are briefly described below.

OCIF2

The OCIF2 cDNA has a deletion of 21 bp from guanine at nucleotide number 265 to guanine at nucleotide number 285 in the OCIF cDNA (SEQ ID NO: 6).

Accordingly, OCIF2 has a deletion of 7 amino acids from glutamic acid (Glu) at amino acid number 89 to glutamine (Gln) at amino acid number 95 in OCIF (SEQ ID NO: 5).

OCIF3

The OCIF3 cDNA has a point mutation at nucleotide number 9 in the OCIF cDNA (SEQ ID NO: 6) where cytidine is replaced with guanine. Accordingly, OCIF3 has a mutation where asparagine (Asn) at amino acid number 3 in OCIF (SEQ ID NO: 5) is replaced with lysine (Lys). The mutation seems to be located in the signal sequence and has no essential effect on the secretion of OCIF3. OCIF3 cDNA has a deletion of 117 bp from guanine at nucleotide number 872 to cytidine at nucleotide number 988 in the OCIF cDNA (SEQ ID NO: 6).

Accordingly, OCIF3 has a deletion of 39 amino acids from threonine (Thr) at amino acid number 291 to leucine (Leu) at amino acid number 329 in OCIF (SEQ ID NO: 5).

OCIF4

The OCIF4 cDNA has two point mutations in the OCIF cDNA (SEQ ID NO: 6). Cytidine at nucleotide number 9 is replaced with guanine and guanine at nucleotide number 22 is replaced with thymidine in the OCIF cDNA (SEQ ID NO: 6).

Accordingly, OCIF4 has two mutations. Asparagine (Asn) at amino acid number 3 in OCIF (SEQ ID NO: 5) is replaced with lysine (Lys), and alanine (Ala) at amino acid number 8 is replaced with serine (Ser). These mutations seem to be located in the signal sequence and have no essential effect on the secreted OCIF4.

The OCIF4 cDNA has about 4 kb DNA, comprising intron 2 of the OCIF gene, inserted between nucleotide number 400 and nucleotide number 401 in the OCIF cDNA (SEQ ID NO: 6). The open reading frame stops in intron 2.

Accordingly, OCIF4 has an additional novel amino acid sequence containing 21 amino acids after alanine (Ala) at amino acid number 133 in OCIF (SEQ ID NO: 5).

OCIF5

The OCIF5 cDNA has a point mutation at nucleotide number 9 in the OCIF cDNA (SEQ ID NO: 6) where cytidine is replaced with guanine.

Accordingly, OCIF5 has a mutation where asparagine (Asn) at amino acid number 3 in OCIF (SEQ ID NO: 5) is replaced with lysine (Lys). The mutation seems to be located in the signal sequence and has no essential effect on the secretion of OCIF5.

The OCIF5 cDNA has the latter portion (about 1.8 kb) of intron 2 between nucleotide number 400 and nucleotide number 401 in OCIF cDNA (SEQ ID NO: 6). The open reading frame stops in the latter portion of intron 2.

Accordingly, OCIF5 has an additional novel amino acid sequence containing 12 amino acids after alanine (Ala) at amino acid number 133 in OCIF (SEQ ID NO: 5).

EXAMPLE 21

Production of OCIF Variants i) Construction of the Plasmid for Expressing OCIF Variants Plasmids containing OCIF2 or OCIF3 cDNA were obtained as described in EXAMPLE 20 and called pBKOCIF2 and pBKOCIF3, respectively. pBKOCIF2 and pBKOCIF3 were digested with restriction enzymes BamHI and XhoI. The OCIF2 and OCIF3 cDNA inserts were separated by agarose gel electrophoresis and purified from the gel using a QIAEX™ gel extraction kit (QIAGEN). The purified OCIF2 and OCIF3 cDNA inserts were individually ligated using a DNA ligation kit ver. 2 (Takara Shuzo) to the expression vector pCEP4 (Invitrogen) that had been digested with restriction enzymes BamHI and XhoI. $E.\ coli$ strain DH5 α (Gibco BRL) was transformed with the ligation mixture.

The plasmid containing OCIF4 cDNA was obtained as described in EXAMPLE 20 and called pBKOCIF4. pBKOCIF4 was digested with restriction enzymes SpeI and XhoI (Takara Shuzo). The OCIF4 cDNA insert was separated by agarose gel electrophoresis, and purified from the gel using a QIAEX™ gel extraction kit (QIAGEN). The purified OCIF4 cDNA insert was ligated using a DNA ligation kit ver. 2 (Takara Shuzo) to an expression vector pCEP4 (Invitrogen) that had been digested with restriction enzymes NheI and XhoI (Takara Shuzo). $E.\ coli$ strain DH5 α (Gibco BRL) was transformed with the ligation mixture.

The plasmid containing OCIF5 cDNA was obtained as described in EXAMPLE 20 and called pBKOCIF5. pBKOCIF5 was digested with the restriction enzyme HindIII (Takara Shuzo). The 5' portion of the coding region in the OCIF5 cDNA insert was separated by agarose gel electrophoresis and purified from the gel using QIAEX™ gel extraction kit (QIAGEN). The OCIF expression plasmid, pCEPOCIF, obtained in EXAMPLE 13-i) was digested with the restriction enzyme HindIII (Takara Shuzo). The 5' portion of the coding region in the OCIF cDNA was removed. The rest of the plasmid that contains pCEP vector and the 3' portion of the coding region of OCIF cDNA was called pCEPOCIF-3'. pCEPOCIF-3' was separated by agarose gel electrophoresis and purified from the gel using a QIAEX™ gel extraction kit (QIAGEN). The OCIF5 cDNA HindIII fragment and pCEPOCIF-3' were ligated using a DNA ligation kit ver. 2 (Takara Shuzo). $E.\ coli$ strain DH5 α (Gibco BRL) was transformed with the ligation mixture.

The transformants obtained were grown at 37° C. overnight and the OCIF variant expression plasmids (pCEPOCIF2, pCEPOCIF3, pCEPOCIF4, and pCEPOCIF5) were purified using QIAGEN™ columns (QIAGEN). These OCIF-variant-expression plasmids were precipitated with ethanol, dissolved in sterile distilled water, and used in the experiments described below.

23 ii) Transient Expression of OCIF Variant cDNAs and Analysis of the Biological Activity of Recombinant OCIF Variants.

Recombinant OCIF variants were produced using the expression plasmids, pCEPOCIF2, pCEPOCIF3, pCEPO-CIF4, and pCEPOCIF5 as described in EXAMPLE 21-i) according to the method described in EXAMPLE 13-ii). The biological activities of recombinant OCIF variants were analyzed. The results were that these OCIF variants (OCIF2, OCIF3, OCIF4, and OCIF5) had weak activity.

EXAMPLE 22

Preparation of OCIF Mutants i) Construction of a Plasmid Vector for Subcloning cDNAs Encoding OCIF Mutants The plasmid vector (5 µg) described in EXAMPLE 11 was digested with restriction enzymes BamHI and XhoI (Takara Shuzo). The digested DNA was subjected to preparative agarose gel electrophoresis. A DNA fragment with an approximate size of 1.6 kilobase pairs (kb) that contained the entire coding sequence for OCIF was purified from the gel using a QIAEX™ gel extraction kit (QIAGEN). The purified DNA was dissolved in 20 µL of sterile distilled water. This solution was designated DNA solution 1. pBLUESCRIPT II SK+™ (3 µg) (Stratagene) was digested with restriction enzymes BamHI and XhoI (Takara Shuzo). The digested DNA was subjected to preparative agarose gel electrophoresis. A DNA fragment with an approximate size of 3.0 kb was purified from the gel using a QIAEX™ DNA extraction kit (QIAGEN). The purified DNA was dissolved in 20 µL of sterile distilled water. This solution was designated DNA solution 2. One microliter of DNA solution 2, 4 µL of DNA solution 1 and 5 µL of ligation buffer I from a DNA ligation kit ver. 2 (Takara Shuzo) were mixed and incubated at 16° C. for 30 min. (The ligation mixture was used in the transformation of E. coli in the manner described below). Conditions for transformation of E. coli were as follows. One hundred microliters of competent E. coli strain DH5 α cells (GIBCO BRL) and 5 µL of the ligation mixture were mixed in a sterile 15-ml tube (IWAKI glass). The tube was kept on ice for 30 min. After incubation for 45 sec at 42° C., 250 µL of L broth (1% Tryptone, 0.5% yeast extract, 1% NaCl) was added to the cells. The cell suspension was then incubated for 1 hr. at 37° C. with shaking. Fifty microliters of the cell suspension was plated onto an L-agar plate containing 5 µg/ml of ampicillin. The plate was incubated overnight at 37° C.

Six colonies which grew on the plate were each incubated in 2 ml of L-broth containing 50 µg/ml ampicillin overnight at 37° C. with shaking. The structure of the plasmids in the colonies was analyzed. A plasmid in which the 1.6-kb DNA fragment containing the entire OCIF cDNA is inserted between the digestion sites of BamHI and XhoI of pBLUE-SCRIPT II SK+™ was obtained and designated as pSK+-OCIF.

ii) Preparation of Mutants in which One of the Cys Residues in OCIF is Replaced with a Ser Residue 1) Introduction of Mutations into OCIF cDNA OCIF mutants were prepared in which one of the five Cys residues present in OCIF at positions 174, 181, 256, 298 and 379 (in SEQ ID NO: 4) was replaced with a Ser residue and were designated OCIF-C19S (174Cys to Ser), OCIF-C20S (181Cys to Ser), OCIF-C21S (256Cys to Ser), OCIF-C22S (298Cys to Ser) and OCIF-C23S (379Cys to Ser), respectively. The amino acid sequences of these mutants are provided in the sequence listing as SEQ ID NOs: 62, 63, 64, 65, and 66, respectively.

24

To prepare the mutants, nucleotides encoding the corresponding Cys residues were replaced with those encoding Ser. Mutagenesis was carried out by a two-step polymerase chain reaction (PCR). The first step of the PCRs consisted of two reactions, PCR 1 and PCR 2.

| PCR 1 | 10× Ex Taq Buffer (Takara Shuzo) | 10 µl |
|---|---|---|
| | 2.5 mM solution of dNTPs | 8 µl |
| | the plasmid vector described in EXAMPLE 11 (8 ng/ml) | 2 µl |
| | sterile distilled water | 73.5 µl |
| | 20 µM solution of primer 1 | 5 µl |
| | 100 µM solution of primer 2 (for mutagenesis) | 1 µl |
| | Ex Taq (Takara Shuzo) | 0.5 µl |
| PCR 2 | 10× Ex Taq Buffer (Takara Shuzo) | 10 µl |
| | 2.5 mM solution of dNTPs | 8 µl |
| | the plasmid vector described in EXAMPLE 11 (8 ng/ml) | 2 µl |
| | sterile distilled water | 73.5 µl |
| | 20 µM solution of primer 3 | 5 µl |
| | 100 µM solution of primer 4 (for mutagenesis) | 1 µl |
| | Ex Taq (Takara Shuzo) | 0.5 µl |

Specific sets of primers were used for each mutation and other components were unchanged. Primers used for the reactions are shown in Table 10. The nucleotide sequences of the primers are shown in SEQ ID NOs: 20, 23, 27 and 30-40. The PCRs were performed under the following conditions. An initial denaturation step at 97° C. for 3 min was followed by 25 cycles of denaturation at 95° C. for 1 min, annealing at 55° C. for 1 min and extension at 72° C. for 3 min. After these amplification cycles, final extension was performed at 70° C. for 5 min. The sizes of the PCR products were confirmed by agarose gel electrophoresis of the reaction solutions. After the first PCR, excess primers were removed using an Amicon MICROCON™ (Amicon). The final volume of the solutions that contained the PCR products were made to 50 µL with sterile distilled water. These purified PCR products were used for the second PCR (PCR 3).

| PCR 3 | 10× Ex Taq Buffer (Takara Shuzo) | 10 µl |
|---|---|---|
| | 2.5 mM solution of DNTPs | 8 µl |
| | solution containing DNA fragment obtained from PCR 1 | 5 µl |
| | solution containing DNA fragment obtained from PCR 2 | 5 µl |
| | sterile distilled water | 61.5 µl |
| | 20 µM solution of primer 1 | 5 µl |
| | 20 µM solution of primer 3 | 5 µl |
| | Ex Taq (Takara Shuzo) | 0.5 µl |

TABLE 10

| mutants | primer-1 | primer-2 | primer-3 | primer-4 |
|---|---|---|---|---|
| OCIF-C19S | IF 10 | C19SR | IF 3 | C19SF |
| OCIF-C20S | IF 10 | C20SR | IF 3 | C20SF |
| OCIF-C21S | IF 10 | C21SR | IF 3 | C21SF |
| OCIF-C22S | IF 10 | C22SR | IF 14 | C22SF |
| OCIF-C23S | IF 6 | C23SR | IF 14 | C23SF |

The reaction conditions were exactly the same as those for PCR 1 or PCR 2. The sizes of the PCR products were confirmed by 1.0% or 1.5% agarose gel electrophoresis. The DNA fragments were precipitated with ethanol, dried under vacuum and dissolved in 40 µL of sterile distilled water. The solutions containing DNA fragments with mutations C19S, C20S, C21S, C22S and C23S were designated as DNA solution A, DNA solution B, DNA solution C, DNA solution D and DNA solution E, respectively.

The DNA fragment which is contained in solution A (20 µL) was digested with restriction enzymes NdeI and SphI (Takara Shuzo). A DNA fragment with an approximate size of 400 base pairs (bp) was extracted from a preparative agarose gel and dissolved in 20 µL of sterile distilled water. This DNA solution was designated DNA solution 3. Two micrograms of pSK+-OCIF were digested with restriction enzymes NdeI and SphI. A DNA fragment with an approximate size of 4.2 kb was purified from a preparative agarose gel using a QIAEX™ gel extraction kit and dissolved in 20 µL of sterile distilled water. This DNA solution was designated DNA solution 4. Two microliters of DNA solution 3, 3 µL of DNA solution 4 and 5 µL of ligation buffer I from a DNA ligation kit ver. 2 were mixed and the ligation reaction was carried out. Competent E. coli strain DH5α cells were transformed with 5 µL of the ligation mixture. Ampicillin-resistant transformants were screened for a clone containing plasmid DNA. DNA structure was analyzed by restriction enzyme mapping and by DNA sequencing. The plasmid thus obtained was named pSK-OCIF-C19S.

The DNA fragment contained in solution B (20 µL) was digested with restriction enzymes NdeI and SphI. A DNA fragment with an approximate size of 400 bp was extracted from a preparative agarose gel using a QIAEX™ gel extraction kit and dissolved in 20 µL of sterile distilled water. This DNA solution was designated DNA solution 5. Two microliters of DNA solution 5, 3 µL of DNA solution 4 and 5 µL of ligation buffer I from a DNA ligation kit ver. 2 were mixed and the ligation reaction was carried out. Competent E. coli strain DH5α cells were transformed with 5 µL of the ligation mixture. Ampicillin-resistant transformants were screened for a clone containing plasmid DNA. DNA structure was analyzed by restriction enzyme mapping and by DNA sequencing. The plasmid thus obtained was named pSK-OCIF-C20S.

The DNA fragment which is contained in solution C (20 µL) was digested with restriction enzymes NdeI and SphI. A DNA fragment with an approximate size of 400 bp was extracted from a preparative agarose gel using a QIAEX™ gel extraction kit and dissolved in 20 µL of sterile distilled water. This DNA solution was designated DNA solution 6. Two microliters of DNA solution 6, 3 µL of DNA solution 4 and 5 µL of ligation buffer I from a ligation kit ver. 2 were mixed and the ligation reaction was carried out. Competent E. coli strain DH5α cells were transformed with 5 µL of the ligation mixture. Ampicillin-resistant transformants were screened for a clone containing plasmid DNA. DNA structure was analyzed by restriction enzyme mapping and by DNA sequencing. The plasmid thus obtained was named pSK-OCIF-C21S.

The DNA fragment which is contained in solution D (20 µL) was digested with restriction enzymes NdeI and BstPI. A DNA fragment with an approximate size of 600 bp was extracted from a preparative agarose gel using a QIAEX™ gel extraction kit and dissolved in 20 µL of sterile distilled water. This DNA solution was designated DNA solution 7. Two micrograms of pSK+-OCIF were digested with restriction enzymes NdeI and BstPI. A DNA fragment with an approximate size of 4.0 kb was extracted from a preparative agarose gel using a QIAEX™ gel extraction kit and dissolved in 20 µL of sterile distilled water. This DNA solution was designated DNA solution 8. Two microliters of DNA solution 7, 3 µL of DNA solution 8 and 5 µL of ligation buffer I from a DNA ligation kit ver. 2 were mixed and the ligation reaction was carried out. Competent E. Coli strain DH5α cells were transformed with 5 µL of the ligation mixture. Ampicillin-resistant transformants were screened for a clone containing plasmid DNA in which the 600-bp NdeI-BstPI fragment with the mutation (the C22S mutation) is substituted for the 600-bp NdeI-BstPI fragment of pSK+-OCIF by analyzing the DNA structure. DNA structure was analyzed by restriction enzyme mapping and by DNA sequencing. The plasmid thus obtained was named pSK-OCIF-C22S.

The DNA fragment which is contained in solution E (20 µL) was digested with restriction enzymes BstPI and EcoRV. A DNA fragment with an approximate size of 120 bp was extracted from a preparative agarose gel using a QIAEX™ gel extraction kit and dissolved in 20 µL of sterile distilled water. This DNA solution was designated DNA solution 9. Two micrograms of pSK+-OCIF were digested with restriction enzymes BstEII and EcoRV. A DNA fragment with an approximate size of 4.5 kb was extracted from a preparative agarose gel using a QIAEX™ gel extraction kit and dissolved in 20 µL of sterile distilled water. This DNA solution was designated DNA solution 10. Two microliters of DNA solution 9, 3 µL of DNA solution 10 and 5 µL of ligation buffer I from a DNA ligation kit ver. 2 were mixed and the ligation reaction was carried out. Competent E. coli strain DH5α cells were transformed with 5 µL of the ligation mixture. Ampicillin-resistant transformants were screened for a clone containing plasmid DNA. DNA structure was analyzed by restriction enzyme mapping and by DNA sequencing. The plasmid thus obtained was named pSK-OCIF-C23S.

2) Construction of Vectors for Expressing the OCIF Mutants pSK-OCIF-C19S, pSK-OCIF-C20S, pSK-OCIF-C21S, pSK-OCIF-C22S and pSK-OCIF-C23S were digested with restriction enzymes BamHI and XhoI. The 1.6 kb BamHI-XhoI DNA fragment encoding each OCIF mutant was isolated and dissolved in 20 µL of sterile distilled water. The DNA solutions that contain 1.6 kb cDNA fragments derived from pSK-OCIF-C19S, pSK-OCIF-C20S, pSK-OCIF-C21S, pSK-OCIF-C22S and pSK-OCIF-C23S were designated C19S DNA solution, C20S DNA solution, C21S DNA solution, C22S DNA solution and C23S DNA solution, respectively. Five micrograms of expression vector pCEP 4 (Invitrogen) were digested with restriction enzymes BamHI and XhoI. A DNA fragment with an approximate size of 10 kb was purified and dissolved in 40 µL of sterile distilled water. This DNA solution was designated as pCEP 4 DNA solution. One microliter of pCEP 4 DNA solution and 6 µL of either C19S DNA solution, C20S DNA solution, C21S DNA solution, C22S DNA solution or C23S DNA solution were independently mixed with 7 µL of ligation buffer I from a DNA ligation kit ver. 2 and the ligation reactions were carried out. Competent E. coli strain DH5α cells (100 µL) were transformed with 7 µL of each ligation mixture. Ampicillin-resistant transformants were screened for clones containing plasmid in which a 1.6-kb cDNA fragment is inserted between the recognition sites of BamHI and XhoI of pCEP 4 by analyzing the DNA structure. The plasmids which were obtained containing the cDNA encoding OCIF-C19S, OCIF-C20S, OCIF-C21S, OCIF-C22S and OCIF-C23S (SEQ ID NOs: 83, 84, 85, 86, and 87, respectively) were designated pCEP4-OCIF-C19S, pCEP4-OCIF-C20S, pCEP4-OCIF-C21S, pCEP4-OCIF-C22S and pCEP4-OCIF-C23S, respectively.

iii) Preparation of Domain-deletion Mutants of OCIF (1) Deletion Mutagenesis of OCIF cDNA A series of OCIF mutants with deletions from Thr 2 to Ala 42, from Pro 43 to Cys 84, from Glu 85 to Lys 122, from Arg 123 to Cys 164, from Asp 177 to Gln 251 or from Ile 252 to His 326 were prepared (positions of the amino acid residues are shown in SEQ ID NO: 4). These mutants were designated as OCIF-DCR1, OCIF-DCR2, OCIF-DCR3, OCIF-DCR4, OCIF-DDD1 and OCIF-DDD2, respectively, and assigned SEQ ID NOs: 67, 68, 69, 70, 71, and 72, respectively.

Mutagenesis was performed by two-step PCR as described in EXAMPLE 22-ii). The primer sets for the reactions are shown in Table 11 and the nucleotide sequences of the primers are shown in SEQ ID NOs: 19, 25, 40-53 and 54.

TABLE 11

| mutants | primer-1 | primer-2 | primer-3 | primer-4 |
|---|---|---|---|---|
| OCIF-DCR1 | XhoI F | DCR1R | IF 2 | DCR1F |
| OCIF-DCR2 | XhoI F | DCR2R | IF 2 | DCR2F |
| OCIF-DCR3 | XhoI F | DCR3R | IF 2 | DCR3F |
| OCIF-DCR4 | XhoI F | DCR4R | IF 16 | DCR4F |
| OCIF-DDD1 | IF 8 | DDD1R | IF 14 | DDD1F |
| OCIF-DDD2 | IF 8 | DDD2R | IF 14 | DDD2F |

The final PCR products were precipitated with ethanol, dried under vacuum and dissolved in 40 μL of sterile distilled water. Solutions of DNA fragments coding for portions of OCIF-DCR1, OCIF-DCR2, OCIF-DCR3, OCIF-DCR4, OCIF-DDD1 and OCIF-DDD2 were designated DNA solutions F, G, H, I, J and K, respectively.

The DNA fragment contained in solution F (20 μL) was digested with restriction enzymes NdeI and XhoI. A DNA fragment with an approximate size of 500 bp was extracted from a preparative agarose gel using a QIAEX™ gel extraction kit and dissolved in 20 μL of sterile distilled water. This DNA solution was designated DNA solution 11. Two micrograms of pSK+-OCIF were digested with restriction enzymes NdeI and XhoI. A DNA fragment with an approximate size of 4.0 kb was extracted from a preparative agarose gel using a QIAEX™ gel extraction kit and dissolved in 20 μL of sterile distilled water. This DNA solution was designated DNA solution 12. Two microliters of DNA solution 11, 3 μL of DNA solution 12 and 5 μL of ligation buffer I from a DNA ligation kit ver. 2 were mixed and the ligation was carried out. Competent *E. coli* strain DH5 α cells were transformed with 5 μL of the ligation mixture. Ampicillin-resistant transformants were screened for a clone containing plasmid DNA. DNA structure was analyzed by restriction enzyme mapping and by DNA sequencing. The plasmid thus obtained was named pSK-OCIF-DCR1.

The DNA fragment which is contained in solution G (20 μL) was digested with restriction enzymes NdeI and XhoI. A DNA fragment with an approximate size of 500 bp was extracted from a preparative agarose gel using a QIAEX™ gel extraction kit and dissolved in 20 μL of sterile distilled water. This DNA solution was designated DNA solution 13. Two microliters of DNA solution 13, 3 μL of DNA solution 12 and 5 μL of ligation buffer I from a DNA ligation kit ver. 2 were mixed and ligation was carried out. Competent *E. coli* strain DH5 α cells were transformed with 5 μL of the ligation mixture. Ampicillin-resistant transformants were screened for a clone containing a plasmid DNA. DNA structure was analyzed by restriction enzyme mapping and by DNA sequencing. The plasmid thus obtained was named pSK-OCIF-DCR2.

The DNA fragment contained in solution H (20 μL) was digested with restriction enzymes NdeI and XhoI. A DNA fragment with an approximate size of 500 bp was extracted from a preparative agarose gel using a QIAEX™ gel extraction kit and dissolved in 20 μL of sterile distilled water. This DNA solution was designated DNA solution 14. Two microliters of DNA solution 14, 3 μL of DNA solution 12 and 5 μL of ligation buffer I from a DNA ligation kit ver. 2 were mixed and the ligation reaction was carried out. Competent *E. coli* strain DH5 α cells were transformed with 5 μL of the ligation mixture. Ampicillin-resistant transformants were screened for a clone containing a plasmid DNA. DNA structure was analyzed by restriction enzyme mapping and by DNA sequencing. The plasmid thus obtained was named pSK-OCIF-DCR3.

The DNA fragment contained in solution I (20 μL) was digested with restriction enzymes XhoI and SphI. A DNA fragment with an approximate size of 900 bp was extracted from a preparative agarose gel using a QIAEX™ gel extraction kit and dissolved in 20 μL of sterile distilled water. This DNA solution was designated DNA solution 15. Two micrograms of pSK+-OCIF were digested with restriction enzymes XhoI and SphI. A DNA fragment with an approximate size of 3.6 kb was extracted from a preparative agarose gel using a QIAEX™ gel extraction kit and dissolved in 20 μL of sterile distilled water. This DNA solution was designated DNA solution 16. Two microliters of DNA solution 15, 3 μL of DNA solution 16 and 5 μL of ligation buffer I from a DNA ligation kit ver. 2 were mixed and the ligation reaction was carried out. Competent *E. coli* strain DH5 α cells were transformed with 5 μL of the ligation mixture. Ampicillin-resistant transformants were screened for a clone containing plasmid DNA. DNA structure was analyzed by restriction enzyme mapping and by DNA sequencing. The plasmid thus obtained was named pSK-OCIF-DCR4.

The DNA fragment contained in solution J (20 μL) was digested with restriction enzymes BstPI and NdeI. A DNA fragment with an approximate size of 400 bp was extracted from a preparative agarose gel using a QIAEX™ gel extraction kit and dissolved in 20 μL of sterile distilled water. This DNA solution was designated DNA solution 17. Two microliters of DNA solution 17, 3 μL of DNA solution 8 and 5 μL of ligation buffer I from a DNA ligation kit ver. 2 were mixed and the ligation reaction was carried out. Competent *E. coli* strain DH5 α cells were transformed with 5 μL of the ligation mixture. Ampicillin-resistant transformants were screened for a clone containing plasmid DNA. DNA structure was analyzed by restriction enzyme mapping and by DNA sequencing. The plasmid thus obtained was named pSK-OCIF-DDD1.

The DNA fragment contained in solution K (20 μL) was digested with restriction enzymes NdeI and BstPI. A DNA fragment with an approximate size of 400 bp was extracted from a preparative agarose gel using a QIAEX™ gel extraction kit and dissolved in 20 μL of sterile distilled water. This DNA solution was designated DNA solution 18. Two microliters of DNA solution 18, 3 μL of DNA solution 8 and 5 μL of ligation buffer I from a DNA ligation kit ver. 2 were mixed and the ligation reaction was carried out. Competent *E. coli* strain DH5 α cells were transformed with 5 μL of the ligation mixture. Ampicillin-resistant transformants were screened for a clone containing plasmid DNA. DNA structure was analyzed by restriction enzyme mapping and by DNA sequencing. The plasmid thus obtained was named pSK-OCIF-DDD2.

2) Construction of Vectors for Expressing the OCIF Mutants pSK-OCIF-DCR1, pSK-OCIF-DCR2, pSK-OCIF-DCR3, pSK-OCIF-DCR4, pSK-OCIF-DDD1 and pSK-OCIF-DDD2 were digested with restriction enzymes BamHI and XhoI. The BamHI-XhoI DNA fragment containing the entire coding sequence for each OCIF mutant was isolated and dissolved in 20 µL of sterile distilled water. These DNA solutions that contain the BamHI-XhoI fragment derived from pSK-OCIF-DCR1, pSK-OCIF-DCR2, pSK-OCIF-DCR3, pSK-OCIF-DCR4, pSK-OCIF-DDD1 and pSK-OCIF-DDD2 were designated DCR1 DNA solution, DCR2 DNA solution, DCR3 DNA solution, DCR4 DNA solution, DDD1 DNA solution and DDD2 DNA solution, respectively. One microliter of pCEP 4 DNA solution and 6 µL of either DCR1 DNA solution, DCR2 DNA solution, DCR3 DNA solution, DCR4 DNA solution, DDD1 DNA solution or DDD2 DNA solution were independently mixed with 7 µL of ligation buffer I from a DNA ligation kit ver. 2 and the ligation reactions were carried out. Competent E. coli strain DH5 α cells (100 µL) were transformed with 7 µL of each ligation mixture. Ampicillin-resistant transformants were screened for a clone containing plasmid DNA in which the DNA fragment with deletions is inserted between the recognition sites of BamHI and XhoI of pCEP 4 by analyzing the DNA structure. The plasmids containing the cDNA encoding OCIF-DCR1, OCIF-DCR2, OCIF-DCR3, OCIF-DCR4, OCIF-DDD1 and OCIF-DDD2 (SEQ ID NOs: 88, 89, 90, 91, 92, and 93, respectively) were designated pCEP4-OCIF-DCR1, pCEP4-OCIF-DCR2, pCEP4-OCIF-DCR3, pCEP4-OCIF-DCR4, pCEP4-OCIF-DDD1 and pCEP4-OCIF-DDD2, respectively.

iv) Preparation of OCIF with C-terminal Domain Truncation (1) Mutagenesis of OCIF cDNA A series of OCIF mutants with deletions from Cys at amino acid residue 379 to Leu 380, from Ser 331 to Leu 380, from Asp 252 to Leu 380, from Asp 177 to Leu 380, from Arg 123 to Leu 380 and from Cys 86 to Leu 380 was prepared. Positions of the amino acid residues are shown in SEQ ID NO: 4. These mutants were designated as OCIF-CL, OCIF-CC, OCIF-CDD2, OCIF-CDD1, OCIF-CCR4 and OCIF-CCR3, respectively, and assigned SEQ ID NOs: 73, 74, 75, 76, 77, and 78, respectively.

Mutagenesis for OCIF-CL was performed by the two-step PCR as described in EXAMPLE 22-ii). The primer set for the reaction is shown in Table 12. The nucleotide sequences of the primers are shown in SEQ ID NOs: 23, 40, 55, and 66. The final PCR products were precipitated with ethanol, dried under vacuum and dissolved in 40 µL of sterile distilled water. This DNA solution was designated solution L.

The DNA fragment contained in solution L (20 µL) was digested with restriction enzymes BstPI and EcoRV. A DNA fragment with an approximate size of 100 bp was extracted from a preparative agarose gel using a QIAEX™ gel extraction kit and dissolved in 20 µL of sterile distilled water. This DNA solution was designated DNA solution 19. Two microliters of DNA solution 19, 3 µL of DNA solution 10 (described in EXAMPLE 22-ii)) and 5 µL of ligation buffer I from a DNA ligation kit ver. 2 were mixed and ligation reaction was carried out. Competent E. coli strain DH5 α cells were transformed with 5 µL of the ligation mixture. Ampicillin-resistant transformants were screened for a clone containing plasmid DNA. DNA structure was analyzed by restriction enzyme mapping and by DNA sequencing. The plasmid thus obtained was named pSK-OCIF-CL. Mutagenesis of OCIF cDNA to prepare OCIF-CC, OCIF-CDD2, OCIF-CDD1, OCIF-CCR4 and OCIF-CCR3 was performed by a one-step PCR reaction.

PCR reactions for mutagenesis to prepare OCIF-CC, OCIF-CDD2, OCIF-CDD1, OCIF-CCR4 and OCIF-CCR3 were as follows:

| | |
|---|---|
| 10× Ex Taq Buffer (Takara Shuzo) | 10 µl |
| 2.5 mM solution of dNTPs | 8 µl |
| the plasmid vector containing the entire OCIF cDNA described in EXAMPLE 11 (8 ng/ml) | 2 µl |
| sterile distilled water | 73.5 µl |
| 20 µM solution of primer OCIF Xho F | 5 µl |
| 100 µM solution of primer (for mutagenesis) | 1 µl |
| Ex Taq (Takara Shuzo) | 0.5 µl |

TABLE 12

| mutants | primer-1 | primer-2 | primer-3 | primer-4 |
|---|---|---|---|---|
| OCIF-CL | IF 6 | CL R | IF 14 | CL F |

Specific primers were used for each mutagenesis and other components were unchanged.

Primers used for the mutagenesis are shown in Table 13. Their nucleotide sequences are shown in SEQ ID NOs: 57-61. The components of each PCR were mixed in a microcentrifuge tube and PCR was performed as follows. The microcentrifuge tubes were treated for 3 minutes at 97° C. and then incubated sequentially, for 30 seconds at 95° C., 30 seconds at 50° C. and 3 minutes at 70° C. This three-step incubation procedure was repeated 25 times, and after that, the tubes were incubated for 5 minutes at 70° C. An aliquot of the reaction mixture was removed from each tube and analyzed by agarose gel electrophoresis to confirm the size of each product.

Excess primers in the PCRs were removed using an Amicon MICROCON™ (Amicon) after completion of the reaction. The DNA fragments were precipitated with ethanol, dried under vacuum and dissolved in 40 µL of sterile distilled water. The DNA fragment in each DNA solution was digested with restriction enzymes XhoI and BamHI. After the reactions, DNA was precipitated with ethanol, dried under vacuum and dissolved in 20 µL of sterile distilled water.

The solutions containing the DNA fragment with the CC deletion, the CDD2 deletion, the CDD1 deletion, the CCR4 deletion and the CCR3 deletion were designated CC DNA solution, CDD2 DNA solution, CDD1 DNA solution, CCR4 DNA solution and CCR3 DNA solution, respectively.

TABLE 13

| mutants | primers for the mutagenesis |
|---|---|
| OCIF-CC | CC R |
| OCIF-CDD2 | CDD2 R |
| OCIF-CDD1 | CDD1 R |
| OCIF-CCR4 | CCR4 R |
| OCIF-CCR3 | CCR3 R |

(2) Construction of Vectors for Expressing the OCIF Mutants pSK-OCIF-CL was digested with restriction enzymes BamHI and XhoI. The BamHI-XhoI DNA fragment containing the entire coding sequence for OCIF-CL was isolated and dissolved in 20 µL of sterile distilled water. This DNA solution was designated CL DNA solution. One microliter of pCEP 4 DNA solution and 6 µL of either CL DNA solution, CC DNA solution, CDD2 DNA solution, CDD1 DNA solution, CCR4 DNA solution or CCR3 DNA solution were independently mixed with 7 µL of ligation buffer I from a DNA ligation kit ver. 2 and the ligation reactions were carried out. Competent *E. coli* strain DH5α cells (100 µL) were transformed with 7 µL of each ligation mixture. Ampicillin-resistant transformants were screened for clones containing plasmids which have the desirable mutations in the OCIF cDNA by analyzing the DNA structure. In each plasmid, the OCIF cDNA fragment having a deletion was inserted between the recognition sites of XhoI and BamHI of pCEP 4. The plasmids containing the cDNA encoding OCIF-CL, OCIF-CC, OCIF-CDD1, OCIF-CDD2, OCIF-CCR4 and OCIF-CCR3 (SEQ ID NOs: 94, 95, 96, 97, 98, and 99, respectively) were designated pCEP4-OCIF-CL, pCEP4-OCIF-CC, pCEP4-OCIF-CDD2, pCEP4-OCIF-CDD1, pCEP4-OCIF-CCR4 and pCEP4-OCIF-CCR3, respectively.

v) Preparation of OCIF Mutants with C-terminal Truncations (1) Introduction of C-terminal Truncations to OCIF A series of OCIF mutants with C-terminal truncations was prepared. An OCIF mutant in which 10 residues from Gln at 371 to Leu at 380 were replaced with 2 residues (Leu-Val) was designated OCIF-CBst (SEQ ID NO: 79). An OCIF mutant in which 83 residues from Cys 298 to Leu 380 were replaced with 3 residues (Ser-Leu-Asp) was designated OCIF-CSph (SEQ ID NO: 80). An OCIF mutant in which 214 residues from Asn 167 to Leu 380 were removed was designated OCIF-CBsp (SEQ ID NO: 81). An OCIF mutant in which 319 residues from Asp 62 to Leu 380 were replaced with 2 residues (Leu-Val) was designated OCIF-CPst (SEQ ID NO: 82). Positions of the amino acid residues are shown in SEQ ID NO: 4.

Two micrograms each of pSK+-OCIF were digested with BstPI, SphI, PstI (Takara Shuzo) or BspEI (New England Biolabs) followed by phenol extraction and ethanol precipitation. The precipitated DNA was dissolved in 10 µL of sterile distilled water. The ends of the DNAs in 2 µL of each solution were blunted using a DNA blunting kit in a final volume of 5 µL. To the reaction mixtures, 1 µg (1 µL) of an Amber codon-containing XbaI linker (5'-CTAGTCTAGACTAG-3') and 6 µL of ligation buffer I from a DNA ligation kit ver. 2 were added.

After the ligation reactions, 6 µL each of the reaction mixtures was used to transform *E. coli* strain DH5 α. Ampicillin-resistant transformants were screened for clones containing plasmids. DNA structure was analyzed by restriction enzyme mapping and by DNA sequencing. The plasmids thus obtained were named pSK-OCIF-CBst, pSK-OCIF-CSph, pSK-OCIF-CBsp and pSK-OCIF-CPst, respectively.

(2) Construction of Vectors Expressing the OCIF Mutants pSK-OCIF-CBst, pSK-OCIF-CSph, pSK-OCIF-CBsp and pSK-OCIF-CPst were digested with restriction enzymes BamHI and XhoI. The 1.5 kb DNA fragment containing the entire coding sequence for each OCIF mutant was isolated and dissolved in 20 µL of sterile distilled water. These DNA solutions that contained the BamHI-XhoI fragment derived from pSK-OCIF-CBst, pSK-OCIF-CSph, pSK-OCIF-CBsp or pSK-OCIF-CPst were designated CBst DNA solution, CSph DNA solution, CBsp DNA solution and CPst DNA solution, respectively. One microliter of pCEP 4 DNA solution (described in EXAMPLE 22-ii)) and 6 µL of either CBst DNA solution, CSph DNA solution, CBsp DNA solution or CPst DNA solution were independently mixed with 7 µL of ligation buffer I from a DNA ligation kit ver. 2 and the ligation reactions were carried out. Competent *E. coli* strain DH5 α cells (100 µL) were transformed with 7 µL of each ligation mixture. Ampicillin-resistant transformants were screened for clones containing plasmids in which the cDNA fragment was inserted between the recognition sites of BamHI and XhoI of pCEP 4 by analyzing the DNA structure. The plasmids containing the cDNA encoding OCIF-CBst, OCIF-CSph, OCIF-CBsp or OCIF-CPst (SEQ ID NOs: 100, 101, 102, and 103, respectively) were designated pCEP4-OCIF-CBst, pCEP4-OCIF-CSph, pCEP4-OCIF-CBsp and pCEP4-OCIF-CPst, respectively.

vi) Preparation of Vectors for Expressing the OCIF Mutants

*E. Coli* clones harboring the expression vectors for OCIF mutants (a total of 21 clones) were grown and the vectors were purified by using QIAGEN™ columns (QIAGEN). All the expression vectors were precipitated with ethanol and dissolved in appropriate volumes of sterile distilled water and used for further manipulations shown below.

vii) Transient Expression of the cDNAs for OCIF Mutants and Biological Activities of the Mutants OCIF mutants were produced using the expression vectors prepared in EXAMPLE 22-vi). The method was essentially the same as described in EXAMPLE 13. Only the modified points are described below. $2 \times 10^5$ cells of 293/EBNA suspended in IMDM containing 10% fetal bovine serum were seeded into each well of a 24 well plate. One microgram of purified vector DNA and 4 µL of lipofectamine were used for each transfection. A mixture of the expression vector and lipofectamine in OPTI-MEM™ (GIBCO BRL) in a final volume of 0.5 ml was added to the cells in a well. After the cells were incubated at 37° C. for 24 hr in 5% $CO_2$, the medium was replaced with 0.5 ml of EXCELL™ 301 medium (JSR). The cells were incubated at 37° C. for a further 48 hours in 5% $CO_2$. The conditioned medium was collected and used in assays for in vitro biological activity. The nucleotide sequences of cDNAs for the OCIF mutants are shown in SEQ ID NOs: 83-103. The deduced amino acid sequences for the OCIF mutants are shown in SEQ ID NOs: 62-82. The assay for in vitro biological activity was performed as described in EXAMPLE 13. The antigen concentration of each conditioned medium was determined by ELISA as described in EXAMPLE 24. Table 14 shows the activity of each mutant relative to that of the unaltered OCIF.

TABLE 14

| mutants | activity |
| --- | --- |
| the unaltered OCIF | ++ |
| OCIF-C19S | + |
| OCIF-C20S | ± |
| OCIF-C21S | ± |
| OCIF-C22S | + |
| OCIF-C23S | ++ |
| OCIF-DCR1 | ± |
| OCIF-DCR2 | ± |
| OCIF-DCR3 | ± |
| OCIF-DCR4 | ± |
| OCIF-DDD1 | + |
| OCIF-DDD2 | ± |
| OCIF-CL | ++ |
| OCIF-CC | ++ |
| OCIF-CDD2 | ++ |
| OCIF-CDD1 | + |
| OCIF-CCR4 | ± |
| OCIF-CCR3 | ± |
| OCIF-CBst | ++ |
| OCIF-CSph | ++ |
| OCIF-CBsp | ± |
| OCIF-CPst | ± |

++ indicates relative activity more than 50% of that of the unaltered OCIF;
+ indicates relative activity between 10% and 50%;
± indicates relative activity less than 10%, or production level too low to determine the accurate biological activity.

viii) Western Blot Analysis

Ten microliters of the final conditioned medium was used for western blot analysis. Ten microliters of each sample were mixed with 10 µL of SDS-PAGE sample buffer (0.5 M Tris-HCl, 20% glycerol, 4% SDS, 20 µg/ml bromophenol blue, pH 6.8), boiled for 3 min. and subjected to 10% SDS polyacrylamide gel electrophoresis under non-reducing conditions. After the electrophoresis, the separated proteins were blotted to PVDF membrane (PROBLOTT™, Perkin Elmer) using a semi-dry electroblotter (BIO-RAD). The membrane was incubated at 37° C. with horseradish peroxidase-labeled anti-OCIF antibodies for 2 hr. After the membrane was washed, protein bands which react with the labeled antibodies were detected using an ECL™ system (Amersham). Two protein bands with approximate molecular weights of 60 kD and 120 kD were detected for the unaltered OCIF. On the other hand, almost exclusively a 60 kD protein band was detected for the OCIF-C23S, OCIF-CL and OCIF-CC mutants. Protein bands with approximate weights of 40 kD-50 kD and 30 kD-40 kD were the major ones for OCIF-CDD2 and OCIF-CDD1, respectively. These results indicate that Cys at 379 is responsible for the dimer formation, both the monomers and the dimers maintain the biological activity and a deletion of residues from Asp at 177 to Leu at 380 does not abolish the biological activity of OCIF (positions of the amino acid residues are shown in SEQ ID NO: 4).

EXAMPLE 23

Isolation of Human Genomic OCIF Gene i) Screening of a Human Genomic Library

An amplified human placenta genomic library in LAMBDA FIX™ II vector (Stratagene) was screened for the gene encoding human OCIF using the human OCIF cDNA as a probe. Essentially, screening was done according to the instruction manual supplied with the genomic library. The basic protocols described in *Molecular Cloning: A Laboratory Manual* were also employed to manipulate phage, *E. coli*, and DNA.

The library was titered, and 1×10⁶ pfu of phage was mixed with XL1-Blue MRA host *E. coli* cells and plated onto 20 plates (9 cm×13 cm) with 9 ml per plate of top agarose. The plates were incubated overnight at 37° C. Filter plaque lifts were prepared using HYBOND™-N nylon membranes (Amersham). The membranes were processed by denaturation in a solution containing 1.5 M NaCl and 0.5 M NaOH for 1 minute at room temperature. The membranes were then neutralized by placing each one in 1 M Tris-HCl (pH 7.5) and a solution containing 1.5 M NaCl and 0.5 M Tris-HCl (pH 7.5) successively for one minute each. The membranes were then transferred onto a filter paper wetted with 2×SSC. Phage DNA was fixed onto the membranes with 1200 microJoules of UV energy using a STRATALINKER UV CROSSLINKER™ 2400 (STRATAGENE) and the membranes were air dried. The membranes were immersed in Rapid Hybridization buffer (Amersham) and incubated for one hour at 65° C. before hybridization with ³²P-labeled cDNA probe in the same buffer overnight at 65° C. Screening probe was prepared by labeling the OCIF cDNA with ³²P using the Megaprime DNA labeling system (Amersham). Approximately, 5×10⁵ cpm probe was used for each ml of hybridization buffer. After the hybridization, the membranes were rinsed in 2×SSC for five minutes at room temperature. The membranes were then washed four times, 20 minutes each time, in 0.5×SSC containing 0.1% SDS at 65° C. After the final wash, the membranes were dried and subjected to autoradiography at −80° C. with SUPER HR-H™ X-ray film (FUJI PHOTO FILM Co., Ltd.) and an intensifying screen.

Upon examination of the autoradiograms, six positive signals were detected. Agar plugs were picked from the regions corresponding to these signals for phage purification. Each agar plug was soaked overnight in 0.5 ml of SM buffer containing 1% chloroform to extract phage. Each extract containing phage was diluted 1000 fold with SM buffer and an aliquot of 1 µL or 20 µL was mixed with host *E. coli* described above. The mixture was plated onto agar plates with top agarose as described above. The plates were incubated overnight at 37° C., and filter lifts were prepared, prehybridized, hybridized, washed and autoradiographed as described above. This process of phage purification was applied to all six positive signals initially detected on the autoradiograms and was repeated until all phage plaques on agar plates hybridize with the cDNA probe. After purification, agar plugs of each phage isolate were soaked in SM buffer containing 1% chloroform and stored at 4° C. Six individual phage isolates were designated λOIF3, λOIF8, λOIF9, λOIF11, λOIF12 and λOIF17, respectively.

ii) Analysis of the Genomic Clones by Restriction Enzyme Digestion and Southern Blot Hybridization DNA was prepared from each phage isolate by the plate lysate method as described in *Molecular Cloning: A Laboratory Manual*. DNA prepared from each phage was digested with restriction enzymes and the fragments derived from the digestion were separated on agarose gels. The fragments were then transferred to nylon membranes and subjected to Southern blot hybridization using OCIF cDNA as a probe. The results of the analysis revealed that the six phage isolates are individual clones. Among these fragments derived from restriction enzyme digestion, those fragments which hybridized with the OCIF cDNA probe were subcloned into plasmid vectors and subjected to nucleotide sequence analysis as described below.

iii) Subcloning Restriction Fragments Derived from Genomic Clones into Plasmid Vectors and Determining Their Nucleotide Sequence.

λOIF8 DNA was digested with restriction enzymes EcoRI and NotI and the DNA fragments derived therefrom were separated on a 0.7% agarose gel. The 5.8 kilobase pair (kb) EcoRI/NotI fragment was extracted from the gel using a QIAEX™ II Gel Extraction Kit (QIAGEN) according to the procedure recommended by the manufacturer. The 5.8 kb EcoRI/NotI fragment was ligated with pBLUESCRIPT II SK+™ vector (STRATAGENE), which had been linearized with restriction enzymes EcoRI and NotI, using READY-TO-GO™ T4 DNA Ligase (Pharmacia) according to the procedure recommended by the manufacturer. Competent DH5 α *E. coli* cells (Amersham) were transformed with the recombinant plasmid and transformants were selected on L-plates containing 50 µg/ml of ampicillin.

A clone harboring the recombinant plasmid containing the 5.8 kb EcoRI/NotI fragment was isolated and this plasmid was termed pBSG8-5.8. pBSG8-5.8 was digested with HindIII and a 0.9 kb DNA fragment derived from this digestion was isolated in the same manner as described above. This 0.9 kb fragment was then cloned into pBLUESCRIPT II SK−™ at the HindIII site as described above. This recombinant plasmid containing 0.9 kb HindIII fragment was denoted pBS8H0.9.

λOIF11 DNA was digested with EcoRI and 6 kb, 3.6 kb, 2.6 kb EcoRI fragments were isolated in the same manner as described above and cloned into a pBLUESCRIPT II SK+™ vector at the EcoRI site as described above. These recombinant plasmids were termed pBSG11-6, pBSG11-3.6, and pBSG11-2.6, respectively. pBSG11-6 was digested with HindIII and the digest was separated on a 0.7% agarose gel. Three fragments, 2.2 kb, 1.1 kb, and 1.05 kb in length, were extracted from the gel and cloned independently into pBLUESCRIPT II SK–™ vector at the HindIII site in the same manner as described above. These recombinant plasmids were termed pBS6H2.2, pBS6H1.1 and pBS6H1.05, respectively.

The nucleotide sequence of the cloned genomic DNA was determined using a ABI DYEDEOXY TERMINATOR CYCLE SEQUENCING READY REACTION™ Kit (PERKIN ELMER) and a 373A DNA Sequencing system (Applied Biosystems). Plasmids pBSG8-5.8, pBSG8H0.9, pBSG11-6, pBSG11-3.6, pBSG11-2.6, pBS6H2.2, pBS6H1.1 and pBS6H1.05 were prepared according to the alkaline-SDS procedure as described in *Molecular Cloning: A Laboratory Manual* and used as templates for DNA sequence analysis. The nucleotide sequence of the human OCIF gene is presented in SEQ ID NO: 104 and SEQ ID NO: 105. The nucleotide sequence of the DNA, between exon 1 and exon 2, was not entirely determined. There is a stretch of approximately 17 kb between the sequences given in SEQ ID NO: 104 and SEQ ID NO: 105.

EXAMPLE 24

Quantitation of OCIF by EIA
i) Preparation of Anti-OCIF Antibody

Male Japanese white rabbits (Kitayama Labs Co., LTD) weighing 2.5-3.0 kg were used in immunization for preparing antisera. For immunization, an emulsion was prepared by mixing an equal volume of rOCIF (200 µg/ml) and complete Freund's adjuvant (Difco, Cat. 0638-60-7). Three rabbits were immunized subcutaneously six times at one week intervals with 1 ml of emulsion per injection. Whole blood was obtained ten days after the final immunization and serum was isolated. Antibody was purified from serum as follows. Antiserum was diluted two-fold with PBS. After adding ammonium sulfate at a final concentration of 40% w/v, the antiserum was allowed to stand at 4° C. for 1 hr. The precipitate obtained by centrifugation at 8000×g for 20 min. was dissolved in a small volume of PBS and was dialyzed against PBS. The resultant solution was loaded onto a Protein G-SEPHAROSE™ column (Pharmacia). After washing with PBS, absorbed immunoglobulin G was eluted with 0.1 M glycine-HCl buffer (pH 3.0). The eluate was immediately neutralized with 1.5 M Tris-HCl buffer (pH 8.7) and dialyzed against PBS. Protein concentration was determined by absorbance at 280 nm ($E^{1\%}$ 13.5).

Horseradish peroxidase-labeled antibody was prepared using an IMMUNOPURE™ Maleimide Activated Horseradish Peroxidase Kit (Pierce, Cat. 31494). Briefly, one mg of IgG was incubated with 80 µg of N-succinimidyl-S-acetylthioacetate for 30 min. After deacetylation with 5 mg of hydroxylamine HCl, modified IgG was separated using a polyacrylamide desalting column. The protein pool was mixed with one mg of maleimide-activated horseradish peroxidase and incubated at room temperature for 1 hr.

ii) Quantitation of OCIF by Sandwich EIA

Figure 13:
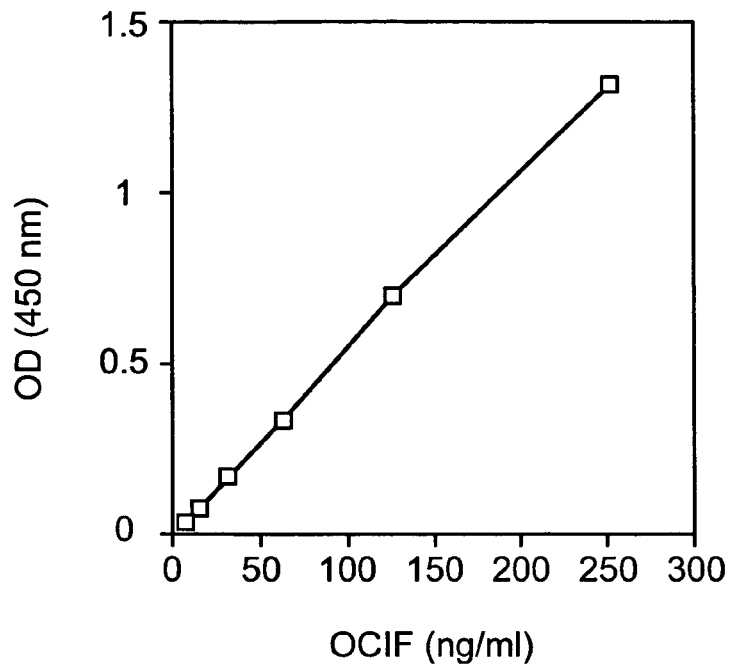
FIG. 13 shows a standard curve determining OCIF protein concentration by an EIA employing anti-OCIF polyclonal antibodies.

Microtiter plates (Nunc MaxiSorp Immunoplate) were coated with rabbit anti-OCIF IgG by incubating 0.2 µg in 100 µL of 50 mM sodium bicarbonate buffer pH 9.6 at 4° C. overnight. After blocking the plates by incubating for 1 hour at 37° C. with 300 µL of 25% BLOCKACE™/PBS (Snow Brand Milk Products), 100 µL samples were incubated for 2 hours at room temperature. After washing the plates three times with PBST (PBS containing 0.05% TWEEN™ 20), 100 µL of 1:10000 diluted horseradish peroxidase-labeled anti-OCIF IgG was added and incubated for 2 hours at room temperature. The amount of OCIF was determined by incubation with 100 µL of a substrate solution (TMB, ScyTek Lab., Cat. TM4999) and measurement of the absorbance at 450 nm using an IMMUNOREADER™ (Nunc NJ2000). Purified recombinant OCIF was used as a standard protein and a typical standard curve is shown in FIG. 13.

EXAMPLE 25

Anti-OCIF Monoclonal Antibody
i) Preparation of a Hybridoma Producing Anti-OCIF Monoclonal Antibody.

OCIF was purified to homogeneity from the culture medium of human fibroblasts, IMR-90 cells by the purification method described in EXAMPLE 11. Purified OCIF was dissolved in PBS at a concentration of 10 µg/100 µL. BALB/c mice were immunized by administering this solution intraperitoneally three times every two weeks. In the first and the second immunizations, the emulsion was composed of an equal volume of OCIF and Freund's complete adjuvant. Three days after the final immunization, the spleen was removed and lymphocytes isolated and fused with mouse myeloma p3x63-Ag8.653 cells according to conventional methods using polyethyleneglycol. Then the fused cells were cultured in HAT medium to select hybridomas. The presence of anti-OCIF antibody in the culture medium of each hybridoma was determined by solid phase ELISA. Briefly, each well of a 96-well immunoplate (Nunc) was coated with 100 µL of purified OCIF (10 µg/ml in 0.1 M NaHCO$_3$) and blocked with 50% BLOCKACE™ (Snow Brand Milk Products Co. Ltd.). The hybridoma clones secreting anti-OCIF antibody were established by limit dilution cloning 3-5 times and by solid phase ELISA screening. Several hybridoma clones producing high levels of anti-OCIF antibody were selected.

ii) Production of Anti-OCIF Monoclonal Antibodies.

Each hybridoma clone secreting anti-OCIF antibody obtained in EXAMPLE 25-i) was transplanted intraperitoneally into mice given Pristane (Aldrich) at a cell density of 1×10$^6$ cells/mouse. The accumulated ascites was collected 10-14 days after transplantation, thereby obtaining anti-OCIF specific monoclonal antibody of the present invention. Purified antibodies were obtained by Affigel protein A SEPHAROSE™ chromatography (BioRad) according to the manufacturer's manual. Briefly, the ascites fluid was diluted with an equal volume of a binding buffer (BioRad) and applied to a protein A column. The column was washed with a sufficient volume of binding buffer and eluted with an elution buffer (BioRad). After neutralizing, the eluate obtained was dialyzed in water and subsequently lyophilized. The purity of the antibody thereby obtained was analyzed by SDS/PAGE and a homogenous band with a molecular weight of about 150,000 was detected.

iii) Selection of Monoclonal Antibodies Having High Affinity for OCIF

Each antibody obtained in EXAMPLE 25-ii) was dissolved in PBS and the protein concentration was determined by the method of Lowry. Each antibody solution was diluted to the same concentration and then serially diluted with PBS. Monoclonal antibodies, which can recognize OCIF even at highly dilute concentrations, were selected by solid phase ELISA described in EXAMPLE 25-ii). Thus, three monoclonal antibodies A1G5, E3H8 and D2F4 were selected.

iv) Determination of Class and Subclass of Antibodies

The class and subclass of the antibodies of the present invention obtained in EXAMPLE 25-iii) were analyzed using an immunoglobulin class and subclass analysis kit (Amersham). The procedure was carried out according to the kit directions. The results are shown in Table 15. The antibodies of the present invention, E3H8, A1G5 and D2F4 belong to the $IgG_1$, $IgG_{2a}$ and $IgG_{2b}$ subclasses, respectively.

TABLE 15

Analysis of class and subclass of the antibodies in the present invention.

| Antibody | $IgG_1$ | $IgG_{2a}$ | $IgG_{2b}$ | $IgG_3$ | IgA | IgM | κ |
|---|---|---|---|---|---|---|---|
| A1G5 | – | + | – | – | – | – | + |
| E3H8 | + | – | – | – | – | – | + |
| D2F4 | – | – | + | – | – | – | + | v) Quantitation of OCIF by ELISA

Three kinds of monoclonal antibodies, A1G5, E3H8 and D2F4 obtained in EXAMPLE 25-iv), were used as solid phase antibodies and enzyme-labeled antibodies, respectively. Sandwich ELISA was constructed by different combinations of solid phase antibody and labeled antibody. The labeled antibody was prepared using an IMMUNOPURE™ TM Maleimide-Activated Horseradish Peroxidase Kit (Pierce, Cat. No. 31494). Each monoclonal antibody was dissolved in 0.1 M $NaHCO_3$ at a concentration of 10 μg/ml, and 100 μL of the solution was added to each well of a 96-well immunoplate (Nunc, MaxiSorp Cat. No. 442404) followed by allowing them to stand at room temperature overnight. Subsequently, each well of the plate was blocked with 50% BLOCKACE™ (Snow Brand Milk Products, Co., Ltd.) at room temperature for 50 minutes, and washed three times with PBS containing 0.1% TWEEN™ 20 (washing buffer).

A series of concentrations of OCIF was prepared by diluting OCIF with 1st reaction buffer (0.2 M Tris-HCl buffer, pH 7.4, containing 40% BLOCKACE™ and 0.1% TWEEN™ 20). Each well of a 96-well immunoplate was filled with 100 μL of the prepared OCIF solution with each concentration, allowed to stand at 37° C. for 3 hours, and subsequently washed three times with washing buffer. The POD-labeled antibody was diluted 400-fold with 2nd reaction buffer (0.1 M Tris-HCl buffer, pH 7.4, containing 25% BLOCKACE™ and 0.1% TWEEN™ 20), and 100 μL of the diluted solution was added to each well of the immunoplates. Each immunoplate was allowed to stand at 37° C. for 2 hours, and subsequently washed three times with washing buffer. After washing, 100 μL of a substrate solution (0.1 M citrate-phosphate buffer, pH 4.5, containing 0.4 mg/ml of o-phenylenediamine HCl and 0.006% $H_2O_2$) was added to each well of the immunoplates and the immunoplates incubated at 37° C. for 15 min. The enzyme reaction was terminated by adding 50 μL of 6 N $H_2SO_4$ to each well. The optical density of each well was determined at 492 nm using an immunoreader (IMMUNO-READER™ NJ 2000, Nunc).

Figure 14:
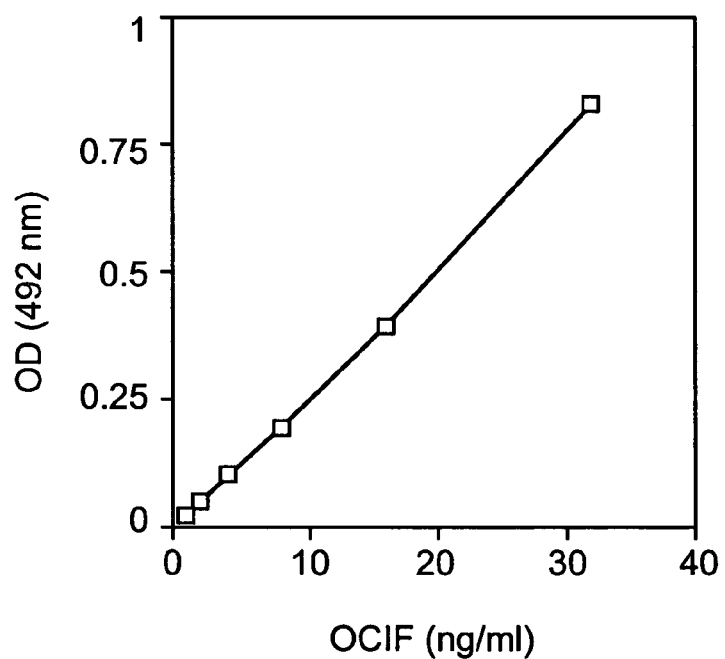
FIG. 14 shows a standard curve determining OCIF protein concentration by an EIA employing anti-OCIF monoclonal antibodies.
Figure 15:
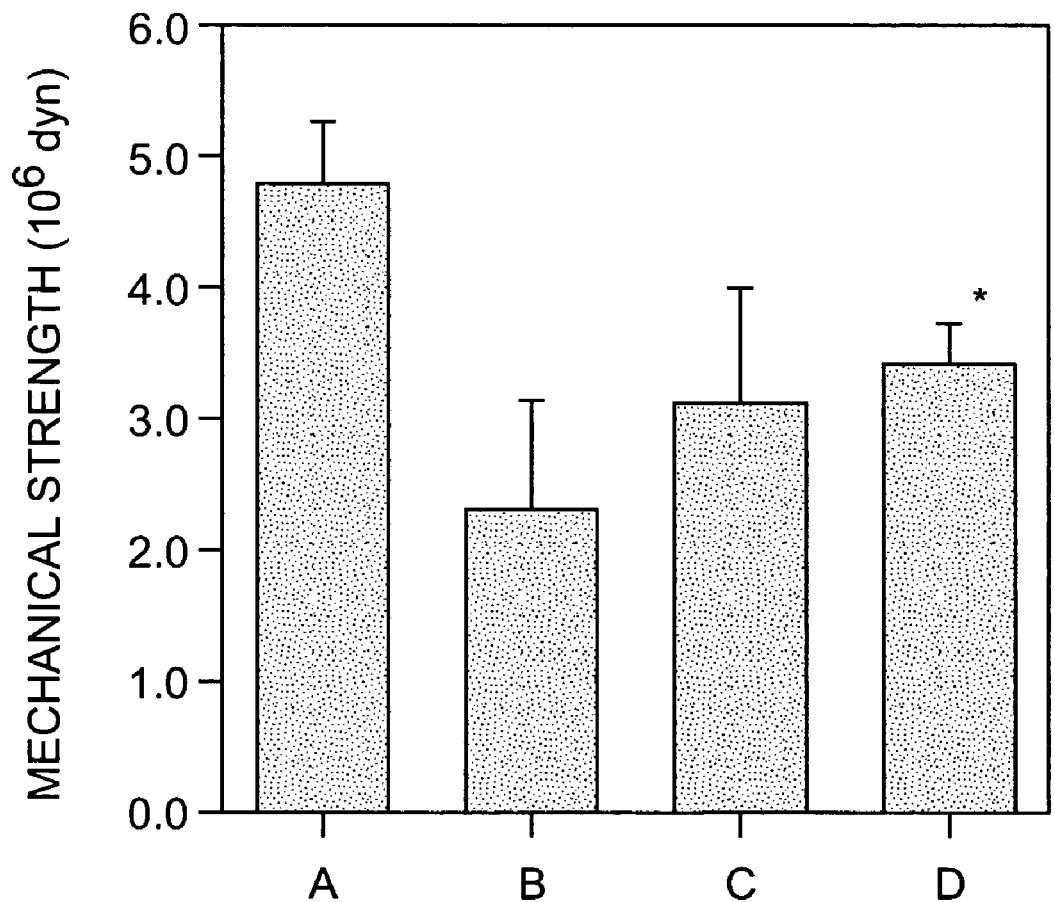
FIG. 15 shows the effect of rOCIF protein on model rats with osteoporosis.

Using three different monoclonal antibodies of the present invention, each combination of solid phase and POD-labeled antibodies leads to an accurate determination of OCIF concentration. Each monoclonal antibody of the present invention was confirmed to recognize a different epitope of OCIF. A typical standard curve of OCIF using a combination of solid phase antibody, A1G5, and POD-labeled antibody, E3H8, is shown in FIG. 14.

vi) Determination of OCIF in Human Serum

The concentration of OCIF in five samples of normal human serum was determined using an EIA system described in EXAMPLE 25-v). The immunoplates were coated with A1G5 as described in EXAMPLE 25-v), and 50 μL of the $1^{st}$ reaction buffer was added to each well of the immunoplates. Subsequently, 50 μL of each human serum was added to each well of the immunoplates. The immunoplates were incubated at 37° C. for 3 hours and washed three times with washing buffer. After washing, each well of the immunoplates was filled with 100 μL of POD-E3H8 antibody diluted 400-fold with the $2^{nd}$ reaction buffer and incubated at 37° C. for 2 hours. After washing the immunoplates three times with washing buffer, 100 μL of the substrate solution described in EXAMPLE 25-v) was added to each well and incubated at 37° C. for 15 min. The enzyme reaction was terminated by adding 50 μL of 6 N $H_2SO_4$ to each well of the immunoplates. The optical density of each well was determined at 492 nm using an immunoreader (IMMUNOREADER™ NJ 2000, Nunc).

Figure 2:
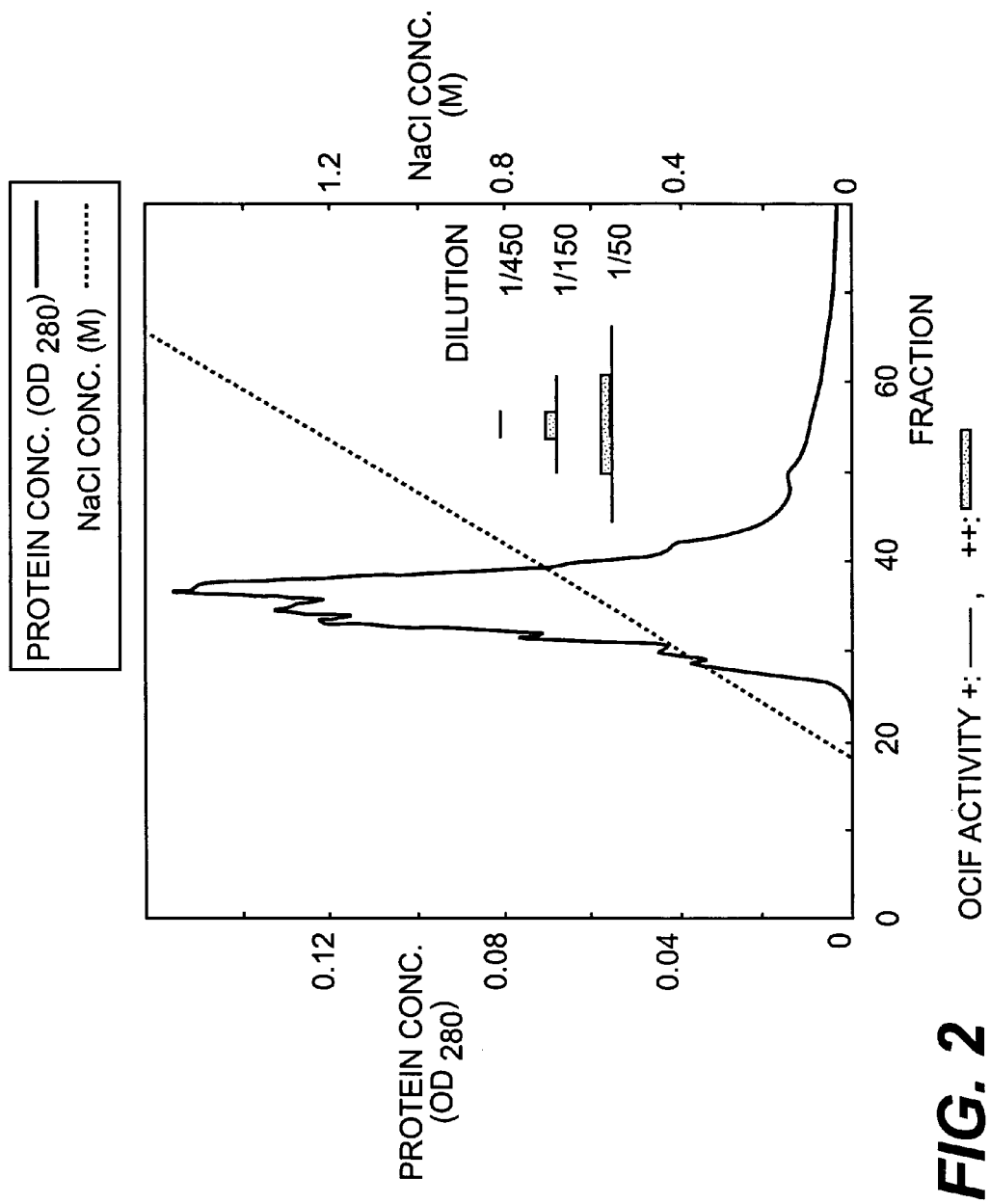
FIG. 2 shows the elution pattern of crude OCIF protein (heparin-5PW fraction; sample 5) from a blue-5PW column.

$1^{st}$ reaction buffer containing the known amount of OCIF was treated in the same way and a standard curve of OCIF as shown in FIG. 2 was obtained. Using the standard curve of OCIF, the amount of OCIF in human serum sample was determined. The results were shown in Table 16.

TABLE 16

The amount of OCIF in normal human serum

| Serum Sample | OCIF Concentration (ng/ml) |
|---|---|
| 1 | 5.0 |
| 2 | 2.0 |
| 3 | 1.0 |
| 4 | 3.0 |
| 5 | 1.5 |

EXAMPLE 26

Therapeutic Effect on Osteoporosis (1) Method

Six week old male Fischer rats were subjected to denervation of the left forelimb. These rats were assigned to four groups (10 rats/group) and treated as follows: group A, sham operated rats without administration; group B, denerved rats with the vehicle administered intravenously; group C, denerved rats with OCIF administered intravenously at a dose of 5 μg/kg twice a day; group D, denerved rats with OCIF administered intravenously at a dose of 50 μg/kg twice a day. After denervation, OCIF was administered daily for 14 days. After 2 weeks treatment, the animals were sacrificed and their forelimbs were dissected. Thereafter bones were tested for mechanical strength.

(2) Results

A decrease in bone strength was observed in control animals as compared to those animals of the normal groups while bone strength was increased in the group of animals that received 50 mg of OCIF per kg body weight.

Samples of the hybridomas that produce the claimed monoclonal antibodies were deposited in the National Institute of Bioscience and Human Technology National Institute of Advanced Industrial Science and Technology. The National Institute of Bioscience and Human Technology National Institute of Advanced Industrial Science and Technology accession numbers for the deposited hybridomas are:

| Hybridoma Antibody | | |
|---|---|---|
| Designation | Deposit Date | Accession No. |
| A1G5 | Feb. 5, 2001 | FERM BP-7441 |
| D2F4 | Feb. 5, 2001 | FERM BP-7442 |
| E3H8 | Feb. 5, 2001 | FERM BP-7443 |

These deposits were made under the Budapest Treaty and will be maintained and made accessible to others in accordance with the provisions thereof.

The hybridomas will be maintained in a public depository for a term of at least 30 years and at least five years after the most recent request for the furnishing of a sample of the deposit is received by the depository. In any case, samples will be stored under agreements that would make them available beyond the enforceable life of any patent issuing from the above-referenced application.

INDUSTRIAL AVAILABILITY

The present invention provides both a novel protein which inhibits the formation of osteoclasts and an efficient procedure for producing the protein. The protein of the present invention inhibits the formation of osteoclasts. The protein will be useful for the treatment of many diseases accompanied by bone loss, such as osteoporosis, and as an antigen to prepare antibodies useful for the immunological diagnosis of such diseases.

A national deposit of the microorganism (accession number Bikkoken No. P-14998) was made on Jun. 21, 1995, and transferred to the international depository named "National Institute of Bioscience and Human-Technology (NIBH), Agency of Industrial Science and Technology, Ministry of International Trade and Industry" having an address of 1-3, Higashi 1-chome, Tsukuba-shi, Ibaraki-ken, 305, JAPAN on Oct. 25, 1995 as accession number FERM BP-5267, pursuant to the Budapest Treaty. The deposit is a Budapest Treaty deposit and will be maintained and made accessible to others in accordance with the provisions thereof. The international depository is currently known as "International Patent Organism Depositary, National Institute of Advanced Industrial Science and Technology".

What is claimed:

1. An isolated nucleic acid molecule comprising the sequence of nucleotides 1 to 1206 of SEQ ID NO:6, inclusive, or the sequence of nucleotides 64 to 1206 of SEQ ID NO:6.

2. The nucleic acid molecule of claim 1 which is cDNA, genomic DNA or RNA.

3. An isolated nucleic acid encoding a polypeptide comprising the amino acid sequence from residues 1 to 380 of SEQ ID NO:4 or from residues 1 to 401 of SEQ ID NO:5.

4. The nucleic acid molecule of claim 3 which is cDNA, genomic DNA or RNA.

5. A cDNA comprising the nucleotide sequence as provided in SEQ ID NO:6.

6. A cDNA comprising the nucleotide sequence of nucleotides 64 to 1206 of SEQ ID NO:6.

7. A cDNA encoding the amino acid sequence as provided in SEQ ID NO:4.

8. A cDNA encoding the amino acid sequence as provided in SEQ ID NO:5.

9. An expression vector comprising an isolated nucleic acid molecule comprising the sequence of nucleotides 1 to 1206 of SEQ ID NO:6 or the sequence of nucleotides 64 to 1206 of SEQ ID NO:6.

10. An expression vector comprising an isolated nucleic acid molecule encoding a polypeptide comprising the amino acid sequence from residues 1 to 380 of SEQ ID NO:4 or from residues 1 to 401 of SEQ ID NO:5.

11. A host cell comprising an expression vector comprising an isolated nucleic acid molecule comprising the sequence of nucleotides 1 to 1206 of SEQ ID NO:6, inclusive, or the sequence of nucleotides 64 to 1206 of SEQ ID NO:6.

12. A host cell comprising an expression vector comprising an isolated nucleic acid molecule encoding a polypeptide comprising the amino acid sequence from residues 1 to 380 of SEQ ID NO:4 or from residues 1 to 401 of SEQ ID NO:5.

* * * * *